(12) United States Patent
Hogrefe et al.

(10) Patent No.: US 7,442,766 B2
(45) Date of Patent: Oct. 28, 2008

(54) PFU REPLICATION ACCESSORY FACTORS AND METHODS OF USE

(75) Inventors: Holly Hurlbut Hogrefe, San Diego, CA (US); Janice Marie Cline, San Marcos, CA (US); Connie Jo Hansen, San Diego, CA (US)

(73) Assignee: Stratagene California, La Jolla, CA (US)

( * ) Notice: Subject to any disclaimer, the term of this patent is extended or adjusted under 35 U.S.C. 154(b) by 175 days.

(21) Appl. No.: 10/828,924

(22) Filed: Apr. 20, 2004

(65) Prior Publication Data

US 2005/0003401 A1 Jan. 6, 2005

Related U.S. Application Data

(63) Continuation of application No. 09/626,813, filed on Jul. 27, 2000, now abandoned.

(60) Provisional application No. 60/146,580, filed on Jul. 30, 1999.

(51) Int. Cl.
C07K 14/00 (2006.01)
C12P 19/34 (2006.01)
C12N 15/63 (2006.01)
C12N 1/20 (2006.01)

(52) U.S. Cl. .................. 530/350; 435/194; 435/91.1; 435/320.1; 435/252.3; 435/325; 536/23.1

(58) Field of Classification Search .............. 530/350; 435/194

See application file for complete search history.

(56) References Cited

U.S. PATENT DOCUMENTS

| 5,545,552 A | 8/1996 | Mathur |
| 5,866,395 A | 2/1999 | Mathur |

FOREIGN PATENT DOCUMENTS

| EP | 0821058 A2 | 1/1998 |
| EP | 0870832 | 10/1998 |
| EP | 0997530 A1 | 5/2000 |
| WO | WO 95/16028 | 6/1995 |
| WO | WO 98/42860 | 10/1998 |
| WO | WO 99/00506 | 1/1999 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
U.S. Appl. No. 09/648,641, filed Aug. 25, 2000, Allen et al.
U.S. Appl. No. 08/822,774, filed Mar. 21, 1997, Hogrefe.
U.S. Appl. No. 09/414,295, filed Oct. 6, 1999, Hogrefe et al.
Baker et al., 1998, Cell, 92:295-305.
Bult et al., 1996, Science, 273:1058-1073.
Chedin et al., 1998, TIBS, 23:273-277.
Cline et al., 1996, Nucl. Acids Res., 24:3546-3551.
Edgell, et al., 1997, Cell, 89:9959-998.
Kelly et al., 1998, PNAS, 95:14634-14639.
Lundberg et al., 1991, Gene, 108:1-6.
McHenry et al., 1997, J. Mol. Biol., 272:178-189.
Mathur et al., 1991, Nucl. Acids Res., 19:6952.
Ngo et al., 1994, in *The Protein Folding Problem and Tertiary Structure Prediction*, Merz et al. (ed.), Birkhauser, Boston, MA, pp. 433 and 492-495.
Sandhu et al., 1994, Gene, 144:53-58.
Uemori et al., 1997, Genes to Cells, 2:499-512.
International Search Report for PCT Application No. PCT/US00/20532, mailed Mar. 5, 2001.

* cited by examiner

*Primary Examiner*—Richard G Hutson

(57) ABSTRACT

This invention provides isolated polynucleotides that encode replication accessory factors. The invention also provides novel DNA replication accessory factors, which have been isolated and purified from the hyperthermophilic archaea *Pyrococcus furiosus*. The invention also provides various methods of enhancing a nucleic acid polymerase reaction comprising the addition of the replication accessory factors to the reaction. This invention further provides methods of synthesizing, amplifying, and mutagenizing nucleic acids of interest employing the replication accessory factors. This invention also provides kits comprising at least one of the replication accessory factors. This invention also provides kits useful for various methods that comprise at least one replication accessory factor.

28 Claims, 37 Drawing Sheets

FIG. 3

```
ATGCCATTCGAAATAGTCTTTGAAGGTGCAAAAGAGTTTGCCCAACTTAT
AGACACCGCAAGTAAGTTAATAGATGAGGCCGCGTTTAAAGTTACAGAAG
ATGGGATAAGCATGAGGGCCATGGATCCAAGTAGAGTTGTCCTGATTGAC
CTAAATCTCCCGTCAAGCATATTTAGCAAATATGAAGTTGTTGAACCAGA
AACAATTGGAGTTAACATGGACCACCTAAAGAAGATCCTAAAGAGAGGTA
AAGCAAAGGACACCTTAATACTCAAGAAGGAGAGGAAAACTTCTTAGAG
ATAACAATTCAAGGAACTGCAACAAGAACATTTAGAGTTCCCCTAATAGA
TGTAGAAGAGATGGAAGTTGACCTCCCAGAACTTCCATTCACTGCAAAGG
TTGTAGTTCTTGGAGAAGTCCTAAAAGATGCTGTTAAAGATGCCTCTCTA
GTGAGTGACAGCATAAAATTTATTGCCAGGGAAAATGAATTTATAATGAA
GGCAGAGGGAGAAACCCAGGAAGTTGAGATAAAGCTAACTCTTGAAGATG
AGGGATTATTGGACATCGAGGTTCAAGAGGAGACAAAGAGCGCATATGGA
GTCAGCTATCTCTCCGACATGGTTAAAGGACTTGGAAAGGCCGATGAAGT
TACAATAAAGTTTGGAAATGAAATGCCCATGCAAATGGAGTATTACATTA
GAGATGAAGGAAGACTTACATTCCTACTAGCCCCCAGGGTCGAGGAGTGA
```

FIG. 4

```
MPFEIVFEGAKEFAQLIDTASKLIDEAAFKVTEDGISMRAMDPSRVVLID
LNLPSSIFSKYEVVEPETIGVNMDHLKKILKRGKAKDTLILKKGEENFLE
ITIQGTATRTFRVPLIDVEEMEVDLPELPFTAKVVVLGEVLKDAVKDASL
VSDSIKFIARENEFIMKAEGETQEVEIKLTLEDEGLLDIEVQEETKSAYG
VSYLSDMVKGLGKADEVTIKFGNEMPMQMEYYIRDEGRLTFLLAPRVEE*
```

5U TPL + 1μl OF CLAMP DILUTION / 50μl PCR

5U TPL + 1μl OF CLAMP DILUTION / 50μl PCR

FIG. 8

```
ACCCAAAATTGTTATTCAGNTCAACGGAGAAGACGGAGTAGANTTGGAAGG
AGCTTATCCAGAGAAATGTTCTTAGAGAAGTTACTCTCAGCTCTCAGCTGA
TCTANNGTTTTTCCTTCTTTTCTTCTGTTCAGTTATNGCCTAGGATAAGCT
TAATAATACTTTGATACCTTTCTTAGTTTAGGTGTGTGAGAGTATGAGCGA
AGAGATTAGAGAAGTTAAGGTTCTAGAAAAACCCTGGGTTGAGAAGTATAG
ACCTCAAAGACTTGACGACATTGTAGGACAAGAGCACATAGTGAAAAGGCT
CAAGCACTACGTCAAAACTGGATCAATGCCCCACCTACTCTTCGCAGGCCC
CCCTGGTGTCGGAAAGTGTCTTACTGGAGATACCAAAGTTATAGCTAATGG
CCAACTCTTTGAACTTGGAGAACTTGTTGAAAAGCTTTCTGGGGGAGATT
TGGACCAACTCCAGTTAAAGGGCTCAAAGTTCTTGGAATAGATGAGGATGG
AAAGCTTAGAGAGTTTGAAGTCCAATACGTCTACAAAGATAGAACTGATAG
GTTGATAAAGATAAAAACTCAGCTTGGCAGGGAGCTTAAAGTAACTCCGTA
TCACCCACTTCTAGTGATTGGAGAGAATGGCGAATTAAAGTGGATTAAGGC
TGAAGAACTCAAACTTGGCGACAAGCTTGCAATACCGAGCTTTCTCCCACT
TATAACTGGAGAAAATCCCCTTGCAGAGTGGCTTGGTTACTTTATGGGAAG
TGGCTATGCTTATCCCAAGAATTCTGTCATCACGTTCACTAACGAAGATCC
ACTCATAAGACAACGCTTTATGGAACTAACAGAGAAACTTTTCCCTGATGC
AAAGATAAGGGAAAGAATTCACGCTGATGGAACTCCAGAAGTTTATGTGGT
ATCTAGGAAAGCTTGGAGCCTTGTAAACTCTATTAGCTTAACATTAATACC
CAGGGAGGGGTGGAAAGGAATTCGTTCTTTCCTTAGGGCATATTCCGACTG
CAATGGTCGGATTGAAAGTGATGCAATAGTTTATCAACCGATAACAATGA
TATGGCCCAGCAGATAGCCTATGCTTTAGCCAGCTTTGGAATAATAGCTAA
AATGGATGGAGAAGATGTTATTATCTCAGGCTCGGACAACATAGAGAGGTT
CCTAAATGAGATTGGCTTTAGCACCCAAAGCAAACTTAAAGAAGCCCAGAA
GCTCATTAGAAAAACCAATGTAAGATCCGATGGACTAAAGATTAACTATGA
GCTAATCTCCTATGTAAAAGACAGGCTTAGGTTAAATGTCAATGATAAAAG
AAATTTGAGCTACAGAAATGCAAAGGAGCTTTCTTGGGAACTCATGAAAGA
AATTTATTATCGCCTTGAGGAACTGGAGAGACTAAAGAAGGTCTTATCAGA
ACCCATCTTGATCGACTGGAATGAAGTAGCAAAGAAGAGTGATGAAGTAAT
AGAAAAAGCTAAAATTAGAGCAGAGAAGCTCCTAGAATACATAAAAGGAGA
GAGAAAGCCAAGTTTCAAGGAGTACATTGAGATAGCAAAAGTCCTTGGAAT
TAACGTTGAACGTACCATCGAAGCTATGAAGATCTTTGCAAAGAGATACTC
AAGCTATGCCGAGATTGGAAGAAAACTTGGAACTTGGAATTTCAATGTAAA
AACAATTCTTGAGAGCGACACAGTGGATAACGTTGAAATCCTTGAAAAGAT
AAGGAAAATTGAGCTTGAGCTCATAGAGGAAATTCTTTCGGATGGAAAGCT
CAAAGAAGGTATAGCATATCTCATTTTCCTCTTCCAGAATGAGCTTTACTG
GGACGAGATAACTGAAGTAAAAGAGCTTAGGGGAGACTTTATAATCTATGA
TCTTCATGTTCCTGGCTACCACAACTTTATTGCTGGGAACATGCCAACAGT
AGTCCATAACACTACAGCGGCTTTGGCCCTTGCAAGAGAGCTTTTCGGCGA
AAACTGGAGGCATAACTTCCTCGAGTTGAATGCTTCAGATGAAAGAGGTAT
AAACGTAATTAGAGAGAAGTTAAGGAGTTTGCGAGAACAAAGCCTATAGG
AGGAGCAAGCTTCAAGATAATTTTCCTTGATGAGGCCGACGCTTTAACTCA
AGATGCCCAACAAGCCTTAAGAAGAACCATGGAAATGTTCTCGAGTAACGT
TCGCTTTATCTTGAGCTGTAACTACTCCTCCAAGATAATTGAACCCATACA
GTCTAGATGTGCAATATTCCGCTTCAGACCTCTCCGCGATGAGGATATAGC
GAAGAGACTAAGGTACATTGCCGAAAATGAGGGCTTAGAGCTAACTGAAGA
AGGTCTCCAAGCAATACTTTACATAGCAGAAGGAGATATGAGAAGAGCAAT
AAACATTCTGCAAGCTGCAGCAGCTCTAGACAAGAAGATCACCGACGAAAA
(cont.)
```

FIG. 8 (cont.)

CGTATTCATGGTAGCGAGTAGAGCTAGACCTGAAGATATAAGAGAGATGAT
GCTTCTTGCTCTCAAAGGCAACTTCTTGAAGGCCAGAGAAAAGCTTAGGGA
GATACTTCTCAAGCAAGGACTTAGTGGAGAAGATGTACTAGTTCAGATGCA
CAAAGAAGTCTTCAACCTGCCAATAGAGGAGCCAAGAAGGTTCTGCTTGC
TGATAAGATAGGAGAGTATAACTTCAGACTCGTTGAAGGGCTAATGAAAT
AATTCAGCTTGAAGCACTCTTAGCACAGTTCACCCTAATTGGGAAGAAGTG
ATGAAGTATGCCAGAGCTTCCCTGGGTAGAAAATACAGGCCAAAAAGTT
AAGTGAAATTGTAAACCAAGAAGAGGCTATAGAGAAAGTTAGAGCGTGGAT
AGAGAGCTGGTTGCATGGCCACCCCCTAAGAAAAAGCCCTATTATTAGC
AGGACCCCAGGGAGCGGAAAGACAACCACAGTCTACGCTCTAGCAAATGA
GTACAACTTTGAAGTCATTGAGCTCAACGCGAGTGATGAGAACTTATGA
AAAAATCTCCAGGTATGTTCAAGCAGCATACACTATGGATATCCTCGGAAA
GAGGAGGAAGATAATCTTCCTCGATGAAGCAGATAATATAGAGCCCAGCGG
AGCTAAGGAAATCGCAAAACTAATTGATAAGGCCAAAAATCCAATAATAAT
GGCTGCAAATAAGTACTGGGAAGTTCCAAAAGAGATCCGAGAAAAGCTGA
GCTAGTAGAGTACAAGAGGTTAACCCAGAGAGATGTAATGAATGCCTTAAT
AAGGATCCTAAAGAGGGAAGGTATAACAGTTCCAAAAGAAATCCTCCTAGA
AATAGCAAAAGATCTAGTGGAGATCTAAGAGCAGCTATAAATGATCTACA
GACCGTTGTAGTGGGTGGTTACGAAGATGCTACGCAAGTTTTGGCATATAG
AGATGTAGAAAGACAGTCTTTCAAGCCCTAGGACTCGTCTTTGGAAGTGA
CAACGCCAAGAGGGCAAAGATGGCAATGTGGAACTTGGACATGTCCCCTGA
TGAATTCCTGCTATGGGTAGATGAGAACATTCCTCACCTCTACCTAAATCC
AGAGGAGATTGCCCAGGCGTATGATGCAATTAGTAGAGCCGACATATACCT
CGGAAGGGCCGCCAGAACTGGAAACTATTCACTCTGGAAGTACGCAATAGA
TATGATGACTGCAGGAGTTGCCGTGGCAGGGAGAAAGAGAAGGGGATTTGT
CAAGTTTTATCCTCCCAACACCCTAAAGATTTTAGCGGAAAGCAAAGAAGA
AAGAGAGATCAGAGAGTCCATAATTAAAAAGATAATACGAGAGATGCNCAT
GAGTAGGCTACAGGCAATAGAAACGATGAAAATAATTAGAGAGATTTTCGA
GAACAATCTAGACCTTGCTGCGCACTTTACAGTGTTCCTTGGTCTGTCTGA
AAAAGAAGTTGAGTTTCTAGCTGGAAGGAAAAAGCTGGTACCATTTGGGG
CAAAGCCTTAGCATTAAGAAGGAAACTTAAGGAGCTTGGAATAAGAGAGGA
GGAGAAGCCTAAAGTTGAAATTGAAGAAGAGGAAGAAGAGGAAGAAAAGAC
CGAAGAAGAAAAAGAGGAAATAGAAGAAAACCCGAAGAAGAGAAAGAAGA
GGAGAAGAAAGAAAGGAAAAGCcaaAGAAAGGCAAACAAGCAACTCTCTT
TGACTTTCTTAAAAAGTGATTACCCTTTTTCTTCTATTAGAGCTCCGAATA
AAGTTGGCCCTCTAATTTTTTCTATTGTCTCCTCCACATTAATCTTTACGA
ATTGGAATTCCTGCAGCCCGGGGGATCCACTAGTTCTAGAGCGGCCGCCAC
CGCGGTGGAGCTCCAGCTTTTGTTCCCTTTAGTGAGGGTTAATTTCGAGCT
TGGCGTAATCATGGTCATAGCTGTTTCCTGTGTGAATTGTTATCCGCTCA
CAATTCCACACAACATACGAACCCGGAAGCATAAATTGTAAACCCNGGGGT
GCCTAATGANTGANCTAACTCACATTAATTGCNTTGCGCTCACTGCCCGCT
TTCCANTCGGGAAACCTGTCGTGCCAGCTGCATTAATGAATCGGCCAACNC
GCGGGGANAAGCGGTTGCGTATTGGGCGCTCTTCCGCTTCCTCGCTCATGA
CTCGCTGCGCTCGGTCNTCGGCTGCGGCGAACGGTATCAGCTCATCAAAGG
CGGTAATACGGTTATCCNCAAATCAGGGGATAACGCAGGAAAAACTTTNN
ACAAAAGGCNNCAAAAGGCGGAAACTAAAAGGCGCNTTCTGGGTTTTTCNT
AGGCCCNCCCCGANAACTCNAAAAATCAACNCATTCAAGTGGGAAACCAAA
GAA

FIG. 9

PKIVIQXNGEDGVXLEGAYPEKCS*RSYSQLSADLXFFLLFFCSVXA*DK
LNNTLIPFLV*VCES(MSEEIREVKVLEKPWVEKYRPQRLDDIVGQEHIV
KRLKHYVKTGSMPHLLFAGPPGVGK[CLTGDTKVIANGQLFELGELVEKL
SGGRFGPTPVKGLKVLGIDEDGKLREFEVQYVYKDRTDRLIKIKTQLGRE
LKVTPYHPLLVIGENGELKWIKAEELKLGDKLAIPSFLPLITGENPLAEW
LGYFMGSGYAYPKNSVITFTNEDPLIRQRFMELTEKLFPDAKIRERIHAD
GTPEVYVVSRKAWSLVNSISLTLIPREGWKGIRSFLRAYSDCNGRIESDA
IVLSTDNNDMAQQIAYALASFGIIAKMDGEDVIISGSDNIERFLNEIGFS
TQSKLKEAQKLIRKTNVRSDGLKINYELISYVKDRLRLNVNDKRNLSYRN
AKELSWELMKEIYYRLEELERLKKVLSEPILIDWNEVAKKSDEVIEKAKI
RAEKLLEYIKGERKPSFKEYIEIAKVLGINVERTIEAMKIFAKRYSSYAE
IGRKLGTWNFNVKTILESDTVDNVEILEKIRKIELELIEEILSDGKLKEG
IAYLIFLFQNELYWDEITEVKELRGDFIIYDLHVPGYHNFIAGNMPTVVH
N]TTAALALARELFGENWRHNFLELNASDERGINVIREKVKEFARTKPIG
GASFKIIFLDEADALTQDAQQALRRTMEMFSSNVRFILSCNYSSKIIEPI
QSRCAIFRFRPLRDEDIAKRLRYIAENEGLELTEEGLQAILYIAEGDMRR
AINILQAAAALDKKITDENVFMVASRARPEDIREMMLLALKGNFLKAREK
LREILLKQGLSGEDVLVQMHKEVFNLPIEEPKKVLLADKIGEYNFRLVEG
ANEIIQLEALLAQFTLIGKK)**S(MPELPWVEKYRPKKLSEIVNQEEAI
EKVRAWIESWLHGHPPKKKALLLAGPPGSGKTTTVYALANEYNFEVIELN
ASDERTYEKISRYVQAAYTMDILGKRRKIIFLDEADNIEPSGAKEIAKLI
DKAKNPIIMAANKYWEVPKEIREKAELVEYKRLTQRDVMNALIRILKREG
ITVPKEILLEIAKRSSGDLRAAINDLQTVVVGGYEDATQVLAYRDVEKTV
FQALGLVFGSDNAKRAKMAMWNLDMSPDEFLLWVDENIPHLYLNPEEIAQ
AYDAISRADIYLGRAARTGNYSLWKYAIDMMTAGVAVAGRKRRGFVKFYP
PNTLKILAESKEEREIRESIIKKIIREMXMSRLQAIETMKIIREIFENNL
DLAAHFTVFLGLSEKEVEFLAGKEKAGTIWGKALALRRKLKELGIREEEK
PKVEIEEEEEEEKTEEEKEEIEEKPEEEKEEEKKEKEKPKKGKQATLFD
FLKK)*LPFFFY*SSE*SWPSNFFYCLLHINLYELEFLQPGGSTSSRAAA
TAVELQLLFPLVRVNFELGVIMVIAVSCVKLLSAHNSTQHTNPEA*IVNP
GVPNX*XNSH*LXCAHCPLSXRETCRASCINESANXRGXAVAYWALFRFL
AHDSLRSVXGCGERYQLIKGGNTVIXKSGDNAGKNFXQKAXKGGN*KAXS
GFFXGPPRXLXKSTHSSGKPK

FIG. 10

MPELPWVEKYRPKKLSEIVNQEEAIEKVRAWIESWLHGHPPKKKALLLAG
PPGSGKTTTVYALANEYNFEVIELNASDERTYEKISRYVQAAYTMDILGK
RRKIIFLDEADNIEPSGAKEIAKLIDKAKNPIIMAANKYWEVPKEIREKA
ELVEYKRLTQRDVMNALIRILKREGITVPKEILLEIAKRSSGDLRAAIND
LQTVVVGGYEDATQVLAYRDVEKTVFQALGLVFGSDNAKRAKMAMWNLDM
SPDEFLLWVDENIPHLYLNPEEIAQAYDAISRADIYLGRAARTGNYSLWK
YAIDMMTAGVAVAGRKRRGFVKFYPPNTLKILAESKEEREIRESIIKKII
REMXMSRLQAIETMKIIREIFENNLDLAAHFTVFLGLSEKEVEFLAGKEK
AGTIWGKALALRRKLKELGIREEEKPKVEIEEEEEEEKTEEEKEEIEEK
PEEEKEEEKKEKEKPKKGKQATLFDFLKK*

FIG. 11

MSEEIREVKVLEKPWVEKYRPQRLDDIVGQEHIVKRLKHYVKTGSMPHLLF
AGPPGVGKTTAALALARELFGENWRHNFLELNASDERGINVIREKVKEFAR
TKPIGGASFKIIFLDEADALTQDAQQALRRTMEMFSSNVRFILSCNYSSKI
IEPIQSRCAIFRFRPLRDEDIAKRLRYIAENEGLELTEEGLQAILYIAEGD
MRRAINILQAAAALDKKITDENVFMVASRARPEDIREMMLLALKGNFLKAR
EKLREILLKQGLSGEDVLVQMHKEVFNLPIEEPKKVLLADKIGEYNFRLVE
GANEIIQLEALLAQFTLIGKK**

FIG. 16

ATGAGT₇GCATTTACAAAAGAAGAAATAATCAAGAGGATCCTGGAAGAAG
TGGAAGGAATAACTCTAGAAGAAATTGAGAACCAAATAAGGCAAATAATG
AGGGAAAACAATATTTCAGAGCATGCAGCTGCTCTCTTACTAGCAGAAAG
GCTGGGAGTTGAAGTTACCAAAAGAGAAGAACAACCTTTAATGAAGATTA
GCGACCTATATCCAGGAATGGATCCCCACGAGGTCAACATTGTTGGAAGA
ATACTTAAGAAGTATCCACCGCGAGAATACACAAAGAAGGATGGAAGCAT
TGGAAGGGTTGCCAGTCTAGTTATATACGATGATACTGGGAGAGCGAGGG
TTGTTCTTTGGGATTCAAAAGTTTTGGAGTATTACAGCAAGCTAGAAGTA
GGGGATGTTATTAAGGTTTTAGACGCCCAGGTTAGGGAGAGCTTATCTGG
TTTGCCTGAATTGCACATTAACTTCAGGGCTAGAATAATTAAAAACCCAG
ATGATCCTAGGGTTCAGGATATCCCACCTCTTGAAGAAGTTAGAGTGGCA
ACTTATACGAGAAAGAAGATCAGTGAGGTCGAGCCTGGGGATAGATTTGT
AGAGCTTAGGGGAACAATTGCCAAAGTTTACAGAGTTTTGGTATATGATG
CATGTCCAGAGTGTAAGAAGAAGGTTGACTATGACCCAGGAATGGACGTT
TGGATATGTCCAGAACATGGAGAGGTTGAGCCAATAAAAATCACTATTCT
TGACTTTGGCTTGATGATGGCTCGGGATACATTAGGATTACCCTCTTTG
GAGACGATGCTGAAGAGTTGCTGGGAGTAGGGCCAGAAGAGATTGCCCAA
AAGCTTAAGGAAATGGAGAGCATGGGCATGACTCTCAAGGAGGCAGCGAG
AAAATTGGCGGAGGAAGAGTTCTACAATATAATAGGGAAAGAAATAATCG
TGAGGGGAAATGTAATTGAGGACAGGTTCTTGGGCCTAATCTTAAGGGCC
TCCTCCTGGGAAGAAGTTGACTACAAGAGAGAAATTGAGAGAATTAAGAG
GGAATTGGAAGAATTGGGGGTGATGTGA

FIG. 17

MI₃MSAFTKEEIIKRILEEVEGITLEEIENQIRQIMRENNISEHAAALLLA
ERLGVEVTKREEQPLMKISDLYPGMDPHEVNIVGRILKKYPPREYTKKDG
SIGRVASLVIYDDTGRARVVLWDSKVLEYYSKLEVGDVIKVLDAQVRESL
SGLPELHINFRARIIKNPDDPRVQDIPPLEEVRVATYTRKKISEVEPGDR
FVELRGTIAKVYRVLVYDACPECKKKVDYDPGMDVWICPEHGEVEPIKIT
ILDFGLDDGSGYIRITLFGDDAEELLGVGPEEIAQKLKEMESMGMTLKEA
ARKLAEEEFYNIIGKEIIVRGNVIEDRFLGLILRASSWEEVDYKREIERI
KRELEELGVM

Pfu TURBO WITH RFA

RFA/50 μl PCR RXN
1. 0
2. 1μl
3. 1μl 1/10
4. 1μl 1/100

Pfu TURBO WITH RFA

RFA/50 μl PCR RXN
1. 0 λ
2. 1 λ
3. 1 λ of 1/10
4. 1 λ of 1/100

FIG. 22

```
ATGATTGAGGAGCTGTTCAAGGGATTAGAGAGTGAAATCGTTGGACTTCA
CGAGATTCCCCCAAAGAGGGGAGAGTATGGGGAGTTCAAATTCAGGAATG
AAGAAGTTAATGAGTTAGTTAAGAGGCTCGGATTTAGACTTTATTCTCAC
CAAGTTAAAGCCCTAGAAAAGCTGTATTCAGGGAAAAACGTAGTTGTTTC
AACGCCCACAGCTAGTGGGAAAAGCGAGATATTTAGGTTGTTTATCTTTG
ACGAAATACTGTCAAGCCCGTCCTCAACTTTTCTCTTAATCTACCCAACA
AGAGCCTTAATAAACAACCAAATGGAAAATTCGAAAAGAAAACACTAT
CTTTGAGGAGATTTGTGGAAAAGAGTTCGAGCAGAAGTCTTAACTGGAG
ATACGGAATGGGAAAGAGAAGAGAAATCATTAGGAGCAAACCAAACGTA
ATCTTCACGACACCCGATATGCTTCATCATCACATTCTTCCCAGGTGGAG
GGATTATTTCTGGCTTTTAAAGGGGCTTAGACTTCTTGTCGTGGACGAAT
TGCACGTTTATAGGGGATCTTTGGAACAAATGTTGCTTATGTTTTCAAG
AGACTCTTTCTCAGGCTTAAGAGATTAAGTTCAAGCCCCAAATACTTGC
CCTTTCAGCAACTTTGAGAAACCCCAAAGAATTTGCTGAACAATTTTTG
AGACTGAATTTGAGGAGGTCAAGGAAGCTGGAAGTCCAAGCCCGAGAAGA
ATTATAGTCATGTTTGAGCCAAGAAGGTTTACTGGAGAACAACTAATCAA
GCAAATTGTTGAGAGACTAACTAGAAAGAACATAAAGACCTTGGTATTTT
TTGACTCCAGAAAGGGGACAGAAAGAATCATGAGGCTTTTCCTGTTCTCA
GATGCTTTTGATAGGATCACAACATACAAAGGGACGCTAACTAAGAGGGA
AAGGTTTCTAATAGAGAGAGACTTTAGGGAGGGCAACCTCACAGTTCTCC
TAACGACAAATGCACTCGAGTTGGGAATTGACATTGGAGATTTAGATGCA
GTAATAAACTATGGGATTCCTTCAGATGGATTGTTTTCACTAATTCAAAG
ATTTGGTAGGGCCGGAAGGGATCCAAATAGAATTGCAATAAACGGGATAA
TTTTGAGAAGAAATGGATTGGACTACTATTACAAAGAACATTTCGATGAG
CTCGTTGAGGGAATAGAAAAGGGCCTAGTGGAGAAAATCCCCGTTAACTT
GGACAATGAAAAGATAGCGAAAAGCACCTCCACTATGCCATAGCTGAAC
TTGGAGTTGTCTCAATTAAAGAAATTGAGGGGAGATGGAAGAGATTCATA
AAGACCCTCGTAGAGGAGGGATACGTGGAAGTTACAAGAAATCCAATAAC
TGGAGAGGAAGAAATAAGACTCAGAAGACCTCCTGTCTATTCTTCAATTA
GAACGGCGAGCGATGAAAGCTACTTCTTAGTCGTGGATGAACCCTGGATA
AGGGGAGCTTTGCAGAGGAAGAGGGGAGCCGAACTTCTCCGTTTTGTAAA
CTACCTCAAAGTTAGAGGAATGGTAGTTGAGGAAGTTGATGAGATAGAAT
TCCACAGAAGTCTACTCCCTGGAATGGTCTACCTTTCAAGGGGAAGGCCC
TACATGGCAGTTGATAAGATAAAGATTGAGAAGTTCCACTTCGTTTTTGC
GAGGCCTCTTCCAATCGAAGAAGAAATAGATACTAGTTCAAGTAAAATTG
AAAACATTGAGATACTTGAGGTTAAAGACGAGAAACTGTTGGCCCAATA
AAAGTGAAGTTCGGAAGACTTAGAGTAAGGCACGAATACACTGGATACGC
CGTGAGGGGAAGAGACGTTGAAAGGCACGTTAAGAGATTAGAAGAGCTAA
AAGATGAGGGGATACTAAGGGGAGAGATTGACATCGTCCCATACATTTGG
GAATCCTGGAAGTTTGCGAGGGTACTCTTTGACACCCCTACATTAGAGA
GTTTGAAACTGAAGGTTTCTGGCTTGAGTTTCCAAACGATATTAGGATAG
TTCCCGAAGAGGAGTTTAGGGAATTCTTTGCAGTGGCCTCTGAGATAGAT
CCAGAGCTCGCGATGTTCCTCTACAACAGAATTAGTAGAAAATCTCTATT
CCCCACGCTTCTGGGAGCAACCACACACTACATAAGGAGTTTCATCCTTC
(cont.)
```

FIG. 22 (cont.)

```
ACCACGCCAAAGATAAGGGAGAAGAATTCGCATTTGCCGTAAAAAAGATG
ATCGACAGCAAGGATGGGATAGGCTCAGGGCTTCATGCAATTGAGCCCAA
TATAATAAAGCTTGCTCCAGTTGTGACTCATGTGGATTCGAGAGAAATAG
GCGGCTACAGCTACGATGACTTCCATGGAAAGCCAGTGATCTTCATCTAT
GATGGGAATGAAGGCGGAAGCGGAATAATTAGGCAGGTGTATGAGAACGT
AGAAAAGCTGATGTACAGGAGTTTGGAGCATATAAAGAAGTGTCCATGCA
AAGACGGCTGTCCTGCCTGCATATATTCTCCCAAGTGCGGAACTTTCAAT
GAATTCCTCGACAAGTGGATGGCAATAAGAATATGGGAAAAGTCCTTCC
TTAA
```

FIG. 23

```
ATGTTAATAGTTGTAAGACCAGGAAGAAAAAGAATGAGCTCGAGGCTTTTA
TAATTGAAAACCCTCCAGAAAGCTCTCTCAAGAAGAAATTTAAAAGCTGA
TAGGGTAGTTAGGCTCATAATGAGAGATAATAGACTTTTTAAAGCTCTTGAA
GGAAGTCAGTATTTAAATCCAAAGGAAGTGGAGAGAGCCCTTAGAAATTCAA
GGATAGTTCTGGTGAATGCCAACGAGTGGGAAGAGTACTTTAAGAAGAGGTT
AATGAACAAAAGAGTTGAAAAGCTGACATCTGTAGGCTCTGCCTTCTCAAT
GGGAAGATTACAGTACTCACTGAGGGAAACAGGATAAGATACAGAGATGAAT
ACATATGTGAAAGTTGTGCCGAGGAGGAGTTGAAGAGAGAGTTAAGATTTCG
ATTTAATTCCATAGGAATGCTTGAACAGGCAAAGAAGCTTTTAGAGAGATTC
AGAGATTTAGACAAGGTGATTTCAATTTTTGATCCATCCTTTGACCCCACTA
AGCATCCAGAGATAACAAAATGGGATGAGCTAAAGGCCAAGCATATAAGGGT
CGAGAAGATGCATATAGATGAGCTCAACATCCCCGAAGAATTCAAAAAGTT
CTAAAGGCCGAAGGAATAAACGAACTACTCCCCGTTCAGGTGCTAGCGATTA
AAAACGGCCTCCTAGAGGGGAGAATTTATTGGTGGTTTCAGCAACTGCGAG
TGGAAAAACTCTAATCGGAGAGCTTGCAGGTATTCCTAAGGCTCTAAAGGGA
AAGAAAATGCTGTTCCTAGTTCCTCTAGTAGCTTTAGCAAACCAAAAGTACG
AGGACTTCAAGAGAAGATACTCAAAGCTTGGATTAAAAGTAGCCATTAGAGT
CGGAATGAGCAGGATAAAGACCAAGGAAGAGCCAATAGTTCTGGATACTGGA
ACAGATGCACACATAATAGTGGGGACTTACGAAGGAATAGACTACCTTCTCA
GAGCTGGTAAAAAGATAGGAAACGTTGGAACGGTTGTAATAGATGAAATACA
CATGCTCGATGATGAGGAGAGAGGAGCTAGGCTAGATGGGCTCATTGCAAGG
TTAAGGAAGCTCTATTCAAATGCCCAATTTATTGGGCTTTCAGCAACCGTAG
GAAACCCTCAGGAGTTAGCCAGGAAGCTAGGGATGAAACTAGTGCTTTACGA
TGAAAGGCCCGTTGACTTAGAGAGGCATTTAATAATTGCGAGAAATGAGAGT
GAGAAGTGGAGGTATATAGCTAAGCTGTGCAAAGCCGAGGCCATGAGAAAGA
GCGAGAAGGGATTCAAGGGGCAGACGATAGTATTTACATTTTCAAGGAGAAG
ATGCCATGAGCTTGCCTCATTCCTAACGGGGCAGGGATTGAAGGCTAAGGCC
TACCACTCGGGCCTCCCCTATGTTCAGAGAAAGCTTACCGAAATGGAGTTTC
AAGCTCAAATGATTGATGTAGTTGTAACAACAGCTGCTTTAGGAGCGGGAGT
TGATTTTCCAGCATCCCAAGTCATCTTCGAAAGCTTGGCCATGGGAAACAAG
TGGATAACAGTTAGGGAGTTTCACCAAATGCTTGGCAGGGCTGGAAGGCCAC
AGTACCATGAGAAAGGTAAAGTTTACATAATAGTCGAGCCTGGGAAAAAGTA
CTCAGCTCAGATGGAGGGAACTGAAGATGAAGTCGCCCTCAAGCTCTTGACT
TCACCCATAGAACCAGTAATTGTTGAGTGGAGCGATGAATTTGAAGAGGATA
ATGTCTTAGCTCATGCCTGTGTGTTTAATAGACTTAAAGTTATTGAAGAAGT
TCAATCCCTCTGCCTGGGAGCAAACCAAAGTGCTAAAAATGTTTTGGAAAAA
CTTATGGAAAAGGGGCTCGTCAAAATATATGGAGATAAAGTTGAAGCAACCC
CATATGGAAGGCGGTGAGCATGAGTTTCCTACTTCCTAGGGAGGCAGAGTT
CATCAGAGATAACTTGGAGAGCACTGATCCAATTGAGATAGCAATTAAACTG
CTACCGTTCGAAAACGTTTACCTCCAGGATCGCTCCAGAGGGAAATAGAGT
CAGCTGTTAGAGGAAAGATAAGCTCAAACATCTTTTCAAGCTCCTTTGCATC
AGTGCTAGAAGAGCTTGACAAGATTATACCCGAAATAAGCCCAAATGCTGCA
GAAAGGCTATTCCTAATATACCAAGATTTCTTCAACTGCCCAGAGCAAGACT
GTACGGAGTTTGCAATGGAGAGAATTGGGAGAAAGATCATTGACTTAAGAAG
AGAGGGATACGAGCCCTCAAAAATCTCTGAGCACTTTAGGAAGGTCTATGCA
TTAATATTATACCCTGGAGATGTTTTACATGGTTAGACGGAATTGTGAGAA
AACTCGAGGCAATTGAAAGAATAGCCCGAGTGTTCAATAAGAGAAGAGTGGT
AGAAGACACAATCAGGGTTAGAAGGGAAATTGAAGAAGGAAAAATTTTGAAG
GGTGAGAGACGATGA
```

FIG. 24

```
ATGCACAAATACTTCTTTCCATTACCTGCAACTAAGTCAACTTTCTTGCTC
CCTGCCGACCTCACCACAGCAAATCCATGCTTTTCCAAGAGCTTAATCAAT
TCTCTCTCTGCCTGGGCCCCTTTTCTATACATACAATGTTTTTCCTATCTA
CCTCTTATAAACTTTTTAAACTCCTTGACATACCCTCTCGAGATGCACATA
TTGATAAAAAAGGCAATAAAGAGAGATTTGGAAAGTTGAATGCCCTTCAA
CAATTAGCCTTTCATAAAATTAGGGGAGAAGGTAAAAGTGTTTTAATAATA
GCTCCGACAGGAAGCGGAAAAACTGAAGCCGCAGTAATTCCAATCTTAGAC
GCAATACTACGGGAGAATCTTAAACCTATAGCAGCTATTTATATAGCCCCA
TTGAAGGCACTAAATAGGGACTTGCTAGAGAGACTAAAGTGGTGGGAAGAA
AAAACTGGGGTAATAATAGAGGTTAGGCATGGGGACACGCCTACCTCAAAA
AGATTGAAGCAGGTAAAAAATCCTCCCCACCTATTAATTACAACCCCTGAA
ATGCTCCCTGCTATTCTTACGACAAAGTCCTTCCGTCCCTATCTTAAGAAC
ACTAAATTTATCGTGATAGACGAGATTGGTGAACTTATAGAGAATAAAAGA
GGAACCCAGCTAATCCTAAATCTAAAAGACTTGAATTAATTACAGAAGAT
AAACCAATAAGGATTGGCCTTTCTGCAACAATTGGAAGTGAAGAAAAGGTA
AGGCTTTGGATGGAAGCGGATGAAGTGGTAAAGCCTCGACTAAAAAGAAG
TACAAATTTACCGTTTTATACCCTCAGCCAATTCCAGAGGATGAAAAGCTT
GCTGAAGAGCTCAAAGTTCCAATAGAAGTTGCAACGAGGCTAAGAGTTGTG
TGGGATATTGTAGAAAAGCACAAGAAGGTATTGATCTTTGTTAATACCCGA
CAATTTGCAGAGATCTTAGGGCATAGACTTAAAGCTTGGGGAAAACCTGTT
GAAGTTCACCATGGTAGCCTTTCAAGGGAAGCAAGAATAGAGGCAGAGAAG
AAACTTAAGGAAGGAAAATAAAAGCACTAATTTGTACCTCATCAATGGAA
CTTGGCATTGACATAGGGGATGTTGATGCAGTTATTCAGTACATGAGTCCT
CGACAGGTAAATAGGCTAGTCCAGAGAGCTGGAAGAAGCAAACATAGACTG
TGGGAAACAAGCGAGGCTTACATCATAACCACAAACGTAGAAGATTATCTC
CAAAGCTTGGCAATAGCAAAGCTCGCACTAGAAGGAAAACTGGAAGATGTA
AATCCCTACGAAAATGCCCTTGATGTCCTGGCTCACTTTATAGTTGGTTTG
ACAATAGAATACAGAAATGTTAACATTACTGAACCCTATTCCCTTGCGAAA
TCTACTTATCCCTACAGAAAGCTCTCCTGGGAAGACTATCAGAAAGTTTTA
GAGATTTTAGAAGAGGCTAGAATAATAAGAAGAGATGGAGATGCAATTAAG
CTGGGAAAAAATGCCTTTAAGTATTATTTCGAGAACCTCTCAACAATACCT
GACGAAATAAGTTATGCAGTTATAGATATTGCAAGTGGAAAATCTGTTGGA
AGACTAGATGAAACTTTGTTACGGAACTTGAAGAGTATGGAATTCATC
ATGCATGGAAGAAGCTGGATCGTGCTGGAATTAACGAAAAGAAAGGATA
ATAAAGGTTAAGGAGAGCAACAATTTAGAAAGTGCACTGCCAAGTTGGGAA
GGGGAGCTCATTCCAGTTCCTTTGGAAGTTGCAGAATTTGTTGGAAAGCTG
AAGAGAGAGCTCCTATGGGACAAAGAGAGCATTAAAACTGCTTGAGGGC
GTTGAATTTAATAAGGAAGAACTCGAGGTTGCAATTTCCCAACTAGTAGAA
TCAGAACCAGTGGCGAGTGATAGAGATATCATTATAGAATCCTATCCAAAA
TTTGTGATAATTCATGCTGATTTTGGAAATAAAATTAACGAAGGGCTCACA
AGATTTATCTCAGTGTTTTATCCGCCCGATATGGGAATATTTTCCTCCCA
AGAAGTCAAGCTCATGGAATTATAATTAGAAGCCCATTTAGGCTTAATCCT
GAAGAAATAAAGGAAATACTGTTAATGAAAGCAGAAGTTGGAGATATTGTT
GCTAGAGGAATTAGAGACACTCCAATATACCGCTGGAAGATGAGTGCAATT
GCTAAGAGATTCGGTGCCCTAAGAAGGGACGCGAGAATAAAAAAGTAGAA
AGGCTGTTTGAAGGGACAATAATAGAGAAGGAGACTTTTAATGAAATTTAC
(cont.)
```

FIG. 24 (cont.)

```
CATGATAAAATCGACATTGATAAAACAGAGAAAATTCTAGAAAAAATAAGA
AAGGGAGAAATTAGAATGAAAACTTTGTTCAGAGAGGAAATAACGCCTCTT
TCCTCTTCTTTGGCAACCCTAGGAGGAGAGTTTCTAATTAGAGATATACTT
ACCCAGGAGGAAGTAGAAGAGATATTTAGGGAGAAGTTACTCGATGCTGAG
TTAGTCATGGTTTGTACAAACTGCGGATTTTCCTGGAGAACAAAAGTTCGC
AGGGTTATGGATAGAGTCAATGAGTTAAGCTGTCCCAAGTGTGATTCCAAA
ATGATAGCTCCTCTACACCCCAAAGATTCCGAAACTTTCATCTCAGCTCTC
AAAAAGTTAAAAGAGGAGAAAGCTTAGTAGGGAAGAAGAAAAGTATTAC
CTTAGAGGTTTAAAGGCGGCTGATTTACTTAAAGCCTACGGGAAGGACGCT
CTTTTAGCATTAGCTACCTATGGGGTTGGGGTAGAAAGCGCCACCAGAATA
CTTAGGGATTATAGAGGAAATCCCTTATAAAAGCACTTATCGAGGCAGAG
AAACACTACATCCAAACTAGAAAGTTTTGGGAATAG
```

FIG. 25

```
GTGATGTTATTAAGGAGAGACTTAATACAGCCTAGGATATATCAAGAGGTA
ATATACGCCAAGTGCAAAGAAACAAACTGCTTGATTGTTCTGCCCACAGGA
TTAGGTAAGACGCTGATAGCTATGATGATAGCAGAGTATAGATTAACGAAA
TATGGCGGAAAAGTTCTAATGCTCGCCCCACTAAGCCTCTCGTTCTTCAA
CATGCGGAAAGTTTTAGGAGGCTATTTAACCTCCCTCCAGAAAAATTGTA
GCACTTACTGGAGAGAAGAGCCCAGAAGAGAGAAGTAAGGCCTGGGCGAGA
GCAAAAGTAATTGTAGCCACTCCTCAAACTATTGAAAATGACTTATTGGCG
GGAAGAATATCTTTAGAAGACGTTTCGCTAATAGTATTCGATGAAGCTCAC
AGAGCTGTGGGCAATTACGCTTACGTCTTTATAGCAAGAGTATAAAAGA
CAGGCCAAAAACCCACTTGTTATAGGGTTAACAGCCTCCCTGGGAGCACT
CCTGAAAAGATCATGGAGGTAATAAATAACTTGGGAATTGAGCATATTGAA
TACCGCTCCGAAAATTCTCCCGATGTTAGACCTTACGTTAAGGGAATAAGG
TTTGAATGGGTTAGGGTTGATCTCCCAGAAATATACAAGGAAGTAAGGAAA
CTTTTAAGAGAAATGCTTAGAGATGCCCTTAAACCGTTGGCAGAAACTGGA
CTTCTTGAATCTTCTTCCCCAGACATTCCAAAGAAAGAAGTTCTTAGAGCT
GGGCAAATAATAAACGAAGAAATGGCGAAAGGTAATCATGATCTCAGAGGC
TTGCTTCTCTATCACGCAATGGCTCTTAAGCTACATCATGCAATTGAGCTG
TTGGAAACCCAAGGGTTATCCGCCCTGAGGGCTTATATAAAGAAGTTGTAT
GAGGAGGCAAAAGCGGGATCAACAAAGGCTAGCAAGGAAATATTCTCGGAT
AAGAGAATGAAAAGGCAATCTCACTTTTAGTTCAAGCGAAGGAGATTGGG
CTTGATCACCCCAAGATGGACAAGTTAAAAGAAATAATTAGGGAACAACTC
CAAAGGAAACAAAATTCCAAAATCATAGTTTTCACTAACTACAGAGAAACT
GCAAAAAGATAGTCAATGAACTTGTGAAAGATGGAATAAAAGCTAAAAGG
TTCGTTGGACAGGCCAGCAAAGAAAATGACCGTGGACTGAGTCAGAGAGAG
CAGAAATTAATTCTTGACGAATTCGCTAGAGGAGAATTCAACGTTCTAGTG
GCAACGAGTGTAGGAGAGGAAGGACTTGACGTGCCGGAAGTTGATTTGGTT
GTGTTTTATGAGCCAGTACCATCTGCCATAAGGAGCATCCAAAGAAGGGGT
AGAACTGGCAGGCATATGCCGGGGAGAGTTATAATCCTAATGGCCAAGGGG
ACTAGAGATGAAGCATACTACTGGAGTTCCAGGCAAAAGGAAAAGATAATG
CAAGAGACAATAGCTAAGGTGAGTCAGGCAATTAAAAAGCAGAAGCAAACT
TCTCTAGTTGATTTTGTGAGAGAAAAGAGAGCGAAAAGACCTCTCTAGAC
AAGTGGTTGAAAAGGAAAAGAAGAAGCAACTGAAAAGAGGAAAGAAG
GTAAAGGCTCAAGAGGGTGTAAAAGTCGTCGTAGATAGCAGAGAGCTTAGG
AGTGAGGTTGTGAAGAGACTTAAACTTCTTGGTGTAAAGTTAGAGGTTAAA
ACGCTCGATGTGGGAGATTATATAATTAGTGAGGACGTTGCAATTGAGAGG
AAGTCAGCTAACGACTTCATTCAGTCAATTATTGATGGTAGACTTTTTGAT
CAAGTTAAGAGGCTCAAAGAGGCATACTCAAGACCGATAATGATAGTCGAA
GGTTCTTTATACGGAATTAGAAACGTCCATCCAAATGCAATAAGGGGGGCA
ATAGCAGCGGTAACCGTAGACTTTGGGGTCCCAATAATATTTTCATCTACT
CCAGAGGAAACCGCTCAATACATCTTTCTAATTGCAAAGAGGGAGCAAGAG
GAGAGAGAAAAACCTGTGAGAATTAGAAGTGAGAAGAAGGCCCTTACCCTT
GCCGAGAGGCAGAGGTTAATAGTTGAGGGATTACCTCACGTCTCAGCAACT
CTAGCTAGGAGATTGTTGAAGCACTTTGGAAGTGTGGAAGGGTATTCACT
GCAAGCGTTGCTGAGTTAATGAAAGTTGAAGGCATAGGAGAGAAGATTGCT
AAGGAGATTAGAAGGGTAATAACTGCCCCATATATAGAGGATGAGGAGTAG
```

FIG. 26

```
TTGAAAGGGTTGTTTAGGGACGTTATCCTCCACAACCCCCACCTTTTTGTT
TATTCCTATTCTGATAAAGGCATCATTCCTTTCAAGCATCAGTTCCAGACC
CTCTATCATGCCATGCTCATGAGGCCAGTGAGGCTAATGATAGCTGATGAG
ATAGGTCTCGGAAAGACCATTCAAGCTCTTTTAATAGCCAAGTACCTCGAT
TTTAGGGGAGAGATTGAGAAAGCCTTGATAGTCGTTCCAAAAGTTCTGAGG
GAGCAGTGGAGGGAAGAAGTAAAGAGGATCTTAGAGGAAGCTCCGGAAGTG
ATAGAGAATGGTAGCGAATTGAATGGAAGTTGAAAAGGCCGAGGAAGTAC
TTCATAATATCAATAGACCTAGCTAAGAGATACACCGAGGAAATACTCCGT
CAAAAGTGGGATTTAGTAATAGTTGACGAAGTCCACAACGCCACCCTGGGA
ACACAGAGATATGAGTTCTTAAAAGAACTAACCAAGAACAAGGATTTGAAC
GTTATATTCCTTTCAGCAACCCCCACAGGGGAAACAATAGAGATTACCTT
GCGAGGCTTAGGCTCCTCGACCCAACTATACCAGAGGAAATATCCCCAATG
CACGAAAGGAAGATCTACATGAAGTCAAGAGGGACATTGGTACTAAGGCGA
ACTAAGAAGGTTGTCAACGAACTTGAAGGAGAAGTGTTCAAGAAGTGTCAC
TTTGGGGCTGTCGTGGTAGAAGTTAGCAGAGAGGAGAGGGAGTTCTTTGAA
GAGTTAAATAGAGCGCTATTCGAGCTGATTAAGGATCAAGCTGATTACTCT
CCCTTAACTCTTCTTGCAGTAATCATTAGGAAGAGAGCCTCGTCCAGCTAC
GAAGCGGCTCTAAAAACCCTAACCAGGATCGTTGAAAGCGCTTATATAAGT
GGGCAAGAAAGAGCCAGAGGCGTTGAATCATACATTGAAAAGATCTTTAGA
ATGGGGTATGAGGAATTGGAAATAGAAGAATTTAACGAGATAGATGATGCG
ATACACAAAATAATAGATGAATATAGGGGATTCTTAACTGAAGAGCAACTC
GAAAGGCTTAGAAGAGTTCTCGAGCTTGGAAAGAAAATTGGCAGCAAGGAT
AGCAAGCTTGAGGTTATATCCGATATAGTTGCTTATCACATTAGGAACGGC
GAAAAGGTCATAATATTCACGGAATTTAGAGATACCCTCGAATACGTACTT
GAGAGGTTACCAGATATCCTAAGGAGAAAGCACGGCATTGTTTTGGAAAAA
GATGACATTGCAAAACTTCATGGGGGCATGAAATCTGAGGAAATAGAGAGG
GAAATCAACAAGTTTCATGAAAGGGCTAACCTATTAGTCTCTACGGATGTT
GCATCCGAAGGACTTAACCTGCACGTTGCAAGTGTTGTAATAAACTACGAG
GCCCCCTGGAGCCCAATAAAGCTCGAACAGAGGGTGGGAAGAATATGGAGG
CTCAACCAAACGAGAGAAACCAAAGCATATACCATATTTCTTGCAACGGAA
ACGGACTTGGATGTTCTAAACAACCTCTATAGAAAGATTATGAACATAAAG
GAAGCCGTGGGAAGTGGACCCATTATTGGAAGGCCAATATTTGAAGGAGAC
TTTGAAAATCTATGGAATGAAGGTGCCGAGGAAGAAAATAGAGAAGTCTCA
GAGTATGAGCTTATCCTAGCCTCAATTAAGGGAGAACTCAAGGGCTATGCC
GGGGCTCTAGTTAGGACTCTCAGAATCCTAAAGCAGAAAGTGGAGGGAGCA
GTTCCTGTAAATCCTGCGGGAAGCATAAGGAGAGAGCTCGAGATAATTTTA
GAGGACACTCCTGATGTGGAAGTATTAAAGAAATCGTTAATAGGAACGTT
CCAAATCCGTTCCGCTTGGTGAGAGGACTTTTAAGAGAAGCCGAGGGGATT
GAGGGAATTAGAGTATTAGTTAAGGGCTATGATGGCTCTATGGATGTGTAC
TATGCCATATTCTACGACGAAGATGGGAGAGAAATTTATAGATATCCAATT
CTTGCTGAGAACGGAAAGTACCTTGTTGGATTCAACTTACTCAAGAGGATT
AGTGAGGTACTATCCAAAGAGTACAAGGTCGTTAGAGGGGCAAGTGAAGAG
GTGGACTATAAAGTTAAGACGCTAGTTATGGACAACATATACAATTTAATC
GTGAAGAAGTATCTGGAATACGATAGCTTAAACATCAAAGAAGGTAAAATC
TTCAAGAGGCTTAAGGTTGAAATAAAGAAAGCCCTCGAGGTAAAGGGGATA
(cont.)
```

FIG. 26 (cont.)

```
AGTGAAGAAGAATTCGAAGTCATCAAGAGAGTTCCCCCTGAGATTATGGAA
GTTCTAGGGTTAGATTCCACAAAAATAGAACTACCTACCAACGAATACCTC
AAGATCTTCGAAGGAACTTTGTTCCTCTGGATAAAATCCTTGAGAGTGAA
AAGAAGGCCATGGAAATAGTCATGGAGCTAGAGAAGAGCAGAGGATATAAC
GTTGAGGACGTATCTTTAAGGGAGCACTATGACATAAGGGCCTTTACAGAT
GGTGAAGAGAAGTACATAGAGGTCAAAGGCCACTATCCAATGCTCCTACTT
GCGGAGTTAACGGAAAGGAATTTGAGTTCGCACAAAAAAATGAAGATAAG
TACTGGATATACATAGTCTCGAACATTGCCAAAGACCCCGTAATTGTAAAA
ATTTACAAACCATTTTCCCAGGATAGAAGAGTATTCGTGGTTAAGAATGGG
GAAGATGTTGAGGTTAATATCAACATTGAGATAAAGAAGAAAGATAGGCAT
TTACTTAAGTTAAGCTAG
```

FIG. 27

```
GTGATTACTTTGGAGCTACATCCAAGTGAGATAGCTAGATATTTCGAGCTT
GAAGAGTGTTCCCACTATTTCTCTAACCTACTTTTAAGAAAGAGAGGCGAA
TTGCAGGAATTTGAGCCGATAATAAGGAGAAAGAAATAGAAACCATAGAG
CTCGCCAAATGGGGAGACGAGTTCGAGCTCTCCCTTCTTCAGGAATTTAAA
AAAGGTGAAGCATTAAAAAGCTTGGAGTTAAGAACTACCAAGATTCTAT
GGTTTTTTAACGGAAAACGACACCCTGTAAGAAAGTTCTTTGAAAAGTAC
TTTAAAGATGGAATAATAGTGGAAGAAGATCCAGACAAACTTTTAGAAATT
ATAAACAGTGAGAAAGTGCCGTTATCTATCAAGCCCCTTAAAAGGCAGA
ATAGGGAAATTTGATGTCTCAGGAAGGGCAGACTTCATAATAAAGGTTGGG
AAAACACTTTACCTACTCGAGGCTAAGTTTACTAAGGAAGAGAAGTTCTAC
CACAGGATTCAGGCCATTATCTATGCTCACCTTCTAAGTCAAATGATCGAA
GGTTACGAAATTAAACTAGCTGTTGTAACAAAGGAGAACTTTCCCATTCCC
TCAAACTTCCTAAGATTCCCAGGAGACGTGGAAGAGTTAAGATAACCCTA
GAAGAAAGCTTGGTGGAATACTAAGAGAACAAGAACTTTGGATAGACGCA
AGGTGTACTACTTGCCCCTTTGAGGCTTTATGCTTGTCTAAGGCTCTTGAG
GAAAGAAGTCTAGGACTATTAAGCCTTCCCCCTGGGATAATTAGAATACTC
AAAGAAGAAGGGATAAAAGACTTAAAAGACATGGCTAAGCTATTTGAATTC
AAAGAAAATTCCCCTACAAACTTTGAAGAGCCCTCAATAAAAGATCCAAAG
AAGACTCAAGAGATAGCAAAAGAACGGGAATAAACTTACTAAAGCTCTCA
AGGATAGCTCAGGCAATCCTTAAATATTTAGATGAGGGAGAAACAACACCC
CTGTTCATCCCCAGGACGGGGTATAATCTGCCAATGGATGAGAGAGTAGGT
GATGTTGAGCCCTCTTACTATCCTCCAAGGAGCTTAGTGAAAGTGTTCTTC
TATGTCCAGACAAGCCCAATAACAGACACAATAATCGGAATTTCAGCCCTT
GTAAAGAATAGGCAAAATGGAGAGCGGATAATTGTTAAGTTCGTCGATGAG
CCCCCCATAGAAGTTTCAGATGCCCAAGAAAGGAGAGAATGCTTCTAATT
GAGTTCTTTAGGGATGTTATTGATGCCGTAAAGTCACTATCTCCAACCGAT
AAAGTCTACCTACACATGTACTTTTACAATAGAAACAGAGAGATGACCTT
ATGGATGCCGTAAAGAGACACAAAGAGATAAGAGAAAACAATGCAGTCATG
GCCTTGCTAAGCTTGAGAAGAGCCATAGATTGGGAGAGCTTTTCAATAATA
AAGGATGAGATAATAAGGAGGCATGCCTTACCACTTTCTCCTGGCCTGGGA
TTCGTTACAGTTGCTACTCAGTTTGGATACAGATGGAGAAGGAACAAAACC
TTTGCGCGAATGCTTGAGGTTGTAGCAAGAAGAGAAATGGTAAGATAAAT
CTCAAAACTCTCCTTAACATTTCTGAAACGGGAATTGGGCCAGAATATTAT
CCAATCATCGATAGGGATAACGAAGGAATACCCTTCACACTTTTCTGGAGC
GCACTGGTCAAATTAGCTACTGAGGAAGACAATTCAAGAATTAAGAGGGAT
ATAAGGGACATACTCTCCCAAATGGTTGAGGCCCTCAAAACAATTGAAGAG
AGAATTCCCGAGCAATATAAAGACGCCTTCGTGAAAAAGAGGGAATACCC
AAAGAAGATCTCGAAACTTTGACATAAAGAAGGAAGAATTAGCTGATATC
CTTCTTGAATACTTACAATTAGAGTTCGATGCAAGATTTAGAGAACGATCC
GAATACTATAGGCTTCCCCTATCAATAAGAGCATACTCAGAGGAATCAGCA
CTAATTAAGATAGAAACATTGAAAAGAAGAAAATGACTGTCTGTTGTTT
GGAAAAATCGTGCTAATTGACGAAATGGAAGAATAAAGAGTATAATCCA
AAAGAAGTTCTTATAGATATTGATGAAGGTTCTCTTGTAGTTGTAACGCCA
AAGAAATTCTTAGATAAGCTAAGAAGAGATCCCGTTCAAAGAATAAGCAAA
TCACCGTTAGGAATAGTTGAGGCTATAGATCACGAGACAGGAAAAGTTGTT
ATAAGGTTAATAAGAGTCTCTCCAGGCAGATTTACACTCAAACACTCTAAG
(cont.)
```

FIG. 27 (cont.)

```
TTTAGTTGTAAAAATGGACTATTGACAATAACCTATCCTGAAGGGGAAGTG
AAAGTTACTCCTGGAGAGATAGTTATAGTAGATCCTAGCGTCGATGACATA
GGAATGGAAGGGCATACAATGTGCTCTCAGAAATATCCCAAGGGGAACTC
AAGCATGAAATTTATCAGAAGGTCAAAGCAATATACGAAGGGAACACGGAA
TCAAGATACGAAGTCAACATCTGGAAGAAAAGCACATAGAAGAATTTCTC
TCCAGAGTTAAGAAGATCAACGAAGAACAGAAAAGTTTGCAATTGACATA
ACAACTTTCTAGTCACCCTTCAAGGCCCCCTGGGACTGGGAAGACATCA
GGGGCCATAGCCCCAGCAATTCTCGCAAGAGCATATTCAATGGTGAAGGAC
AAAAAGAATGGCCTCTTTGTAGTTACTGGAGTCTCACACAGGGCAGTTAAT
GAGGCCCTGATAAAGACTTTAAAGCTAAAGAAAGAGCTGGAGAATACATTA
AAAGAGCTTAGAAAGATAGATCTAATTAGAGCAGTCTCTGGGGAAGAGGCA
ATCAAAATAATTAAAGAGGAACTAGAGAGGGAAATAAAGGATGATGTCGAC
AGAATTAGATTTACAGCACAAGAATTACCCACTCTTCAAAGCAAAGATCA
TTAGACAAATATTTTGCTAATTCTGGAACTGTGAGGATAGTATTTGGAACA
CCACAGACTTTGAACAAGCTTATGAAGAATACAAAAGAAGTCGAACTAGTT
GTCATAGATGAAGCTAGTATGATGGACTTACCAATGTTCTTCCTCTCAACA
AAAGTTTGTAAAGGTCAAGTTCTCTTGGTCGGGGATCACAGGCAGATGGAG
CCAATTCAAGTCCATGAATGGCAATTAGAGGACAGAAAGACATTTGAAGAG
CACTATCCATTCCTTTCAGCCCTTAACTTCATTAGATTTCTCAGGGGAGAG
TTGGATGAAAGAGAACTTAAGAAGTTTAAGAGAATCCTTGGAAGGGAACCT
CCAGAATGGAAGAAGGACAAGAACGAGGTTCTCCCTCTCTATAGGTTAGTA
AGAACTTATAGGTTGCCCCAGGAAATAGCTGATCTACTGAGTGATGCAATA
TACAGAGCAGATGGCATAAAATTGATTAGTGAAAAGAAAAAGAGGAGAAAG
ATAATTGCCAGGCACAAGGATGAGTTCTATCGATAGTTTTAGATGACAGG
TATCCTTTCGTTCTAATACTTCATGACGAGGCAATTCCACAAAGATTAAC
GAGCTGGAAGCAAAGATAGTAGAGAAGATAATCAAAAGAGTAGAGAATATT
GATATAGGAGTTGTAGTTCCATATAGAGCTCAAAAGAGATTAATAGCTTCA
TTAATAGATAGTGCCCAGGTGGACACAGTTGAGAGATTCCAAGGGGGAGAG
AAATCTTTAATAGTAATTTCAATGACTTCCAGCGACCCCCGCATACCTGGG
AAAGGTTTTTGA
```

FIG. 28

```
ATGAACATAAAGAGCTTCATAAACAGGCTTAAGGAGCTAGTTGAAATCGAG
AGGGAAGCTGAAATAGAGGCTATGAGGTTGGAGATGAAAAGGCTTAGCGGA
GTGGAGAGGGAGAGGTTAGGTAGGGCAATTCTCAGCTTAAACGGTAAAATC
GTTGGTGAAGAGCTCGGTTATTTCTTGGTTAAGTACGGAAGGAATAAGGAG
ATAAAGACCGAGATCAGCGTTGGGGATTTGGTTGTTATAAGCAAGAGGGAT
CCCCTGAAGAGCGACCTCCTGGGAACTGTTGTTGAGAAGGGGAAGAGATTC
ATCGTCGTTGCCTTAGAACCAGTCCCAGAGTGGGCCCTTAGAGATGTGAGG
ATAGACCTCTACGCCAACGATATAACATTCAAGAGGTGGATCGAAAACCTC
GACAGGGTTAGGAAGGCTGGAAAAAGGCTTTAGAGTTTTACTTAGGTTTA
GATGAGCCTTCCAGGGGGAGGAAGTGAGCTTTGAACCCTTTGATAAGAGC
CTAAACCCCTCTCAAAGGAAAGCGATAGCTAAGGCTTTAGGTAGTGAAGAC
TTCTTCCTTATCCACGGCCCCTTTGGAACTGGAAAGACGAGGACTTTAGTT
GAGCTGATTAGGCAGGAGGTAAAGAGGGGAACAAAGTTCTAGCTACAGCT
GAGAGCAACGTTGCCGTGGACAATTTAGTTGAAAGATTGGCCAAAGATGGA
GTTAAGATAGTTAGGGTTGGGCACCCAAGTAGGGTTTCGAGGCATTTGCAC
GAGACAACTTTAGCTTACCTCATTACTCAGCACGAGCTCTACGGTGAGCTT
AGGGAGCTTAGGGTGATAGGGCAGAGTTTGGCAGAGAAGAGGGACACATAT
ACAAAGCCGACTCCAAAGTTCAGGAGGGGACTGAGTGATGCTGAGATAATT
AAGTTGGCCGAGAAGGGAAGAGGGGCTAGAGGACTCTCAGCTAGACTAATA
AAGGAGATGGCCGAGTGGATAAAGCTAAACAGGCAGGTTCAGAAGGCCTTT
GAAGATGCTAGAAAGCTTGAGGAGAGGATTGCGAGGGATATAATTAGGGAA
GCCGATGTGGTTTTGACAACTAACTCTTCTGCAGCCCTTGATGTTGTTGAT
GCTACCGATTATGATGTTGCGATAATAGATGAAGCAACTCAGGCAACTATA
CCGAGCATATTAATACCTCTCAACAAGGTTGATAGGTTTATACTTGCTGGA
GACCACAAGCAACTACCACCAACTATCTTAAGCTTGGAGGCCCAGGAGCTC
TCCCACACGCTTTTCGAGGGTTTAATTGAGAAGTACCCATGGAAGAGCGAA
ATGCTGACAATTCAGTATAGGATGAATGAGAGGATAATGGAGTTTCCGAGC
AGGGAGTTTTACGATGGAAGAATAGTTGCTGATGAAAGTGTAAAAAACATA
ACTCTGGCCGACCTGGGAATTAAAGTTAATGCTAGTGGAATATGGAGGGAC
ATCCTAGATCCAAACAACGTCCTCGTGTTCATAGATACTTGCATGCTCGAA
AATAGGTTCGAGAGGCAGAGAAGGGGAAGCGAAAGCAGGGAGAATCCCTTG
GAGGCCAAGATAGTGAGCAAAATCGTTGAAAAGCTCTTGGAAAGTGGGGTT
AAAGCGGAAATGATGGGAGTGATTACACCTTACGATGACCAGAGGGATTTG
ATAAGCTTGAATGTTCCCGAAGAAGTTGAGGTCAAGACTGTGGATGGTTAC
CAGGGAAGGGAGAAGGAAGTGATAATTCTATCATTTGTCCGCTCTAACAAA
GCGGGAGAGATCGGCTTTCTCAAGGACTTGAGGAGGCTAAACGTGTCCTTA
ACTAGGGCTAAGAGGAAGCTTATCATGATTGGCGATTCCTCAACGCTTTCA
TCTCACGAAACCTACAGGAGGTTAATCGAGCACGTGAGGGAGAAGGGGTTA
TATGTTGTGCTAACGAAGGATAGCATTTGA
```

FIG. 29

MIEELFKGLESEIVGLHEIPPKRGEYGEFKFRNEEVNELVKRLGFRLYSHQ
VKALEKLYSGKNVVVSTPTASGKSEIFRLFIFDEILSSPSSTFLLIYPTRA
LINNQMEKFEKENTIFEEICGKRVRAEVLTGDTEWEKRREIIRSKPNVIFT
TPDMLHHHILPRWRDYFWLLKGLRLLVVDELHVYRGIFGTNVAYVFKRLFL
RLKRLSSSPQILALSATLRNPKEFAEQFFETEFEEVKEAGSPSPRRIIVMF
EPRRFTGEQLIKQIVERLTRKNIKTLVFFDSRKGTERIMRLFLFSDAFDRI
TTYKGTLTKRERFLIERDFREGNLTVLLTTNALELGIDIGDLDAVINYGIP
SDGLFSLIQRFGRAGRDPNRIAINGIILRRNGLDYYKEHFDELVEGIEKG
LVEKIPVNLDNEKIAKKHLHYAIAELGVVSIKEIEGRWKRFIKTLVEEGYV
EVTRNPITGEEEIRLRRPPVYSSIRTASDESYFLVVDEPWIRGALQRKRGA
ELLRFVNYLKVRGMVVEEVDEIEFHRSLLPGMVYLSRGRPYMAVDKIKIEK
FHFVFARPLPIEEEIDTSSSKIENIEILEVKDEKTVGPIKVKFGRLRVRHE
YTGYAVRGRDVERHVKRLEELKDEGILRGEIDIVPYIWESWKFARVLFDTP
YIREFETEGFWLEFPNDIRIVPEEEFREFFAVASEIDPELAMFLYNRISRK
SLFPTLLGATTHYIRSFILHHAKDKGEEFAFAVKKMIDSKDGIGSGLHAIE
PNIIKLAPVVTHVDSREIGGYSYDDFHGKPVIFIYDGNEGGSGIIRQVYEN
VEKLMYRSLEHIKKCPCKDGCPACIYSPKCGTFNEFLDKWMAIRIWEKVLP

FIG. 30

MLIVVRPGRKKNELEAFIIENPPEKLSQRRNLKADRVVRLIMRDNRLFKAL
EGSQYLNPKEVERALRNSRIVLVNANEWEEYFKKRLMNKRVEKADICRLCL
LNGKITVLTEGNRIRYRDEYICESCAEEELKRELRFRFNSIGMLEQAKKLL
ERFRDLDKVISIFDPSFDPTKHPEITKWDELKAKHIRVEKMHIDELNIPEE
FKVVLKAEGINELLPVQVLAIKNGLLEGENLLVVSATASGKTLIGELAGIP
KALKGKKMLFLVPLVALANQKYEDFKRRYSKLGLKVAIRVGMSRIKTKEEP
IVLDTGTDAHIIVGTYEGIDYLLRAGKKIGNVGTVVIDEIHMLDDEERGAR
LDGLIARLRKLYSNAQFIGLSATVGNPQELARKLGMKLVLYDERPVDLERH
LIIARNESEKWRYIAKLCKAEAMRKSEKGFKGQTIVFTFSRRCHELASFL
TGQGLKAKAYHSGLPYVQRKLTEMEFQAQMIDVVVTTAALGAGVDFPASQV
IFESLAMGNKWITVREFHQMLGRAGRPQYHEKGKVYIIVEPGKKYSAQMEG
TEDEVALKLLTSPIEPVIVEWSDEFEEDNVLAHACVFNRLKVIEEVQSLCL
GANQSAKNVLEKLMEKGLVKIYGDKVEATPYGRAVSMSFLLPREAEFIRDN
LESTDPIEIAIKLLPFENVYLPGSLQREIESAVRGKISSNIFSSSFASVLE
ELDKIIPEISPNAAERLFLIYQDFFNCPEQDCTEFAMERIGRKIIDLRREG
YEPSKISEHFRKVYALILYPGDVFTWLDGIVRKLEAIERIARVFNKRRVVE
DTIRVRREIEEGKILKGERR

FIG. 31

```
MHKYFFPLPATKSTFLLPADLTTANPCFSKSLINSLSAWAPFLYIQCFSYL
PLINFLNSLTYPLEMHILIKKAIKERFGKLNALQQLAFHKIRGEGKSVLII
APTGSGKTEAAVIPILDAILRENLKPIAAIYIAPLKALNRDLLERLKWWEE
KTGVIIEVRHGDTPTSKRLKQVKNPPHLLITTPEMLPAILTTKSFRPYLKN
TKFIVIDEIGELIENKRGTQLILNLKRLELITEDKPIRIGLSATIGSEEKV
RLWMEADEVVKPRLKKKYKFTVLYPQPIPEDEKLAEELKVPIEVATRLRVV
WDIVEKHKKVLIFVNTRQFAEILGHRLKAWGKPVEVHHGSLSREARIEAEK
KLKEGKIKALICTSSMELGIDIGDVDAVIQYMSPRQVNRLVQRAGRSKHRL
WETSEAYIITTNVEDYLQSLAIAKLALEGKLEDVNPYENALDVLAHFIVGL
TIEYRNVNITEPYSLAKSTYPYRKLSWEDYQKVLEILEEARIIRRDGDAIK
LGKNAFKYYFENLSTIPDEISYAVIDIASGKSVGRLDENFVTELEESMEFI
MHGRSWIVLEINEKERIIKVKESNNLESALPSWEGELIPVPLEVAEFVGKL
KRELLWDKERALKLLEGVEFNKEELEVAISQLVESEPVASDRDIIIESYPK
FVIIHADFGNKINEGLTRFISVFLSARYGNIFLPRSQAHGIIIRSPFRLNP
EEIKEILLMKAEVGDIVARGIRDTPIYRWKMSAIAKRFGALRRDARIKKVE
RLFEGTIIEKETFNEIYHDKIDIDKTEKILEKIRKGEIRMKTLFREEITPL
SSSLATLGGEFLIRDILTQEEVEEIFREKLLDAELVMVCTNCGFSWRTKVR
RVMDRVNELSCPKCDSKMIAPLHPKDSETFISALKKLRGEKLSREEEKYY
LRGLKAADLLKAYGKDALLALATYGVGVESATRILRDYRGKSLIKALIEAE
KHYIQTRKFWE
```

FIG. 32

```
VMLLRRDLIQPRIYQEVIYAKCKETNCLIVLPTGLGKTLIAMMIAEYRLTK
YGGKVLMLAPTKPLVLQHAESFRRLFNLPPEKIVALTGEKSPEERSKAWAR
AKVIVATPQTIENDLLAGRISLEDVSLIVFDEAHRAVGNYAYVFIAREYKR
QAKNPLVIGLTASPGSTPEKIMEVINNLGIEHIEYRSENSPDVRPYVKGIR
FEWVRVDLPEIYKEVRKLLREMLRDALKPLAETGLLESSSPDIPKKEVLRA
GQIINEEMAKGNHDLRGLLLYHAMALKLHHAIELLETQGLSALRAYIKKLY
EEAKAGSTKASKEIFSDKRMKKAISLLVQAKEIGLDHPKMDKLKEIIREQL
QRKQNSKIIVFTNYRETAKKIVNELVKDGIKAKRFVGQASKENDRGLSQRE
QKLILDEFARGEFNVLVATSVGEEGLDVPEVDLVVFYEPVPSAIRSIQRRG
RTGRHMPGRVIILMAKGTRDEAYYWSSRQKEKIMQETIAKVSQAIKKQKQT
SLVDFVREKESEKTSLDKWLKKEKEEATEKEEKKVKAQEGVKVVVDSRELR
SEVVKRLKLLGVKLEVKTLDVGDYIISEDVAIERKSANDFIQSIIDGRLFD
QVKRLKEAYSRPIMIVEGSLYGIRNVHPNAIRGAIAAVTVDFGVPIIFSST
PEETAQYIFLIAKREQEEREKPVRIRSEKKALTLAERQRLIVEGLPHVSAT
LARRLLKHFGSVERVFTASVAELMKVEGIGEKIAKEIRRVITAPYIEDEE
```

FIG. 33

```
LKGLFRDVILHNPHLFVYSYSDKGIIPFKHQFQTLYHAMLMRPVRLMIADE
IGLGKTIQALLIAKYLDFRGEIEKALIVVPKVLREQWREEVKRILEEAPEV
IENGSEIEWKLKRPRKYFIISIDLAKRYTEEILRQKWDLVIVDEVHNATLG
TQRYEFLKELTKNKDLNVIFLSATPHRGNNRDYLARLRLLDPTIPEEISPM
HERKIYMKSRGTLVLRRTKKVVNELEGEVFKKCHFGAVVVEVSREEREFFE
ELNRALFELIKDQADYSPLTLLAVIIRKRASSSYEAALKTLTRIVESAYIS
GQERARGVESYIEKIFRMGYEELEIEEFNEIDDAIHKIIDEYRGFLTEEQL
ERLRRVLELGKKIGSKDSKLEVISDIVAYHIRNGEKVIIFTEFRDTLEYVL
ERLPDILRRKHGIVLEKDDIAKLHGGMKSEEIEREINKFHERANLLVSTDV
ASEGLNLHVASVVINYEAPWSPIKLEQRVGRIWRLNQTRETKAYTIFLATE
TDLDVLNNLYRKIMNIKEAVGSGPIIGRPIFEGDFENLWNEGAEEENREVS
EYELILASIKGELKGYAGALVRTLRILKQKVEGAVPVNPAGSIRRELEIIL
EDTPDVEVLKKIVNRNVPNPFRLVRGLLREAEGIEGIRVLVKGYDGSMDVY
YAIFYDEDGREIYRYPILAENGKYLVGFNLLKRISEVLSKEYKVVRGASEE
VDYKVKTLVMDNIYNLIVKKYLEYDSLNIKEGKIFKRLKVEIKKALEVKGI
SEEEFEVIKRVPPEIMEVLGLDSTKIELPTNEYLKIFERNFVPLDKILESE
KKAMEIVMELEKSRGYNVEDVSLREHYDIRAFTDGEEKYIEVKGHYPMLLL
AELTEKEFEFAQKNEDKYWIYIVSNIAKDPVIVKIYKPFSQDRRVFVVKNG
EDVEVNINIEIKKKDRHLLKLS
```

FIG. 34

VITLELHPSEIARYFELEECSHYFSNLLLRKRGELQEFEPIIRRKEIETIE
LAKWGDEFELSLLQEFKKGEALKKLGVKELPRFYGFLTENDTPVRKFFEKY
FKDGIIVEEDPDKLLEIINSEKSAVIYQAPLKGRIGKFDVSGRADFIIKVG
KTLYLLEAKFTKEEKFYHRIQAIIYAHLLSQMIEGYEIKLAVVTKENFPIP
SNFLRFPGDVEELKITLEEKLGGILREQELWIDARCTTCPFEALCLSKALE
ERSLGLLSLPPGIIRILKEEGIKDLKDMAKLFEFKENSPTNFEEPSIKDPK
KTQEIAKRTGINLLKLSRIAQAILKYLDEGETTPLFIPRTGYNLPMDERVG
DVEPSYYPPRSLVKVFFYVQTSPITDTIIGISALVKNRQNGERIIVKFVDE
PPIEVSDAQEKERMLLIEFFRDVIDAVKSLSPTDKVYLHMYFYNRKQRDDL
MDAVKRHKEIRENNAVMALLSLRRAIDWESFSIIKDEIIRRHALPLSPGLG
FVTVATQFGYRWRRNKTFARMLEVVARRENGKINLKTLLNISETGIGPEYY
PIIDRDNEGIPFTLFWSALVKLATEEDNSRIKRDIRDILSQMVEALKTIEE
RIPEQYKDAFVKKEGIPKEDLENFDIKKEELADILLEYLQLEFDARFRERS
EYYRLPLSIRAYSEESALIKIENIEKKKNDCLLFGKIVLIDENGRIKEYNP
KEVLIDIDEGSLVVVTPKKFLDKLRRDPVQRISKSPLGIVEAIDHETGKVV
IRLIRVSPGRFTLKHSKFSCKNGLLTITYPEGEVKVTPGEIVIVDPSVDDI
GMERAYNVLSEISQGELKHEIYQKVKAIYEGNTESRYEVNIWKKKHIEEFL
SRVKKINEEQKKFAIDINNFLVTLQGPPGTGKTSGAIAPAILARAYSMVKD
KKNGLFVVTGVSHRAVNEALIKTLKLKKELENTLKELRKIDLIRAVSGEEA
IKIIKEELEREIKDDVDRIRFTAQEITHSSKQRSLDKYFANSGTVRIVFGT
PQTLNKLMKNTKEVELVVIDEASMMDLPMFFLSTKVCKGQVLLVGDHRQME
PIQVHEWQLEDRKTFEEHYPFLSALNFIRFLRGELDERELKKFKRILGREP
PEWKKDKNEVLPLYRLVRTYRLPQEIADLLSDAIYRADGIKLISEKKKRRK
IIARHKDEFLSIVLDDRYPFVLILHDEGNSTKINELEAKIVEKIIKRVENI
DIGVVVPYRAQKRLIASLIDSAQVDTVERFQGGEKSLIVISMTSSDPRIPG
KGF

FIG. 35

MNIKSFINRLKELVEIEREAEIEAMRLEMKRLSGVERERLGRAILSLNGKI
VGEELGYFLVKYGRNKEIKTEISVGDLVVISKRDPLKSDLLGTVVEKGKRF
IVVALEPVPEWALRDVRIDLYANDITFKRWIENLDRVRKAGKKALEFYLGL
DEPSQGEEVSFEPFDKSLNPSQRKAIAKALGSEDFFLIHGPFGTGKTRTLV
ELIRQEVKRGNKVLATAESNVAVDNLVERLAKDGVKIVRVGHPSRVSRHLH
ETTLAYLITQHELYGELRELRVIGQSLAEKRDTYTKPTPKFRRGLSDAEII
KLAEKGRGARGLSARLIKEMAEWIKLNRQVQKAFEDARKLEERIARDIIRE
ADVVLTTNSSAALDVVDATDYDVAIIDEATQATIPSILIPLNKVDRFILAG
DHKQLPPTILSLEAQELSHTLFEGLIEKYPWKSEMLTIQYRMNERIMEFPS
REFYDGRIVADESVKNITLADLGIKVNASGIWRDILDPNNVLVFIDTCMLE
NRFERQRRGSESRENPLEAKIVSKIVEKLLESGVKAEMMGVITPYDDQRDL
ISLNVPEEVEVKTVDGYQGREKEVIILSFVRSNKAGEIGFLKDLRRLNVSL
TRAKRKLIMIGDSSTLSSHETYRRLIEHVREKGLYVVLTKDSI

ATPase ASSAY FROM PHAGE INDUCED HELICASES
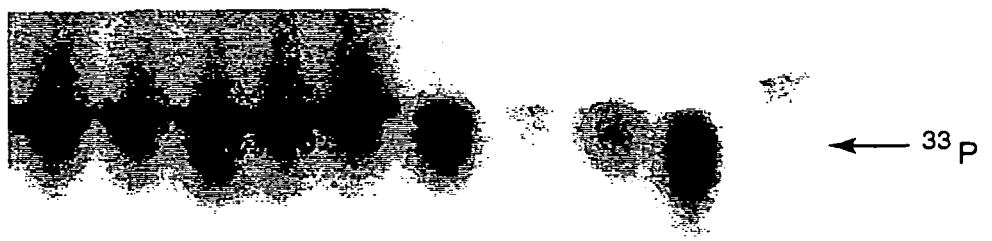
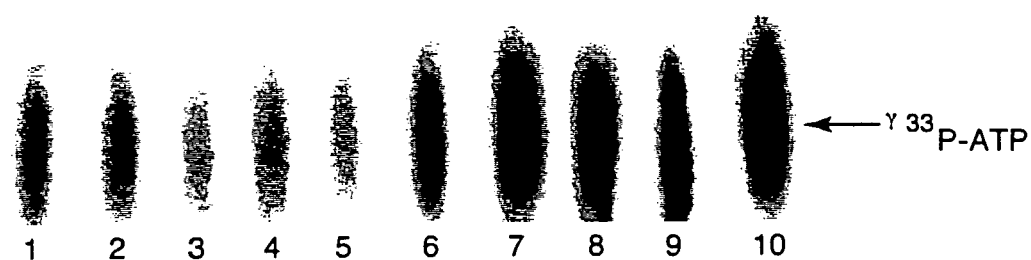
FIG. 36
ATPase ASSAY FROM IPTG INDUCED HELICASES
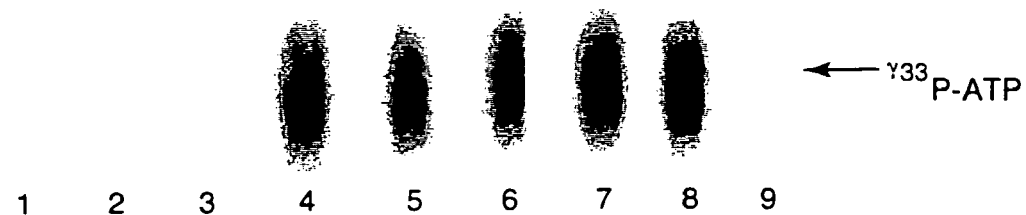
FIG. 37

FIG. 40

```
ATGAGGGTTGATGAGCTGAGAGTTGATGAGAGGATAAAGAGTACTTTGAAG
GAGAGAGGTATCGAATCCTTTTACCCTCCCCAAGCCGAGGCCTTAAAGAGC
GGGATATTGGAAGGTAAGAATGCATTAATTTCAATTCCAACGGCCAGCGGA
AAAACACTAATTGCTGAGATTGCCATGGTTCATAGGATTTTGACCCAGGGA
GGAAAGGCTGTATACATAGTCCCGCTGAAGGCCTTGGCTGAAGAAAGTTT
CAGGAGTTCCAGGATTGGGAGAAGATTGGGTTAAGAGTAGCGATGGCCACT
GGGGATTACGACTCAAGGATGAGTGGTTGGGGAAATACGACATAATCATT
GCGACGGCTGAGAAGTTTGATTCCCTTTTAAGGCATGGCTCAAGTTGGATT
AAGGATGTGAAGATTTTAGTTGCTGACGAGATTCATTTGATTGGTTCAAGA
GACAGAGGAGCTACGCTTGAAGTTATCCTAGCTCATATGCTCGGAAAGGCC
CAAATAATTGGACTCTCTGCAACGATAGGAAATCCAGAGGAGCTTGCGGAG
TGGTTAAATGCCGAGCTAATAGTCAGTGACTGGAGGCCCGTTAAGCTTAGA
AGGGGAGTTTTTTACCAAGGCTTTGTTACCTGGGAAGATGGAAGTATAGAC
AGGTTTTCCTCCTGGGAAGAGTTAGTTTACGATGCAATTAGGAAGAAGAAA
GGAGCGCTAATTTTTGTAAACATGAGAAGGAAGGCTGAGAGAGTAGCTTTG
GAGCTTTCTAAAAAGTTAAGTCTCTCCTCACGAAACCTGAGATTAGAGCT
TTAAATGAATTGGCTGATTCCCTCGAGGAAAATCCACAAATGAAAAGCTA
GCTAAGGCCATTAGGGGTGGAGTTGCGTTCCACCACGCTGGTCTTGGGAGA
GATGAGAGGGTTCTCGTGGAGGAGAACTTTAGAAAGGGTATAATAAAGGCC
GTAGTTGCCACCCCAACACTTTCGGCGGGAATTAACACTCCAGCGTTTAGG
GTGATTATAAGGGATATTTGGAGGTACTCTGACTTTGGAATGGAGAGAATT
CCGATAATCGAGGTTCACCAAATGCTTGGGAGAGCTGGAAGGCCGAAGTAT
GATGAGGTTGGGGAGGGAATAATAGTTTCTACAAGCGATGATCCGAGAGAG
GTAATGAATCACTACATATTTGGAAAGCCTGAAAAACTGTTCTCCCAGCTC
TCCAACGAGAGTAATTTGAGAAGTCAAGTTTTGGCCCTAATAGCGACCTTT
GGCTATTCAACTGTGGAGGAGATTTTGAAGTTCATCTCAAACACATTCTAT
GCTTATCAAAGGAAGGACACATACTCTTTAGAGGAGAAGATAAGGAACATA
CTCTACTTCCTCCTAGAGAATGAGTTCATAGAGATATCCTTAGAGGATAAA
ATAAGGCCGCTTTCCCTGGGAATTAGGACTGCAAAGCTTTATATCGATCCC
TATACGGCCAAGATGTTCAAGGATAAAATGGAGGAAGTTGTTAAAGATCCA
AATCCTATAGGAATATTTCACTTAATCTCCCTAACTCCGGATATAACCCCC
TTCAACTACTCAAAGAGAGAATTTGAAAGGCTCGAAGAGGAATACTACGAA
TTCAAGGATAGGTTATACTTTGACGATCCCTACATTTCGGGTTACGACCCC
TACCTAGAGAGGAAGTTCTTCAGAGCTTTCAAAACTGCACTAGTGCTTCTG
GCATGGATAAATGAAGTCCCTGAGGGAGAAATAGTTGAAAGTACTCGGTG
GAACCTGGGGACATCTATAGGATAGTTGAGACGGCTGAGTGGCTGGTGTAC
TCTCTAAAGGAAATTGCAAAGTTCTTGGAGCTTATGAGATCGTTGATTAT
CTTGAAACATTGAGGGTTAGGGTCAAGTATGGATTAGGGAGGAATTGATT
CCCCTAATGCAACTCCCGTTGGTTGGAAGAAGGAGAGCTAGAGCTCTTTAC
AATAGCGGATTTAGAAGTATAGAGGATATATCTCAAGCGAGGCCAGAAGAG
CTTTTGAAAATCGAGGGGATAGGGGTCAAGACCGTTGAGGCTATCTTCAAG
TTTCTTGGTAAGAATGTGAAAATTTCGGAGAAACCTAGAAAAAGTACCCTT
GATTACTTTCTCAAATCTTGA
```

FIG. 41

MRVDELRVDERIKSTLKERGIESFYPPQAEALKSGILEGKNALISIPTASG
KTLIAEIAMVHRILTQGGKAVYIVPLKALAEEKFQEFQDWEKIGLRVAMAT
GDYDSKDEWLGKYDIIIATAEKFDSLLRHGSSWIKDVKILVADEIHLIGSR
DRGATLEVILAHMLGKAQIIGLSATIGNPEELAEWLNAELIVSDWRPVKLR
RGVFYQGFVTWEDGSIDRFSSWEELVYDAIRKKKGALIFVNMRRKAERVAL
ELSKKVKSLLTKPEIRALNELADSLEENPTNEKLAKAIRGGVAFHHAGLGR
DERVLVEENFRKGIIKAVVATPTLSAGINTPAFRVIIRDIWRYSDFGMERI
PIIEVHQMLGRAGRPKYDEVGEGIIVSTSDDPREVMNHYIFGKPEKLFSQL
SNESNLRSQVLALIATFGYSTVEEILKFISNTFYAYQRKDTYSLEEKIRNI
LYFLLENEFIEISLEDKIRPLSLGIRTAKLYIDPYTAKMFKDKMEEVVKDP
NPIGIFHLISLTPDITPFNYSKREFERLEEEYYEFKDRLYFDDPYISGYDP
YLERKFFRAFKTALVLLAWINEVPEGEIVEKYSVEPGDIYRIVETAEWLVY
SLKEIAKVLGAYEIVDYLETLRVRVKYGIREELIPLMQLPLVGRRRARALY
NSGFRSIEDISQARPEELLKIEGIGVKTVEAIFKFLGKNVKISEKPRKSTL
DYFLKS

PFU REPLICATION ACCESSORY FACTORS AND METHODS OF USE

RELATED APPLICATION INFORMATION

This application is a continuation of U.S. application Ser. No. 09/626,813, filed Jul. 27, 2000 now abandoned, which claims the benefit of U.S. Provisional Application No. 60/146,580, filed Jul. 30, 1999. U.S. application Ser. No. 09/626,813 and U.S. Provisional Application No. 60/146,580 are incorporated by reference herein.

BACKGROUND AND SUMMARY OF THE INVENTION

The invention relates to the field of replicating, amplifying, and sequencing nucleic acids. Further, this invention relates to novel proteins that enhance the activity of the polymerases.

In vitro polymerization techniques have enormously benefited the fields of biotechnology and medicine. The ability to manipulate nucleic acids with polymerization reactions greatly facilitates techniques ranging from gene characterization and molecular cloning (including, but not limited to sequencing, mutagenesis, synthesis and amplification of DNA), determining allelic variations, and detecting and screening of various diseases and conditions (e.g., hepatitis B).

An in vitro polymerization technique of great interest is the polymerase chain reaction (PCR). This method rapidly and exponentially replicates and amplifies nucleic acids of interest. PCR is performed by repeated cycles of denaturing a DNA template, usually by high temperatures, then annealing opposing primers to the complementary DNA strands, and then extending the annealed primers with a DNA polymerase. Multiple cycles of PCR result in an exponential amplification of the DNA template.

Unfortunately, PCR has limitations. These limitations range from 1) the rate of nucleotide incorporation, 2) the fidelity of nucleotide incorporation, 3) the length of the molecule to be amplified, and 4) the specificity of the polymerase.

Various methods to improve PCR exist. One approach is to optimize the reaction conditions, e.g., such as the pH, dNTP concentrations, or reaction temperatures. Another approach is to add various chemical compounds, e.g., formamide (Sarkar, G., et al. Nucl. Acids Res. 18: 7465 (1990)), tetramethyammonium chloride, and dimethyl sulfoxide (Chevet et al., Nucl. Acids Res. 23:3343-3344 (1995); Hung et al., Nucl. Acids Res. 18:4953 (1990)) to either increase the specificity of the PCR reaction and/or increase yield. Other attempts include adding various proteins, such as replication accessory factors. Replication accessory factors known to be involved in DNA replication have also increased yields and the specificity of PCR products. For example, E. coli single-stranded DNA binding protein, such as RFA, has been used to increase the yield and specificity of primer extension reactions and PCR reactions (U.S. Pat. Nos. 5,449,603, and 5.534,407). Another protein, the gene 32 protein of phage T4, appears to improve the ability to amplify larger DNA fragments (Schwartz et al., Nucl. Acids Res. 18: 1079 (1990).

An important modification that has enhanced the ease and specificity of PCR is the use of *Thermus aquaticus* (Taq) DNA polymerase in place of the Klenow fragment of *E. coli* DNA pol I (Saiki et al., Science 230: 1350-1354 (1988)). The use of this thermostable DNA polymerase obviates the need for repeated enzyme additions, permits elevated annealing and primer extension temperatures, and enhances specificity. Further, this modification has enhanced the specificity of binding between the primer and its template. But, Taq polymerase has a fundamental drawback because it does not have 3' to 5' exonuclease activity and, therefore, cannot excise incorrect nucleotides added to the ends of the amplified products. Due to this limitation, the fidelity of Taq-PCR reactions typically have suffered. Therefore, those in the field have searched for another thermostable polymerase that has 3' to 5' exonuclease activity.

Polymerases having 3' to 5' exonuclease activity have been found in archaebacteria (archaea). Archaebacteria is a third kingdom, different from eukaryotes and bacteria (eubacteria). Many archaebacteria are thermophilic bacteria-like organisms that can grow in extremely high temperatures, i.e., 100° C. One such archaebacteria is *Pyrococcus furiosus* (Pfu). A monomeric polymerase from Pfu has been identified that has the desired 3' to 5' exonuclease activity and synthesizes nucleic acids of interest at high temperatures (Lundberg et al., Gene 108: 1-6 (1991); Cline et al., Nucl. Acids Res. 24: 3546-3551 (1996) (This polymerase is referred to as Pfu polymerase.)) A second DNA polymerase has been identified in *P. furiosus* which has two subunits (DP1/DP2) and is referred to as pol II. See References 1 and 15. This polymerase may also be enhanced by the accessory factors.

Certain natural proteins exist in archaebacteria, i.e., PEF (polymerase enhancing factors) that exhibit deoxyuracil triphosphatase (dUTPase) activity and that enhance the activity of Pfu polymerase (International Patent Application Publication No. WO 98/42860, published on Oct. 1, 1998). The presence of deoxyuracil-containing DNA in a DNA polymerization reaction inhibits polymerase activity (Lasken et al. (J. Biol. Chem. 271: 17692-17696)). Specifically, during the course of a normal PCR reaction, a dCTP may be deaminated into dUTP, thereby introducing a deoxyuridine into the newly synthesized DNA. But, when this newly synthesized DNA is thereafter amplified, the presence of the deoxyuridine inhibits the Pfu polymerase. The archaeal dUTPase (PEF) prevents dUTP incorporation and, thus, avoids the inhibition of the Pfu polymerase. Accordingly, the archaeal dUTPase optimizes the activity of Pfu polymerase.

According to certain embodiments, the invention provides methods of, and materials for, enhancing the polymerase activity of Pfu polymerase. Certain embodiments involve major components of the replication machinery in eukaryotes, e.g.: a helicase enzyme that unwinds the DNA helix and, thereby, provides a single-stranded DNA template; single-stranded DNA binding proteins (RFA) that bind and stabilize the resulting single-stranded DNA template; a "sliding clamp" protein (PCNA) that stabilizes the interaction between the polymerase and the primed single-stranded DNA template and that enhances synthesis of long DNA strands (also known as "processivity"); and a "clamp-loading" protein complex (RFC) that assembles the PCNA protein.

According to certain embodiments, the invention provides novel DNA replication accessory factors which have been isolated and purified from the hyperthermophilic archaeal bacteria *Pyrococcus furiosus*. In certain embodiments, the isolated proteins are thermostable homologues of eukaryotic DNA replication proteins PCNA, RF-C subunits, RFA, and helicases. Recent computer analysis of sequence data do not describe the proteins disclosed herein, although sequences that may be homologous to eukaryotic and/or eubacterial replication factors exist (Chedin et al., TIBS 23:273-277 (1998); Egdell and Doolittle, Cell 89: 995-998 (1997); Bult et al., Science 273: 1058-1-73 (1996)).

According to certain embodiments, this invention also involves isolated polynucleotides that encode the replication accessory factors.

In certain embodiments, the polynucleotide may be cDNA, genomic DNA, mRNA, or plasmid DNA.

According to certain embodiments, the invention includes vectors comprising a polynucleotide that encodes a replication accessory factor and host cells comprising such vectors. According to certain embodiments, the invention includes polypeptides expressed in those host cells. Further, this invention provides not only the host cells and their products, but also, the methods of using such host cells to produce the polypeptides of interest.

According to certain embodiments, the invention includes methods of enhancing a nucleic acid polymerase reaction comprising the addition of one or more of the replication accessory factors to the reaction.

In certain embodiments, only one archaeal replication accessory factor will be added into the nucleic acid polymerase reaction. In other embodiments, a combination of factors may be added.

In certain embodiments, an archaeal dUTPase may be combined with one or more of those replication accessory factors to further enhance the polymerase In certain embodiments, this invention also provides methods of synthesizing nucleic acids comprising employing an archaeal polymerase and an archaeal replication accessory factor(s).

According to certain embodiments, the invention includes methods of amplifying nucleic acids of interest comprising employing an archaeal polymerase and an archaeal replication accessory factor(s).

In certain embodiments of the inventive methods, the archaeal polymerase is Pfu polymerase. In certain embodiments of those methods, the archaeal polymerase is combined with another polymerase, such as Taq. In other embodiments of the these methods, an archaeal dUTPase may also be included to enhance polymerase activity.

In certain embodiments of the inventive methods, the archaeal polymerase is *P. furiosus* pol II polymerase.

In certain embodiments, this invention also provides a kit used in the practice of the above-described methods.

In certain embodiments, this invention also provides a kit comprising an archaeal polymerase and at least one archaeal replication accessory factor.

In certain embodiments, those kits would also comprise an archaeal dUTPase and possibly, another polymerase, such as Taq.

BRIEF DESCRIPTION OF THE DRAWINGS

The abbreviations used herein for amino acids in the translated protein sequences, which are single letter, and the nucleic acids are those it conventionally used, as in Stryer et al., *Biochemistry*, 3rd ed., W. H. Freeman, N.Y. (1988) at the back cover.

FIG. 3 illustrates the DNA sequence of PCNA. (SEQ ID NO: 59).

FIG. 4 illustrates the translated protein sequence of PCNA. (SEQ ID NO: 60).

FIG. 8 illustrates the DNA sequence of genomic RFC clones. (SEQ ID NO: 61). Genomic sequences encoding the P38 and P55 subunits are located in tandem, respectively. The sequence encoding P38 contains an intein. As used herein, the term "intein" includes, but is not limited to protein splicing elements. These elements are involved in the post-translational processing of pre-proteins. The coding regions of the P38 and P55 subunits are bracketed [ ]. The intein sequence is enclosed in parentheses ( ).

FIG. 9 illustrates the translated protein sequence of the genomic RFC clone. (SEQ ID NO: 62). The sequence encoding P38 and P55, respectively, are enclosed in parentheses ( ), while the sequence of the intein is bracketed [ ]. The * indicates a stop codon.

FIG. 10 illustrates the translated protein sequence of recombinant P55 clone. (SEQ ID NO: 63).

FIG. 11 illustrates the translated protein sequence of recombinant P38 clone. (SEQ ID NO: 64).

FIG. 16 illustrates a cDNA sequence of a clone expressing RFA. (SEQ ID NO: 65).

FIG. 17 illustrates the translated protein sequence of RFA. (SEQ ID NO: 66). The theoretical molecular weight is 41.3 kDa. The native protein may start at the third methionine.

FIG. 22 illustrates the DNA sequence of recombinant helicase 2. (SEQ ID NO: 67). This helicase has demonstrated PCR enhancing activity.

FIG. 23 illustrates the DNA sequence of recombinant helicase 3. (SEQ ID NO: 68).

FIG. 24 illustrates the DNA sequence of recombinant helicase 4. (SEQ ID NO: 69).

FIG. 25 illustrates the DNA sequence of recombinant helicase 5. (SEQ ID NO: 70).

FIG. 26 illustrates the DNA sequence of recombinant helicase 6. (SEQ ID NO: 71).

FIG. 27 illustrates the DNA sequence of recombinant helicase 7. (SEQ ID NO: 72).

FIG. 28 illustrates the DNA sequence of recombinant helicase dna2. (SEQ ID NO: 73). This helicase has demonstrated PCR enhancing activity.

FIG. 29 illustrates the translated protein sequence for helicase 2. (SEQ ID NO: 74). The theoretical molecular weight is 87.9 kDa+4.0 kDa (CBP affinity tag).

FIG. 30 illustrates the translated protein sequence for helicase 3. (SEQ ID NO: 75). The theoretical molecular weight is 100.0 kDa+4.0 kDa.

FIG. 31 illustrates the translated protein sequence for helicase 4. (SEQ ID NO: 76). The theoretical molecular weight is 105.0 kDa+4.0 kDa.

FIG. 32 illustrates the translated protein sequence for helicase 5. (SEQ ID NO: 77). The theoretical molecular weight is 86.8 kDa+4.0 kDa.

FIG. 33 illustrates the translated protein sequence for helicase 6+4.0 kDa (CBP affinity tag). (SEQ ID NO: 78).

FIG. 34 illustrates the translated protein sequence for helicase 7. (SEQ ID NO: 79). The theoretical molecular weight is 126.0 kDa+4.0 kDa.

FIG. 35 illustrates the translated protein sequence for helicase dna2+4.0 kDa (CBP affinity tag). (SEQ ID NO: 80).

FIG. 36 illustrates the ATPase activity of helicases produced by phage induction. 1 microliter of Pfu helicases 3, 4, 5, 6, 7, and 8 (lanes 1-6 respectively), 0.8 units of porcine ATPase (9) or water (10) were incubated with 1 μl of 4.5 micromolar ATP and 1 microCurie of gamma labeled $^{33}P$ ATP in 1×Optiprime buffer #3 (10 mM Tris-HCl (pH 8.3), 3.5 mM $MgCl_2$, 75 mM KCl). The samples were incubated at 72° C. for 20 minutes before being spotted on PEI cellulose F. The samples were allowed to dry before the PEI cellulose was placed in a shallow reservoir of 0.4 M $NaH_2PO_4$. The liquid front was allowed to migrate 5 cm before being removed from the liquid and dried. The samples were exposed to x-ray film for one hour.

FIG. 37 illustrates the ATPase activity of helicases produced by IPTG induction of bacterial cultures. 1 microliter of an old lot or new lot of Pfu dna2-like helicase (lanes 1 and 2, respectively), Pfu helicase 2, 3, 4, 5 and 7 (lanes 3-7), water (8), or 0.8 units of porcine ATPase (9) were incubated with 1 μl of 4.5 micromolar ATP and 1 microCurie of gamma labeled $^{33}P$ ATP in 1×Optiprime buffer #3 (10 mM Tris-HCl (pH 8.3), 3.5 mM $MgCl_2$, 75 mM KCl). The samples were incubated at 72° C. for 20 minutes before being spotted on PEI cellulose F. After drying, the PEI cellulose was placed in a shallow reservoir of 0.4 M $NaH_2PO_4$. The liquid front was allowed to migrate 4 cm before being removed from the liquid and dried. The samples were exposed to x-ray film for one hour.

FIG. 40 illustrates the DNA sequence of recombinant helicase 8. (SEQ ID NO: 81). Molecular weight is 82.6 kD+4 kDa CBP tag.

FIG. 41 illustrates the translated protein sequence of recombinant helicase 8. (SEQ ID NO: 82).

DETAILED DESCRIPTION OF EMBODIMENTS OF THE INVENTION

Figure 1:
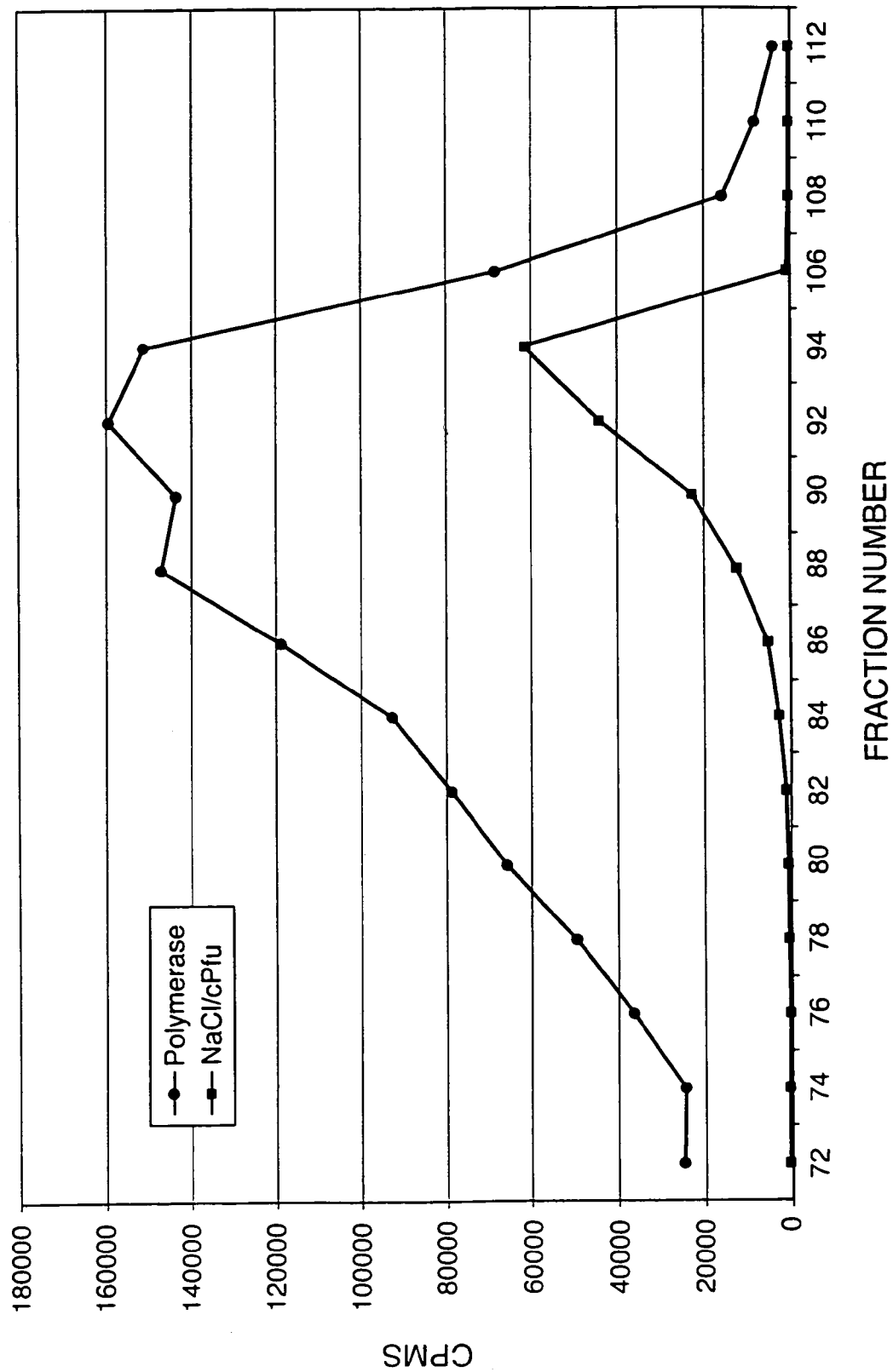
FIG. 1 illustrates the identification of native PCNA in heparin sepharose fractions. Nucleotide incorporation was measured in the absence of salt to detect polymerase activity ("Pol") or in the presence of NaCl+Pfu DNA polymerase to detect PCNA.

The invention provides for isolated and purified polynucleotides that encode novel DNA replication accessory factors from hyperthermophilic archaebacteria. In certain embodiments, the replication accessory factors are from *Pyrococcus furiosus*. These replication accessory factors may be thermostable homologues of the eukaryotic DNA replication proteins PCNA, RFC subunits, RFA, and helicases.

As used herein "isolated and purified polynucleotide" is a nucleic acid, which is substantially separate from at least one other DNA sequence that naturally accompanies the native polynucleotide. Such other DNA sequences may be, e.g., a ribosome, a polymerase, and any other human genomic sequence.

These polynucleotides include RNA, cDNA, genomic DNA, synthetic forms, e.g., oligonucleotides, antisense and sense strands, and may also include chemically or biochemically modified nucleotides, e.g., mutated nucleotides or cys-labeled nucleotides. Recombinant polynucleotides comprising the sequences otherwise not naturally occurring are also provided in this invention.

Although polynucleotides having naturally occurring sequences may be employed, such polynucleotides may be altered, e.g., by deletion, substitution, or insertion. One skilled in the art will know appropriate changes in the sequence that will encode proteins that retain biological activity. In certain preferred embodiments, polynucleotides may be changed to encode different conservative amino acid substitutions. Conservative amino acid substitutions include, but are not limited to, a change in which a given amino acid may be replaced, for example, by a residue having similar physiochemical characteristics. Examples of such conservative substitutions include, but are not limited to, substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known. See Biochemistry: A Problems Approach, (Wood, W. B., Wilson, J. H., Benbow, R. M., and Hood, L. E., eds.) Benjamin/Cummings Publishing Co., Inc., Menlo Park, Calif. (1981), page 14-15.

cDNA or genomic libraries of various types may be screened as natural sources of the polynucleotides of the present invention, or such nucleic acids may be provided by amplification of sequences that exist in genomic DNA or other natural sources, e.g., by PCR. See, e.g., *PCR Protocols: A Guide to Methods and Application*, Innis, M., et al., eds., Academic Press: San Diego (1990). Genomic polynucleotides encoding the archaeal replication accessory factors may contain additional non-coding bases, or inteins, and one skilled in the art would know how to obtain such polynucleotides. One way to obtain genomic DNA sequences is by probing a genomic library with all or part of a known DNA sequence. The obtained genomic DNA sequence should encode functional proteins.

In certain embodiments of this invention, the nucleic acid sequences of the isolated polynucleotides encoding the replication accessory factors have been obtained and may be used for various purposes. In certain embodiments, the invention includes isolated and purified polynucleotides that encode the following: an archaeal PCNA, an archaeal RFC subunit P38 protein, archaeal RFC subunit P55, archaeal RFC subunit P98, archaeal RFA, and various archaeal helicases. According to certain embodiments, the invention includes eight different helicases that exist in Pfu, i.e., helicase 2 to 8, and helicase dna2. According to certain embodiments, the polynucleotide sequences are set forth in FIGS. 3, 8, 16, 23 to 28, and 40.

As used herein, the term "PCNA" may also be referred to as a "clamp" or a "sliding clamp" protein, in view of its role in clamping the DNA polymerase to the DNA template in eukaryotes.

In certain embodiments, the term "RFC subunits" includes, but is not limited to, proteins of about 55 kDa and about 38 kDa in molecular weight or subunits having the amino acid sequence set forth in FIG. 10 and FIG. 11, respectively. These subunits are referred to herein as "P55" and "P38." These subunits are part of a complex having one large subunit and at least one small subunit. P55 is considered a large subunit and P38 a small subunit.

This invention further provides for isolated and purified polynucleotides that encode amino acid sequences for various replication accessory factors, such as an archaeal PCNA, archaeal-RFC subunit P38 protein, archaeal RFC subunit P55, archaeal RFA, and various archaeal helicases. According to certain embodiments, the amino acids sequences of those polynucleotides are set forth in FIGS. 4, 9 to 11, 17, 29 to 35, and 41.

These polynucleotides described herein also include nucleic acid sequences that encode for polypeptide analogs or derivatives of the various archaeal replication accessory factors, which differ from naturally-occurring forms, e.g., deletion analogs that contain less than all of the amino acids of the naturally-occurring forms, substitution analogs that, have one or more amino acids replaced by other residues, and addition analogs that have one or more amino acids added to the naturally-occurring sequence. These various analogs share some or all of the biological properties of the archaeal replication accessory factors. As noted above, one skilled in the art will be able to design suitable analogs. In certain preferred embodiments, conservative amino acid substitutions will be made. In certain embodiments, the analogs will be 70%, 75%, 80%, 85%, 90%, 95%, or 99% identical to the naturally-occurring sequence.

Percent identity involves the relatedness between amino acid or nucleic acid sequences. One determines the percent of identical matches between two or more sequences with gap alignments that are addressed by a particular method. The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

In certain embodiments, nucleic acids may be those that hybridize under moderately or highly stringent conditions to the complement of naturally-occurring encoding nucleic acids or to nucleic acids that encode proteins having naturally-occurring amino acid sequences. As used herein, conditions of moderate stringency can be readily determined by those having ordinary skill in the art based on, for example, the length of the DNA. The basic conditions are set forth by Sambrook et al. *Molecular Cloning: A Laboratory Manual*, 2 ed. Vol. 1, pp.1.101-104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5× SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

In certain embodiments, polynucleotides may have sequences different from the naturally-occurring nucleic acid sequence in view of the redundancy in the genetic code, especially if the amino acid sequences are known. Various codon substitutions may be introduced to produce various restriction sites or to optimize expression in a particular system.

The polynucleotides used in this invention will usually comprise at least about 15 nucleotides. In certain embodiments, the number of nucleotides is the minimal length required to express a biologically active replication accessory factor or, to probe for nucleic acid sequences encoding a replication accessory factor, or for nucleic acid priming.

Techniques for manipulating polynucleotides are described generally in Sambrook et al., *Molecular Cloning: A Laboratory Manual*, 2nd edition, eds. Sambrook et al. (Cold Spring Harbor Laboratory Press 1989)). Reagents useful in applying such techniques, e.g., restriction enzymes, are widely known in the art and commercially available from vendors such as Stratagene These polynucleotides may be used as nucleic acid probes and primers. Such probes and primers would be useful in screening for other archaeal replication accessory factors or screening other species for homologous replication accessory factors. The probe or primer may comprise an isolated nucleic acid, and may include a detectable label, such as a reporter molecule.

In certain embodiments of this invention, one may also want to generate viral or plasmid DNA vectors using the polynucleotides disclosed herein. The contemplated vectors include various viral vectors. Some commonly used examples are, but are not limited to, plasmids, bacteriophages, retroviruses, and adenovirus. Such vectors may be coupled with nucleic acids that encode an origin of replication (ORI) or autonomously replicating sequence (ARS), expression control sequences, e.g., promoter and enhancer sequences, and protein processing information sites, such as RNA splice sites, polyadenylation sites, ribosome-bind sites, and mRNA stabilizing sequences. Such vectors and the methods used in constructing them are well known in the art. See, e.g., Sambrook et al. *Molecular Cloning: A Laboratory Manual*, 2 ed. Vol. 1, Cold Spring Harbor Laboratory Press, (1989); Pouwels et al., Cloning Vectors: A Laboratory Manual, Elsevier, New York, (1985); "Gene Expression Technology" Methods in Enzymology, v. 185, D. V. Goeddel, ed. Academic Press Inc., San Diego, Calif. (1990); and "Viral Vectors: Gene Therapy and Neuroscience Applications" (Kaplitt, M. G., and Loewy, A. D., eds.) Academic Press, San Diego, Calif. (1995).

These polynucleotide may include the incorporation of codons "preferred" for expression of the polynucleotides in selected nonmammalian hosts, e.g., prokaryotic or non-mammalian eukaryotic host cells.

Vectors may be used to introduce the polynucleotides of this invention into a host cell. Typically, these vectors also include transcription and translational initiation regulatory sequences operably linked to the polynucleotide that encodes an archaeal replication accessory factor. These vectors would facilitate the production of such a factor in a host cell.

In certain embodiments, to produce the replication accessory factor encoded by the polynucleotide, an appropriate promoter and compatible host cell may be chosen. Examples of compatible cells lines and expression vectors are well known in the art. Certain well known host cells are prokaryotes like *E. coli*, and *B. Subtilis*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide. Examples of eukaryotic host cells are yeast, fungi, plant, insect, amphibian, avian, or mammalian cells. See, e.g., "Gene Expression Technology" Methods in Enzymology, v. 185, D. V. Goeddel, ed. Academic Press Inc., San Diego, Calif. (1990).

In certain embodiments, one may employ a selectable marker in the host cell system or vector such that transformed cells are be easily detectable. In certain embodiments, such markers are detectable after the cells have been transformed. An example includes, but is not limited to, antibiotic resistance.

Those skilled in the art will be able to construct suitable expression systems in suitable host cells, especially in view of the many publications, including manuals, that discuss such information.

This invention provides a method for producing archaeal replication accessory factors by expressing a vector that comprises a polynucleotide that encodes a replication accessory factor in a suitable host cell and purifying the expressed product. Techniques using such host cells to express such polynucleotides are well known in the art. See, e.g., Sambrook et al. (1989).

This invention also provides recombinant protein produced by the above-described method.

The invention also provides isolated and purified archaeal replication accessory factors including, but not limited to, archaeal PCNA, archaeal RFC-P38, archaeal RFC-P55, archaeal RFA, and archaeal helicases, e.g., dna2 and helicases 2 to 8.

In certain embodiments, these accessory factors have part or all of the primary structural conformation and one or more of the biological properties of a replication accessory factor.

As used herein, "isolated and purified protein" describes a replication accessory factor separate from at least one other protein that naturally accompanies the protein.

In addition to naturally-occurring allelic forms of the replication accessory factors, this invention also includes polypeptide analogs or fragments. One of skill in the art can readily design nucleic acid sequences that express such analogs or fragments of the replication accessory factors. For example, one may use well-known site-directed mutagenesis techniques to generate polynucleotides encoding such analogs or fragments. Those analogs and fragments may have one or more of the biological functions of the naturally-occurring replication accessory factor.

Further, this invention provides a composition comprising at least one archaeal replication accessory factor for use in nucleic acid polymerase reactions. As used herein "nucleic acid polymerase reactions" includes, but is not limited to, PCR-based reactions that may include site-directed mutagenesis, amplification, and synthesis of nucleic acid of interest.

In certain embodiments of the invention, the composition further comprises at least one polymerase. Such a polymerase may include, but would not be limited to, Pfu polymerase, *P. furiosus* pol II polymerase, and/or Taq polymerase.

In certain embodiments, the polymerase is an archaeal polymerase. The archaeal DNA polymerase may be obtained from archaea such as *Pyrococcus* species GB-D, *Pyrococcus* species strain KODI, *Pyrococcus woesii, Pyrococcus abysii, Pyrococcus horikoshii, Pyrodictium occultum, Archaeoglobus fulgidus. Sulfolobus solfatanicus, Sulfolobus acidocaldarium. Thermococcus litoralis, Thermococcus* species 9 degrees Nofth-7. *Thermococcus* species JDF-3, *Thermococ-* cus gorgonarius, Methanobacterium thermoautotrophicum. Methanococcus jannaschii, Methanococcus voltae, Thermoplasma acidophilum. Related archaea from which the archaeal DNA polymerase may be obtained are also described in Archaea: A Laboratory Manual (Robb, F. T and Place, A. R., eds, Cold Spring Harbor Laboratory Press, Cold Spring Harbor, N.Y., 1995).

According to certain embodiments, the archael polymerase is related to Pfu (pol I) or *P. furiosus* pol II. Commercial enzymes that are related to Pfu (pol I) that are likely to function with the *P. furiosus* replication factors are; KOD (Toyoba), pfx (Life Technologies Inc.), Vent (New England Biolabs), Deep Vent (New England Biolabs), and Pwo (Roche Molecular Biochemicals). Archaea which contain genes that exhibit DNA sequence homology to *P. fudiosus* pol II subunits are described in references (Makinjemi, M. et al. (1999) Trends in Biochem., Sci. 24:14-16; Ishino et al.(1998) J. Bacteriol., 180 2232-6).

In certain embodiments the archaeal factors are used with a thermostable eubacterial polymerase, or are used with a mixture of a eubacterial and archaeal polymerase. Thermostable eubacterial pqlymerases may be related to the pol I, pol II, or pol III class of DNA polymerases. Thermostable pol I DNA polymerases have been described in *Thermus* species (*aquaticus, flavus, thermohilus* HB-8*, ruber, brokianus, caldophius* GK14*, Filiformis*), *Bacillus* species (*stearothermophilus*, caldotenex YT-G, caldovelax YT-F), and *Thermotoga maritima*. Commercial enzymes that are related to eubacterial pol I enzymes include Taq (Stratagene) Tth (Perkin Elmer), Hot Tub/Tfl (Amersham), Klen Taq (Clone Tech), Stoffel fragment (Perkin Elmer), UlTma (Perkin Elmer), DynaZyme (Finnzymes), Bst (New England Biolabs), and Bca (Panvera). Thermostable pol III DNA polymerases have been described in *Thermus aquaticus* (Huang, et al. (1999) *J. Mol. Evol.* 48:756-69) and *Thermus thermohilus* (reference #13), but could be obtained from other thermophilic eubacteria. Additional thermophilic eubacteria are described in the reference: "Thermophilic Bacteria" Kristjansson, J. K., CRC Press, Inc., Boca Raton, Fla., 1992.

In certain embodiments, to further enhance the nucleic acid polymerase reaction, the invention may also include an archaeal dUTPase (PEF) in the composition.

Unlike current methods of enhancing nucleic acid polymerase reactions, this invention also discloses a method of enhancing nucleic acid polymerase reactions comprising employing a composition comprising at least one archaeal replication accessory factor. Such method will enhance the synthesis, amplification, or mutagenesis of nucleic acids of interest.

According to certain embodiments, the accessory factors enhance any polymerization reaction. Polymerization reactions include primer extension reactions, PCR, mutagenesis, isothermal amplification, DNA sequencing, and probe labeling. Such methods are well known in the art. Enhancement may be provided by stimulating nucleotide incorporation and reducing dissociation of the polymerase from the template. In addition, enhancement may be provided by reducing impediments in the nucleic acid templates, such as secondary structure and duplex DNA. Overcoming or improving such impediments through the addition of accessory factors like RFA and helicase, can allow polymerization reactions to occur more accurately or efficiently, or allow the use of lower denaturation/extension temperatures or isothermal temperatures. In addition, according to certain embodiments, RFA and helicase may provide additional benefits in non-polymerizing applications which require single-stranded nucleic acids. For example, RFA may improve the specificity of protein/nucleic acid interactions.

According to certain embodiments, PCNA alone or with other accessory factors may enhance exonuclease reactions carried out by the 3'-5' exonuclease activity of Pfu. Exonuclease reactions are used to prepare long single-stranded DNA templates. Enhancement may be provided by reducing dissociation of the polymerase from the template.

In addition to enhancing polymerization and exonuclease reactions, PCNA is expected to enhance repair processes that are mediated by Pfu or *P. furiosus* pol II, and that typically require additional repair proteins, such as Fen-1 and ligase.

According to certain embodiments, PCNA can also be used to enhance processes that are based upon the binding of nucleic acid sequences to complementary nucleic acid strands. For example, hybridization of labeled probes to complementary DNA or RNA strands is used in such methods as library screening, Southern blotting, Northern blotting, chip-based detection strategies, and Q-PCR detection strategies (e.g., molecular beacon hybridization probes). Such methods are well known in the art. Increasing the stability of annealed probes by the addition of PCNA may enhance specificity of hybridization reactions by allowing more stringent hybridization conditions to be used, such as higher temperature and/or lower ionic strength. Increasing the stability of primer/template interactions may also allow one to carry out more efficient polymerization reactions using RNA polymerases, reverse transcriptases and other nucleic acid polymerizing enzymes.

This invention also provides kits for nucleic acid polymerase reactions that include at least one archaeal replication accessory factor, and possibly other proteins or compounds known to enhance such reactions. In certain embodiments, the kits may also include one or more polymerases.

In certain embodiments, the kits are for synthesizing, amplifying, or mutagenizing nucleic acids of interest.

Certain embodiments of the invention are described in the following examples. However, these examples are offered solely for the purpose of illustrating the invention, and should not be interpreted as limiting the invention to these examples.

EXPERIMENTS

Methods

1. Production of Accessory Factors from *Pyrococcus furiosus*

A. DNA Sequence Identification/PCR Primers.

The DNA sequences surrounding the DNA sequences of interest were examined for likely start and stop codons. The majority of DNA sequences of interest were identified in archaeal genome databases (*Pyrococcus horekoshi, Pyrococcus furious, Methanococcus jannaschii, Methanobacterium thermoautotrophicum*), through similarity to eukaryotic genes encoding replication factors of interest (see reference No. 5). Also, the oligonucleotide sequence for PCNA was identified by N-terminal peptide sequencing of a protein isolated from a native protein preparation (see below). Table 1 below lists PCR primers used to amplify the genes and to produce ends that can be modified to produce cohesive ends with a cloning vector. The sequence corresponding to the vector sequence is underlined.

TABLE 1

| Gene Name | Forward Primer | Reverse Primer |
|---|---|---|
| RFC P98/P38 | GACGACGACAAGATGAGCGAAGAGATTAGAGAA (SEQ ID NO: 2) | GGAACAAGACCCGTTCACTTCTTCCCAATTAGGGT SEQ ID NO: 3) |
| RFC P55 | GACGACGACAAGATGCCAGAGCTTCCCTGGGTA (SEQ ID NO: 4) | GGAACAAGACCCGTTCACTTTTTAAGAAAGTCAAA SEQ ID NO: 5) |
| PCNA | GACGACGACAAGATGCCATTCGAAATAGTCTTTG (SEQ ID NO: 6) | GGAACAAGACCCGTTCACTCCTCAACCCTTGGGGCTA SEQ ID NO: 7) |
| RFC P98Intein Deletion Primers* | ACTACAGCGGCTTTGG (SEQ ID NO: 8) | CTTTCCGACACCAGGG SEQ ID NO: 9) |
| RFA | GACGACGACAAGATGATCATGAGTGCATTTACAAAAGAAGAAATAATC (SEQ ID NO: 10) | GGAACAAGACCCGTTCACATCACCCCCAATTCTTCCAATTCCC SEQ ID NO: 11) |
| dna2 helicase | GACGACGACAAGATGAACATAAAGAGCTTCATAAACAGGCTT (SEQ ID NO: 12) | GGAACAAGACCCGTTCAAATGCTATCCTTCGTTAGCACAACATA SEQ ID NO: 13) |
| Helicase 2 | GACGACGACAAGATGATTGAGGAGCTGTTCAAGGGATTAGAGAGTGAAAT (SEQ ID NO: 14) | GGAACAAGACCCGTTCATCTTTTTACGGCAAATGCGAATTCTTCTCCCTT SEQ ID NO: 15) |
| Helicase 3 | GACGACGACAAGATGTTAATAGTTGTAAGACCAGGAAGAAAAAGAATGA (SEQ ID NO: 16) | GGAACAAGACCCGTTCATCGTCTCTCACCCTTCAAAATTTTTCCTTCTTC SEQ ID NO: 17) |
| Helicase 4 | GACGACGACAAGATGCACATATTGATAAAAAGGCAATAAAAGAGAGATT (SEQ ID NO: 18) | GGAACAAGACCCGTCTATTCCCAAAACTTTCTAGTTTGGATGTAGTGTTT SEQ ID NO: 19) |
| Helicase 5 | GACGACGACAAGATGTTATTAAGGAGAGACTTAATACAGCCTAGGATAT (SEQ ID NO: 20) | GGAACAAGACCCGTCTACTCCTCATCCTCTATATATGGGGCAGTTATTA SEQ ID NO: 21) |
| Helicase 6 | GACGACGACAAGATGCTCATGAGGCCAGTGAGGCTAATGATAGCTGATG (SEQ ID NO: 22) | GGAACAAGACCCGTCTAGCTTAACTTAAGTAAATGCCTATCTTTCTTCT SEQ ID NO: 23) |
| Helicase 7 | GACGACGACAAGATGATCGAAGGTTACGAAATTAAACTAGCTGTTGTAAC (SEQ ID NO: 24) | GGAACAAGACCCGTTCAAAAACCTTTCCCAGGTATGCGGGGGTCGCT SEQ ID NO: 25) |
| Helicase 8 | GACGACGACAAGATGAGGGTTGATGAGCTGAGAGTTGATGAGAGGATA (SEQ ID NO: 26) | GGAACAAGACCCGTTCAAGATTTGAGAAAGTAATCAAGGGTACTTTTCT SEQ ID NO: 27) |

B. PCR Amplification.

1) Procedure.

DNA sequences for PCNA, RFC P98/38, RFC P55, RFA, and helicases dna2 and helicases 2-8 were amplified with various PCR enzymes and polymerase blends using the primers in Table 1. The optimal amplification procedure is described below.

PCR Reaction Mixture:

| 10 µl | 10x cloned Pfu buffer (Stratagene) |
| 0.8 | 100 mM dNTP |
| 3 µl | mixed primers (100 ng/µl of each primer) |
| 1.5 µl | PfuTurbo DNA polymerase (2.5 U/µl) (Stratagene) |
| 1 µl | genomic or plasmid DNA (approximately 100 ng/µl) |
| 83.7 µl | H$_2$0 |

2) Temperature Cycling.

Samples were amplified in a RoboCycler® temperature cycler (Stratagene). The extension time used was proportional to the amplification product size. Optimally, the extension time is 2 minutes perkilobase. The annealing temperature depended on the length and composition of the primers, which were usually designed with a Tm (melting temperature) between 50° C.-60° C. A standard temperature cycling scheme is listed below:

| 95° C. | 1 minute | 1 cycle |

The following three steps are performed sequentially and are repeated for 30 cycles:
95° C. 1 minute
50° C. 1 minute
72° C. 2 minutes/kb of target C. Cloning of PCR Products.

1) PCR Product Purification.

Three to 10 PCR reactions were generated for each DNA sequence. The PCR products were combined and purified with Stratagene's StrataPrep® PCR purification kit according to its instructions. The purified products were examined on agarose gels (1% agarose/1×TBE) to verify product size and homogeneity. The gels were stained with, ethidium bromide and visualized. If any spurious bands were present, products of the correct size were isolated withStratagene's StrataPrep® DNA gel extraction kit.

2) Insert Preparation (Ligation Independent Cloning (LIC) Method).

35 μl of purified PCR products were added to reactions containing:

| | |
|---|---|
| 5 μl | 10x cloned Pfu buffer |
| 1 μl | 25 mM dATP |
| 1 μl | cloned Pfu DNA polymerase (2.5 u/μl) | and the volume of each reaction was brought to 50 μl with 8 μl $H_2O$. The samples were incubated for 20 minutes at 72° C. in the RoboCycler® temperature cycler. This process allows the 3' to 5' exonuclease activity of the polymerase to remove bases at the 3' ends of the PCR products until a dA nucleotide is encountered. The presence of dATP in the reaction prevents further exonucleolytic degradation of the PCR product and the exposed 5' overhangs anneal precisely with the pCALnEK vector. This vector is available commercially from Stratagene and is used to produce annealing termini complimentary to the prepared insert.

3) Annealing

The treated PCR products were allowed to come to room temperature before 40 μl of each prepared insert was added to separate tubes containing 40 ng of the LIC-ready pCALnEK vector. Samples were mixed and left to anneal for 16 hours at room temperature.

D. Transformation.

The annealed vector/inserts were transformed into competent cells, namely, Stratagene's Epicurian Coli® XL10-Gold® ultracompetent cells, and selected on LB-ampicillin plates. LB media is a commonly used reagent that would be understood by those practiced in the arts. LB amp plates are made by mixing:

| | |
|---|---|
| 10 g | NaCl |
| 5 g | Yeast Extract |
| 10 g | Tryptone |
| 10 g | Agar. |

Add $H_2O$ to a final volume of 1 liter. Autoclave. Cool to 55° C. Add ampicillin to a concentration of 100 micrograms per ml. Mix well. Pour about 25 ml per plate.

Supercoiled DNA was isolated from the transformants using the instructions recommended in Stratagene's StrataPrep® Plasmid Miniprep Kit. The plasmids were used to transform BL21 (DE3) CodonPlus® or BL21 (DE3) pLysS (Stratagene) cells. These cells were again selected on LB-ampicillin plates.

E. Preparation of Recombinant Protein.

1) Bacterial Expression of Recombinant Proteins.

The transformants were grown up in multiple liter batches from overnight cultures preferably in LB media supplemented with Turbo Amp™ antibiotic (Stratagene) at 100 μg/_l at 37° C. with moderate aeration. When the cultures ill reached $OD_{600}$ readings of 0.6 to 1.0, the cells were induced with 1 mM IPTG (Stratagene) and incubated in the same manner for 2 hours to overnight (16 hours). Induction causes the vector to produce recombinant protein with a calmodulin binding peptide (CBP) amino tag. The induced cells were collected by centrifugation and stored at −20° C.

Some helicase clones appeared to be unstable in BL21 (DE3) cells. Supercoiled plasmids containing these helicases were transformed into BL21 CodonPlus® cells (Stratagene) and induced with bacteriophage Lambda CE6 (Stratagene) which contains the T7 RNA polymerase gene that provides significant production of protein in BL21 cells. Five to ten ml of $3 \times 10^{10}$ plaque forming unit (pfu)/ml lambda CE6 stock (made according to provided instructions in Lambda CE6 Induction Kit (Stratagene)) was used to induce 500 ml cultures for four hours at 37° C. with moderate aeration.

2) Purification of Recombinant Proteins.

Frozen cells were resuspended to an approximate concentration of 0.25 g/ml in buffers identical or similar to calcium binding buffer: 50 mM Tris-HCL (pH 8.0),150 mM NaCl, 1 mM magnesium acetate and 2 mM $CaCl_2$. Cell suspensions were subjected to sonication three times with a Bronson Sonifier 250 at a duty cycle of 80% and an output level of 5 for 45 seconds. The suspensions were left on ice to cool between sonication events. The lysate was cleared by centrifugation at 26,890 g.

The cleared lysates were added to a milliliter of calmodulin agarose (CAM agarose), equilibrated in buffer. Recombinant protein was bound to the CAM agarose (Stratagene) via the CBP tag by incubation with gentle agitation at 4° C. After two hours, the reactions were centrifuged at 3000 g for 5 minutes to collect the CAM agarose and recombinant protein. The lysate supernatant was removed and the CAM agarose was washed at least once by resuspending the resin in 50 ml of calcium binding buffer followed by collection of the CAM agarose by centrifugation as described above. The CAM agarose was transferred to a disposable 15 ml column, packed, and then washed with at least 50 ml of the calcium binding buffer. Recombinant proteins were eluted from the column by using a buffer similar or identical to 50 mM Tris-HCl (pH 8.0), 150 mM NaCl, 2 mM EGTA. Similar buffers may include 2 mM EGTA and the salt requirement may vary from protein to protein. Certain proteins required elution at higher ionic strength using a buffer with 1 M NaCl. Proteins were evaluated for size and purity using Tris-Glycine 4-20% acrylamide gradient gels (Novex) with an SDS loading dye (Novex). Gels were stained with silver or Sypro Orange (Molecular Probes).

F. Removal of Intein Sequence from Recombinant RFC P98 Clone.

By alignment to eukaryotic RFC sequences, it was observed that the RFC P98 clone contained an intein sequence. In FIG. 8, the intein sequences are marked in parentheses, and correspond to nucleotides 374 to 2028. Upon post-translational excision of the intein, the predicted size of the RFC subunit would decrease from 98 kDa to 38 kDa, and hence this RFC subunit is referred to as P38. To improve expression of recombinant P38 from the RFC P98 clone, the intein was removed by making 5' phosphate modified oligonucleotides that primed immediately upstream and downstream to the sequence coding for the intein termini (see primer sequence in table above, marked as *) The oligos were designed to have their 3' termini pointing away from the intein (inverse PCR). By using the RFC P98/pCALnEK plasmid as a template, all the plasmid/insert sequence was amplified with the exception of the intein. The PCR product was purified with StrataPrep PCR Purification Kit and ligated at room temperature for 16 hours prior to transformation, as described in section 1(D).

2. Protein Analysis Techniques.

A. Preparation of Antibodies.

Rabbit sera containing specific IgG was prepared by immunizing rabbits with the recombinant accessory factors. CBP-tagged fusion proteins were used to immunize 1-2 New Zealand white rabbits using the following immunization schedule: each rabbit was injected with 90-200 µg CBP-tagged fusion protein (as obtained from section 1(E)(2) above) in Complete Freund's Adjuvant (CFA), inject each rabbit with a booster 18 days later including 45-100 µg CBP-tagged fusion protein in incomplete Freund's adjuvant (IFA); inject each rabbit with a second booster of IFA 39 days later; and obtain the first serum sample 45 days later and at various times thereafter.

B. SDS-PAGE.

Native and recombinant protein samples were analyzed on 4-20% acrylamide/2.6% bis-acrylamide Tris-Glycine gels (NOVEX), stained with either silver stain or Sypro orange (Molecular Probes). Protein concentrations were determined relative to a bovine serum albumin (BSA) standard (Pierce), using Pierce's Coomassie Blue Protein assay reagent or by comparisons of relative staining intensities on SDS-PAGE gels.

C. Western Blot.

Protein samples were transferred from SDS-PAGE to nitrocellulose by electroblotting using standard techniques. The blots were blocked with 1% Blotto/TBS (instant milk in tris buffered saline) for 1 hour at room temperature, followed by incubation with immunized rabbit sera which had been diluted 1:500 or 1:1000 (1 hour). Blots were washed 3 times with TBS containing 0.01% Tween 20. The blots were then incubated for 0.5-1 hour with alkaline phosphatase-conjugated goat anti-rabbit IgG, diluted 1:500 or 1:1000 in TBS-0.01% Tween 20. Finally, the blots were washed as before and then incubated in color development solution (100 mM Tris-HCl, pH 9.5, 100 mM NaCl, 5 mM $MgCl_2$, 0.3 mg/ml NBT, and 0.15 mg/ml BCIP) for approximately 1-10 minutes. The enzyme reaction was stopped and the membrane was washed five times with deionized water.

D. Amino Acid Sequence Analysis.

Protein samples were electrophoresed and transferred to polyvinylidene difluoride (PVDF) membranes (BiORad). Blots were sent to Beckman Research Institute-City of Hope (Duarte, Calif.) for N-terminal sequence analysis.

3. Isolating DNA Encoding Recombinant RFC from a Genomic Library (Alternative Method)

A *Pyrococcus furiosus* genomic library was plated on XL1-Blue MRF' *E. coli* (Stratagene) at a density of approximately 2000 plaques per plate. Duralose filters (nitrocellulose on nylon backing) were used to take replicate lifts from each plate. While the first filter was on the plate, orientation marks were made by stabbing a needle through the filter and into the plate. The orientation marks were marked in pen on the back of the plate before the filter was removed. The filter lifts were treated as follows:

| | |
|---|---|
| 1.5-2.0 minutes | 1.5 M NaCl, 0.5 M NaOH |
| 2 minutes | 0.5 M Tris (pH 8.0), 1.5 M NaCl |
| 30 seconds | 2xSSC, 0.2 M Tris (pH 7.5) |

After treatment, the filters were partially dried until they were still damp, but no standing water was visible. The DNA was fixed onto the filters by UV crosslinking with the Stratalinker (Stratagene) set to the "Autolink" format according to the instructions.

The filters were prehybridized in 15 ml of:
5xSSC
40 mM $NaPO_4$ pH (6.5)
5xDenhardt's
5% Dextran Sulfate
50% Formamide
0.1 mg/ml Salmon sperm DNA (Boiled separately and added immediately prior to use)

Prehybridization was carried out at 42° C. for approximately 2 hours.

Probe was generated from a 200 bp PCR product amplified from *Methanococcus jannaschii* genomic DNA using the following primers:

```
Oligo # 576:    GAT GAA AGA GGG ATA GAT
                (SEQ ID NO: 36)

Oligo # 577:    ATC TCC AGT TAG ACA GCT
                (SEQ ID NO: 37)
```

These PCR primers were designed to anneal to regions flanking a 200 bp sequence of the *Methanococcus jannaschii* RF-C gene that exhibits 52% amino acid identity to the RF-C gene from human. (See Section 2 under Results below).

The PCR product was purified from free primers, buffer and nucleotides and 50 ng of the product was labeled with $^{32}P$-αdATP using the Stratagene Prime-It II Random Primer Labeling kit. The probe was purified from free nucleotides before being boiled for five minutes and added to the prehybridization reaction. The total probe was calculated to be 20 million cpm. Hybridization was allowed to continue overnight at 42° C. before the hybridization solution was removed and the filters were washed four times with 0.1xSSC, 0.1% SDS at 60° C. (very stringent conditions). The filters were exposed to X-ray film overnight and 20 primary isolates with strong signals on both replicate filters were picked.

Three primary isolates were diluted, plated, and screened again using the same method described above. Two filters produced positive lambda clones. Bluescript plasmid clones were excised from the lambda clones in SOLR cells (Stratagene) according to the manufacturers instructions. The clones had inserts sizes of 8 kb and 10 kb. These plasmid clones were cut with Hind III, blotted, and probed with the original 200 bp PCR product discussed above. One positive truncated clone was isolated and sequenced from each end of the insert. The sequence showed two RF-C sequences, specifically, the C-terminus of one sequence, and the N-terminus of another.

4. Production of Accessory Factors from Native Sources

A. *P. furiosus* Extract.

Fermentation of *P. furiosus* DSM 3638 cells was carried out using the procedure described in Archaea: A Laboratory Manual, Robb, F. T. (editor-in-chief), Cold Spring Harbor Press, CSH, NY 1995. The cell paste was resuspended in lysis buffer (50 mM Tris-HCl (pH 8.2), 1 mM ethylenediaminetetraacetic acid (EDTA), 10 mM beta-mercaptoethanol (_-ME), 0.5 mM phenylmethylsulfonyl fluoride (PMSF), and 2_g/ml aprotinin) and lysed in a French press, and then the lysate was sonicated and centrifuged.

B. Column Chromatography.

The supernatant was chromatographed on a Q-Sepharose Fast Flow column (Pharmacia), equilibrated in 50 mM Tris-HCl (pH 8.2), 1 mM EDTA, and 10 mM_-ME. Follow-through fractions were collected, adjusted to pH 7.5, and then loaded onto an SP Sepharose Big Bead column (Pharmacia), and equilibrated in buffer A (50 mM Tris-HCl (pH 7.5), 1 mM EDTA, 1 mM dithiothreitol (DTT), 10% (v/v) glycerol, 0.1% (v/v) Igepal CA-630, and 0.1% (v/v) Tween 20). The column was eluted with a 0-0.25 M KCl gradient/Buffer A. Fractions containing DNA polymerase activity were dialyzed, and then applied to a Heparin Sepharose CL-6B column (Pharmacia), and equilibrated in Buffer B (same as buffer A, except pH 8.2). The column was eluted with a 0-0.3 M KCl gradient/Buffer B. Fractions exhibiting polymerase enhancing activity (nucleotide incorporation) (using the assay described below in Section 5(B)), or immunocrossreactivity (using the Western Blot described in Section 2(C) above) were identified. Native. PCNA was further purified by excising the protein from SDS-PAGE gels.

C. Immunoaffinity Chromatography.

Immunoaffinity columns were prepared using the commercial kit from Pierce (Immunopure Plus Cat# 44893), following the manufacturer's method. Two milliliters of serum, mixed with 2 milliliters of kit loading/binding buffer, was used to prepare each column. Before using the column, the column and buffers were allowed to warm to room temperature.

1) Preparation of Extract.

0.5 g frozen *P. furiosus* cells were used for each column. The cells were lysed in 2 ml lysis buffer (50 mM Tris pH 8.0, 1 mM EDTA, and 1 mM DTT), and sonicated twice for 2 minutes on ice. The cells were spun at 26,890 g for 15 minutes and the supernatant was recovered. The lysate was mixed with an equal volume of binding buffer (10 mM Tris pH 8.0, 50 mM KCl, 0.1% Tween 80). The lysate was precleared by incubation with 4 ml of protein A beads (Pierce cat # 20333) and equilibrated with binding buffer. The slurry was incubated it 4° C. for 1 hour with agitation. The precleared extract was recovered by packing the beads into a disposable column and the flow-through was collected. The column was washed with 2 ml of binding buffer and the wash was collected and pooled with the flow-through fraction. The final volume of pretreated lysate is about 6 ml. In some cases, the lysate was then run over a pre-bleed rabbit IgG control column to further clean up the lysate.

2) Immunoaffinity Chromatography.

The column was equilibrated with 15 ml binding buffer (10 mM Tris HCl (pH 8.0), 50 mM KCl, 0.1% Tween 80), and then, the 6 milliliters of precleared lysate was applied to the column. The column was washed with 10 milliliters binding buffer, followed by 10 milliliters wash buffer (10 mM Tris pH 8.0, 500 mM KCl, 0.1% Tween 80). Specific proteins were eluted with seven 1 ml washes of elution buffer (0.1 M glycine pH 2.8). One ml fractions were collected. To each collection tube, was added 50 µl 1 M Tris pH 9.5 to raise the pH of the eluates as they are collected. After eluting the protein of interest, the column was washed with 4 ml of 1M Tris pH 8.0 and then 15 milliliters of binding buffer.

5. Biochemical Assays

A. Primer Extension Assay.

The *Pyrococcus furiosus* accessory proteins were tested for their ability to stimulate the processivity of cloned Pfu polymerase activity on primed single-stranded M13 DNA. One version of this assay provided for detecting extension products under non-denaturing conditions using ethidium bromide staining. For this assay, a reaction cocktail was made containing:

| | |
|---|---|
| 5 µg/ml | single-stranded M13 mp 18(+) strand DNA (Pharmacia cat# 27-1546-01) |
| 275 ng/ml | 40-mer primer (5' GGT TTT CCC AGT CAC GAC GTT GTA AAA CGA CGG CCA GTG C 3') (SEQ ID NO: 38) |
| 200 µM each | dNTP |
| 1X | cPfu buffer |
| | water to 20 µl. |

Single stranded M13 DNA was mixed with primer, buffer, and water. The mix was heated to 95° C. for 2 minutes and then cooled to room temperature. The rest of the reaction components were added. Each 20 µl reaction contained 0.05 units of cloned Pfu polymerase and varying amounts of PCNA and RFC. For assessing *P. furiosus* RF-C enhancement, assays contained 0.025 µl of *P. furiosus* PCNA (about 1 ng), and varying amounts of native *P. furiosus* RF-C. The reactions were incubated at 72° C. for 15 minutes. 2 µl DNA loading dye (50% glycerol, 1×TBE, 0.05% bromphenol blue+0.05% xylene cyanol) was added to each sample and 15 µl of sample with dye was loaded in each well of a 1% agarose gel (Reliant, FMC cat# 54907). The gel was stained with ethidium bromide. The double-stranded M13 can be seen as a brightly staining product that migrates higher than a 12 kb marker similar to the position where a double-stranded M13 DNA control migrates. In this assay, one looks for an increase in the size of products synthesized when PCNA or PCNA+RFC are added to Pfu. Ethidium bromide staining is proportional to the amount of double-stranded DNA produced from primed single-stranded M13.

A second version of this gel-based assay allows detection of radiolabeled extension products under denaturing conditions. The same template is used, except the 40 bp primer has been phosphorylated at the 5' end with [γ-$^{32}$P]ATP (>5000 Ci/mmole) and T4 polynucleotide kinase. The labeled oligo was purified using a NucTrap probe purification column (Stratagene) and then annealed with single-stranded M13 at equimolar concentrations (100 nM). The reaction cocktail comprised:

9.5 µg/ml single-stranded M13mp18 (+) strand DNA (Pharmacia)

52 ng/ml 40-mer

100 µM each dNTP

1×cloned Pfu DNA polymerase buffer and water to 50 µl.

Single-stranded M13 DNA was mixed with primer, buffer and water. The mix was heated to 95° C. for 2 minutes and then cooled to room temperature. The rest of the reaction components were added. Each reaction contained diluted cloned Pfu DNA polymerase, and varying amounts of PCNA, and RFC. Reactions were incubated at 72° C. for varying times ranging from 1-30 minutes. The reactions were terminated by adding 3.3 µl of stop dye (95% formamide/20 mM EDTA/0.05% bromphenol blue/0.05% xylene cyanol). The reaction mixtures were then subject to polyacrylamide gel electrophoresis using 6-8% denaturing gels, and the gels are dried down and exposed to autoradiographic film. The size of the full length extension product was t determined by carrying out primer extension using excess cloned Pfu DNA polymerase for 30 minutes.

B. Stimulation of Nucleotide Incorporation

The accessory factors were also tested for the capability of increasing dNTP incorporation by Pfu DNA polymerase or *P. furiosus* pol II DNA polymerase. This assay involves measuring dNTP incorporation into primed M13 DNA, by isolating and counting high-molecular-weight DNA bound to DE81 filter paper. A reaction cocktail is prepared as follows:

4 µg/ml single-stranded M13 mp18 (+) strand DNA (Pharmacia)

219 ng/ml 40-mer (see Section 5(A) above)

1×cloned Pfu DNA polymerase buffer (Stratagene)

300 µM each dGTP, dATP, dCTP

30 µM dTTP

5 µM $^3$H-TTP (NEN NEG-221H)

Figure 42:
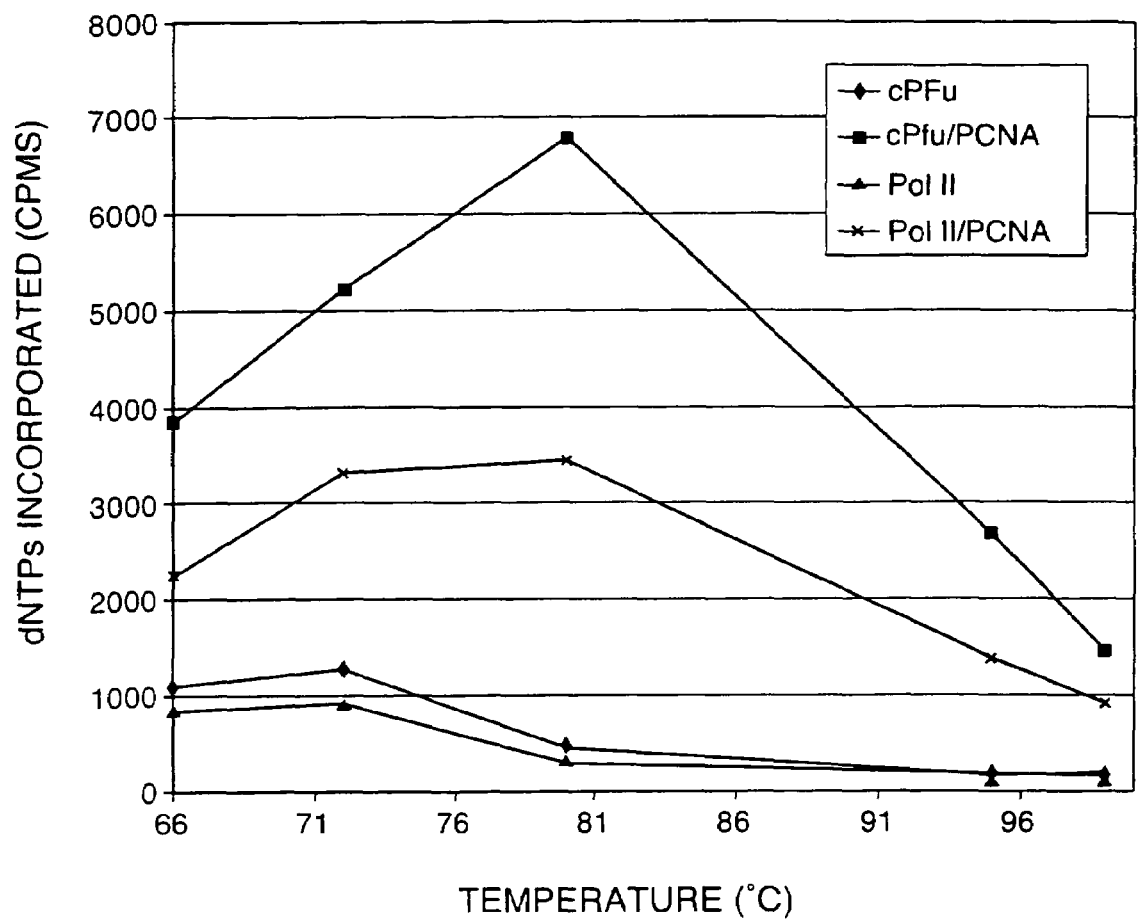
FIG. 42 Illustrates the stimulation of nucleotide incorporation by Pfu and P. furiosus pol II DNA polymerases using PCNA. Primer extension reactions were performed at 66-99° C. using primed single-stranded M13 DNA. Optimal activity was observed at or above 80° C. in the presence of PCNA (no measurements carried out between 80 and 95° C.), while reduced activity was observed above 72° C. in the absence of PCNA.

To 10 µg of reaction cocktail was added either 0.025 units cloned Pfu Polymerase (Stratagene) or 0.05 units *P. furiosus* pol II. *P. furiosus* pol II was PCR amplified using the DNA sequences described in reference 15 below, and recombinant CBP-DP1/DP2 DNA polymerase was cloned, expressed, and purified as described using the procedures outlined above in Section 1. To assay the temperature-dependence of PCNA enhancement (data in FIG. 42), reactions were carried out for 10 minutes in the absence or presence of 10 ng PCNA, using incubation temperatures ranging from 66-99° C.

The extension reactions were quenched on ice, and then 5 µl aliquots were spotted immediately onto DE81 filters (Whatman). Unincorporated [$^3$H]TTP was removed by 6 washes with 2×SCC (0.3M NaCl, 30 mM sodium citrate, pH 7.0), followed by one wash with 100% ethanol. Incorporated radioactivity was measured by scintillation counting.

This assay can be modified to allow improved detection of PCNA by reducing dNTP incorporation to background levels through the addition of 200 mM KCL to the reaction mix. PCNA alone or in combination with other accessory factors can be detected by restoration of Pfu's DNA polymerase activity.

The assay cocktail contains:

```
10 µg/ml     single-stranded M13 mp 18(+) strand DNA
             (Pharmacia cat# 27-1546-01)

100 ng/ml    40-mer primer
             (GGT TTT CCC AGT CAC GAC GTT GTA
             AAA CGA CGG CCA GTG C)
             (SEQ ID NO: 39)

1X           cPfu buffer 200 mM       KCl

30 µMeach    dATP, dCTP, dGTP

3 µM         dTTP

5 µM         ³H-dTTP (NEN cat# NET-221H) (100 µCi/mL)

100 U/ml     cloned Pfu polymerase
```

Recombinant accessory factors or fractions derived from native *P. furiosus* are assayed for their ability to restore polymerase activity to the above cocktail. 1 µl samples were added to 10 µl of reaction cocktail, and reactions were incubated at 72° C. for 30 minutes. Reactions were spotted onto DE81 filter papers, which were then washed and counted as described above.

C. ATPase Assay.

One µl of RFC or helicase preparations were incubated with 1 µl of 4.5 µM ATP and 1 µCi of gamma labeled $^{33}$P-ATP in 10 mM Tris HCl (pH 8.3), 3.5 mM MgCl$_2$, and 75 mM KCl. The samples were incubated at 72° C. for 20 minutes before being spotted on PEI cellulose F (EM Science). After drying, the PEI cellulose was placed in a shallow reservoir of 0.4 M NaH$_2$PO$_4$ pH 3.5. The liquid front was allowed to migrate 4-5 cm before being removed from the liquid and dried. The samples were exposed to X-ray film for one hour. Evidence of ATPase activity in samples was obtained by looking for radioactivity migrating with the liquid front. The positive control (porcine ATPase) converts $^{33}$P-γ-dATP to dADP+$^{33}$P-γ P; the latter product migrates with the liquid front under these TLC conditions, while the $^{33}$P-γ-dATP substrate remains near the origin. In some cases, product was quantified by excising the product spots from the PEI plate and then counting in a scintillation counter.

D. Gel Shift Assay.

A 38 base oligo (5' GGT TTT CCC AGT CAC GAC GTT GTA AAA CGA CGG CCA GT 3') (SEQ ID NO: 40) was incubated with RFA samples at 95° C. for 10 minutes, followed by 72° C. for 2 minutes, prior to loading on a 4-20% acrylamide gradient gel (Novex) in 1×TBE buffer. Bands were visualized by SYBER green staining (Molecular Probes) and UV illumination. DNA binding activity is monitored by looking for a retardation in the migration of the oligo (higher band) in the presence of RFA. Single-strand DNA binding activity is verified by showing a shift in band position using a single-stranded oligo but no shift using a double-stranded DNA duplex.

E. Helicase Assay.

Radioactively labeled oligonucleotides with a 3' overhang or a 5' overhang were annealed to M13mp18 DNA (Pharmacia). The reactions were incubated with 0.5 µl of putative *P. furiosus* helicases in 50 mM Tris HCl, pH 8.5, 25 mM KCl, and 5 mM ATP for 30 minutes at 55° C. The positive control was generated by thermally melting the annealed oligo prior to loading. The samples were run on 4-20% gradient acrylamide gels in 1×TBE. The gels were dried and exposed to X-ray film. Samples with helicase activity will displace the annealed radiolabeled oligo from single-stranded M13 DNA. On a gel, helicase-displaced oligo will migrate with the same mobility as oligos melted off M13 DNA with heat (free oligo). In samples lacking helicase activity, oligo will still be bound to M13 and will migrate at a different position which will be identical to "template only" controls.

6. PCR Reactions.

PCR reactions were carried out under standard conditions. In general, amplification reactions (50 µl) contained 200-450 µM each dNTP, 1×PCR buffer, 50-200 ng of human genomic DNA template (or 100 ng Stratagene's Big Blue transgenic mouse genomic DNA for the 0.5 kb target), 100 ng of each primer, and 2.5-5 U of TaqPlus® Long DNA polymerase blend, PfuTurbo DNA polymerase, or Taq2000 DNA (Stratagene) polymerase. TaqPlus® Long PCRs were carried out in 1×buffer including: 50 mM Tricine pH 9.0, 8 mM ammonium sulfate, 0.1% Tween-20, 2.3 mM MgCl$_2$, and 75 ng/ml BSA. PCRs using PfuTurbo or Taq2000 DNA polymerase were carried out with the PCR buffers provided with the enzymes (Stratagene). Reactions were cycled in 200 µl thin-walled tubes using any of the following temperature cyclers: Stratagene RoboCycler® 96 temperature cycler fitted with a hot top assembly, Perkin Elmer GeneAmp PCR System 9600, or MJ Research PTC-200 Peltier thermocycler. The sequences of the PCR primers are given below:

```
23 kb β-globin
Forward primer:
5'-CAC AAG GGC TAC TGG TTG CCG ATT-3'
(SEQ ID NO: 44)

Reverse primer:
5'-AGC TTC CCA ACG TGA TCG CCT TTC TCC CAT-3'
(SEQ ID NO: 45)

30 kb β-globin
Forward primer:
5'-CTC AGA TAT GGC CAA AGA TCT ATA CAC ACC-3'
(SEQ ID NO: 46)

Reverse primer:
5'-AGC TTC CCA ACG TGA TCG CCT TTC TCC CAT-3'
(SEQ ID NO: 47)

2.1 kb Alpha 1 Anti-Trypsin
Forward primer:
5'-GAG GAG AGC AGG AAA GGT GGA AC-3'
(SEQ ID NO: 48)

Reverse primer:
5'-GAA AAT AGG AGC TCA GCT GCA G-3'
(SEQ ID NO: 49)

5.2 kb Alpha 1 Anti-Trypsin
Forward primer:
5'-GAG GAG AGC AGG AAA GGT GGA AC-3'
(SEQ ID NO: 50)

Reverse primer:
5'-GCT GGG AGA AGA CTT CAC TGG-3'
(SEQ ID NO: 51)

0.5 kb λ/lacI (transgenic mouse genomic DNA)
lambda primer:
5' GAC AGT CAC TCC GGC CCG-3'
(SEQ ID NO: 52)

lacZ primer:
5' CGA CGA CTC GTG GAG CCC-3'
(SEQ ID NO: 53)
```

The following temperature cycling conditions were used for the 23 and 30 kb β-globin targets: 92_for 2 min. (1 cycle); 92_for 10 sec., 65_for 30 sec., 68_for 15 min. (10 cycles); 92_for 10 sec., 65_for 30 sec., 68_for 25 min. (with a increase of 10 sec. added progressively to the extension time with each cycle)(20 cycles). The 2.1 and 5.2 kb targets were amplified as follows: 95_for 1 min. (1 cycle); 95_for 1 min., 58_for 1 min., 72_for 2 min. (for 2 kb target) or 5 min. (for the 5.2 kb target) (30 cycles); 72_for 10 min. (1 cycle). The 0.5 kb target was amplified as follows: 94_for 1 min. (1 cycle); 94_for 1 min., 54_for 2 min., 72_for 1.5 min. (30 cycles); 72_for 10 min. (1 cycle).

Results

1. PCNA.

Figure 2:
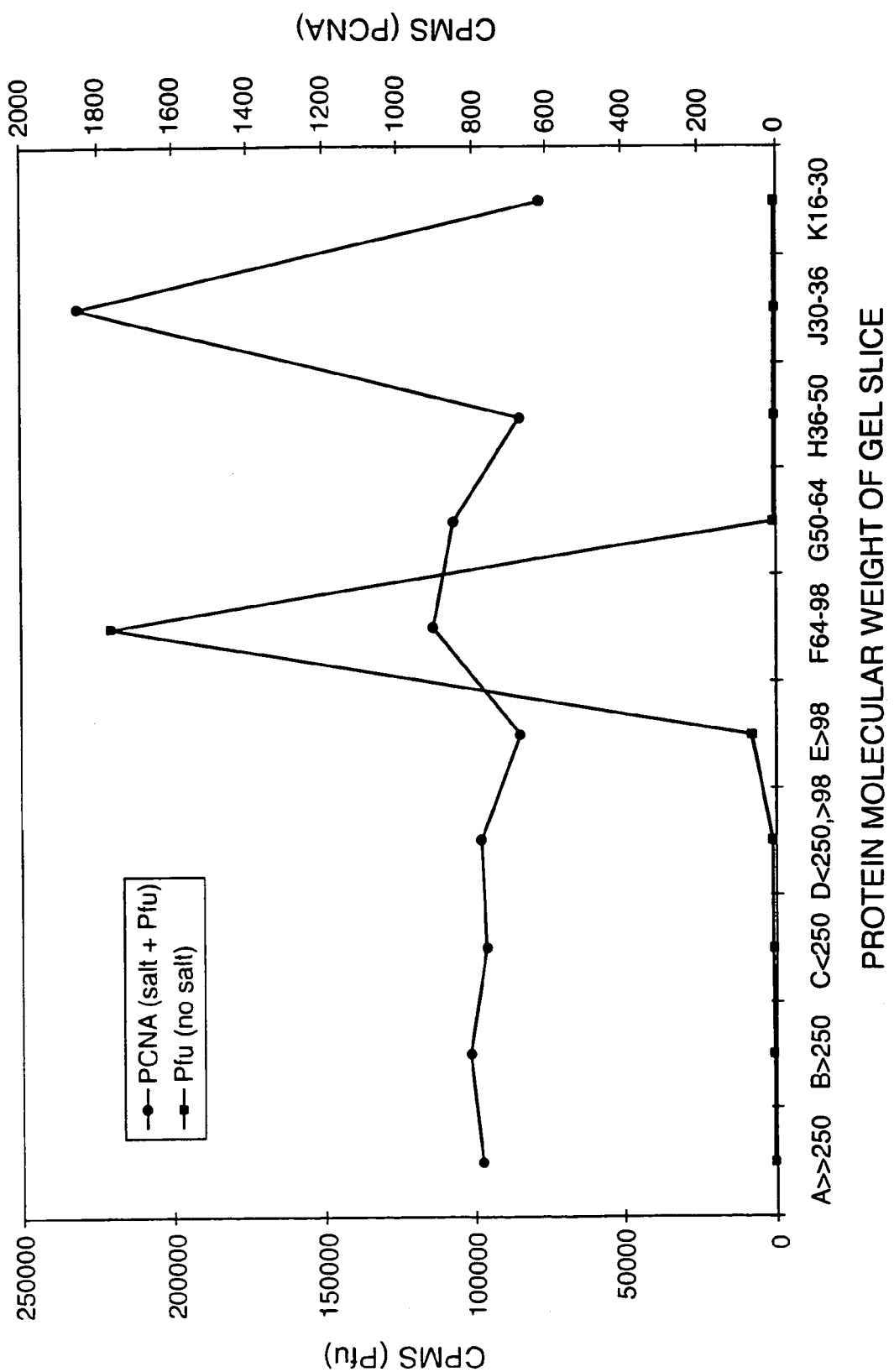
FIG. 2 illustrates the identification of native PCNA activity in SDS-PAGE gel slices. An active heparin sepharose fraction was electrophoresed on an SDS-PAGE gel, and slices of the gel were excised and the proteins eluted. The presence of PCNA or polymerase activity was determined as described above in FIG. 1 and in the Detailed Description of Embodiments of the Invention.

*P. furiosus* PCNA was first identified in column fractions produced during fractionating native *P. furiosus* extracts. PCNA was co-purified with Pfu DNA polymerase during the Q and SP column procedures discussed above. Peak PCNA activity could be resolved from peak DNA polymerase activity using the heparin sepharose column, but all PCNA-containing fractions were contaminated with DNA polymerase activity. To isolate native PCNA, fractions that could restore DNA polymerase activity to salt-inactivated Pfu DNA polymerase were studied. Such "restoration" activity was detected in column fractions eluting off the Heparin sepharose (FIG. 1). An active column fraction was then subject to SDS-PAGE and gel slices were excised and extracted to remove proteins. DNA polymerase activity was found in a gel slice recovered from a position in the gel corresponding to the migration of proteins between 64-98 kDa. In contrast, PCNA activity was recovered from a gel slice that was located at a position lying between the 30 and 36 kDa protein markers (FIG. 2). A protein band, migrating at 35 kDa, was visible on SDS-PAGE gels. This protein was transferred to a PVDF membrane (Bio Rad) and sent for amino terminal sequencing. The N-terminal sequence of the 35 kDa protein was: PFEIVFEGAKE-FAQLIDTASKL(H,I)DEAAFKVTEDG—MR (SEQ ID NO: 54) (where (H,I) means either amino acid could be present, and—means that any amino acid could be present). A BLAST search of DNA sequence databases identified the 35 kDa protein as exhibiting significant homology to known eukaryotic PCNA sequences.

The sequence encoding *P. furiosus* PCNA was cloned in the pCALnEK vector using the PCNA PCR primers described above. The LIC-primers were designed using the DNA sequence for PCNA identified in the *Pyrococcus horekoshi* genome sequence database. Although closely related to archaea, *Pyrococcus horekoshi* is a different species of *Pyrococcus* than *Pyrococcus furiosus*. The translated N-terminus of the putative *Pyrococcus horekoshi* PCNA matches the chemically determined N terminal sequence of native *Pyrococcus furiosus* PCNA. The DNA sequence of the pCALnEK clone encoding *Pyrococcus furiosus* PCNA is shown in FIG. 3, and its translated amino acid sequence is shown in FIG. 4. The predicted molecular weight of *P. furiosus* PCNA is 28 kDa although the apparent molecular weights of EK-digested recombinant PCNA and native PCNA are 38 and 35 kDa, respectively.

Figure 5:
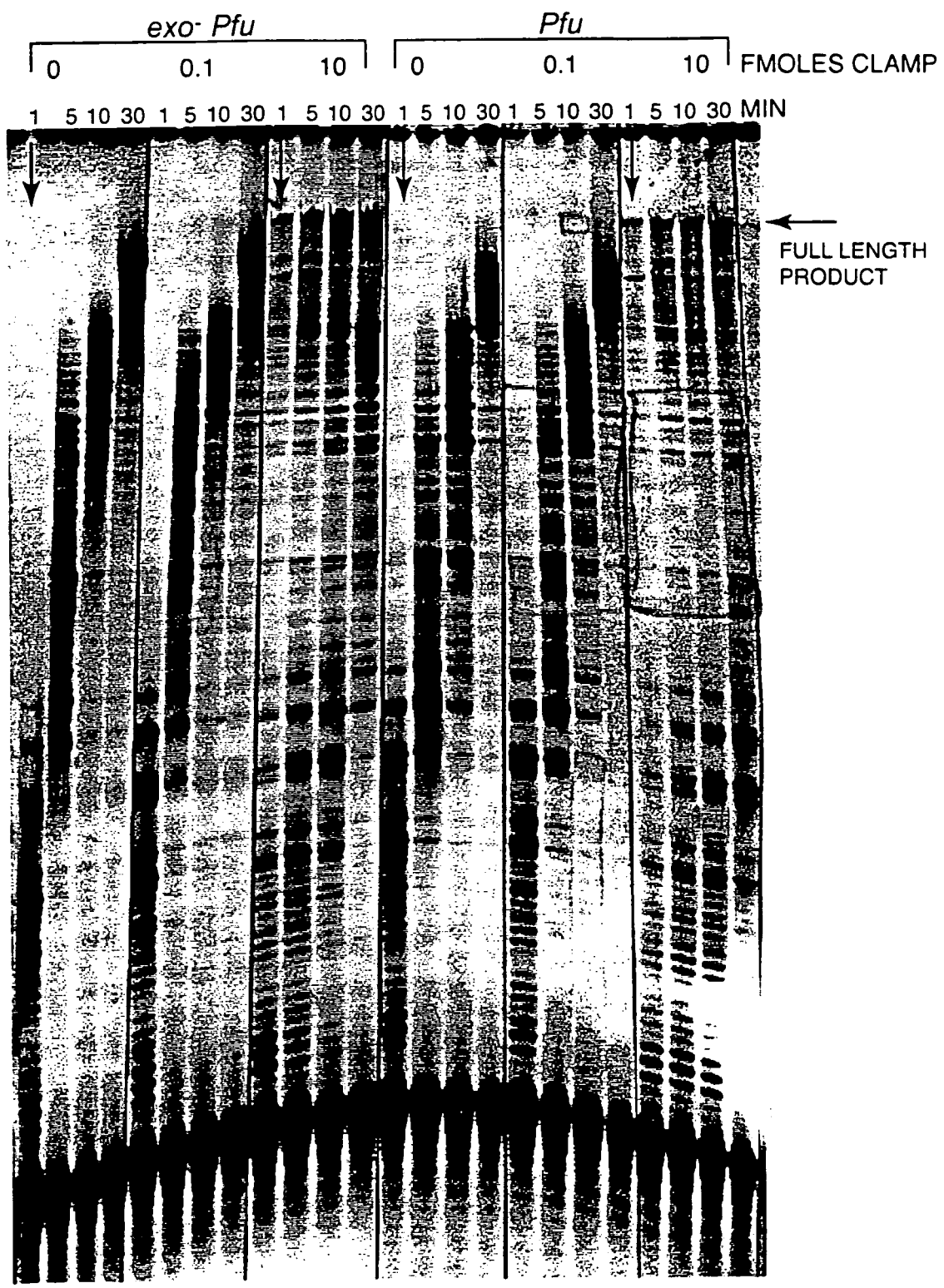
FIG. 5 illustrates that PCNA enhances the processivity of Pfu DNA polymerase. A 5'-radiolabelled 38 bp oligonucleotide was annealed to single-stranded M13. The template was incubated at 72° C. in the presence of cloned Pfu PCR buffer, dNTPs, and either cloned Pfu DNA polymerase or exo Pfu DNA polymerase. To certain reactions, ~0.1 or 10 fmoles of PCNA was added. Reactions were allowed to proceed for 1, 5, 10, or 30 minutes, and then stopped in loading buffer. The extension products were electrophoresed on CastAway® prepoured 6% (7M urea) gels, and the gels were dried and visualized by autoradiography. The length of the fully extended product is approximately 7 kb.

In addition to stimulating nucleotide incorporation by salt-inactivated Pfu DNA polymerase, both native and recombinant *Pyrococcus furiosus* PCNA preparations were shown to significantly increase the processivity of Pfu. When PCNA is added to primer extension reactions where a 5' radiolabelled primer is annealed to single stranded M13, the majority of the products generated at early time points are full-length and fewer short truncated products accumulated (FIG. 5). These results indicate that PCNA has significantly increased the processivity of Pfu polymerase (number of bases added per polymerase/DNA binding event), and the overall rate of incorporation (nucleotides incorporated per unit time) is increased.

The effects of PCNA on *P. furiosus* pol II DNA polymerase were also tested. PCNA was shown to stimulate dNTP incorporation by both Pfu (pol I) and *P. furiosus* pol II DNA polymerases. Interestingly, the addition of PCNA altered the optimal reaction temperature for both DNA polymerases. Because DNA duplexes are unstable at elevated temperatures (>Tm), assaying DNA polymerases at temperatures approaching the optimal growth temperatures of hyperthermophilic archaea (>100° C.) has been difficult. For the M13/40-mer duplex shown here, reaction temperatures above 75° C. produce template instability, consistent with the drop in activity for both polymerases between 72 and 80° C. However, in the presence of PCNA, the primer/M13 duplex appears to be stabilized at temperatures >72° C., leading to even higher primer extension activity by both Pfu (pol I) and *P. furiosus* pol III DNA polymerases. Thus, the M13/oligo duplex remains annealed at temperatures greater than about 80° C.

These data indicate that the addition of PCNA can have other benefits besides enhancing the polymerization rate and processivity of Pfu (pol I) and *P. furiosus* pol II DNA polymerases. The use of PCNA should allow the use of these hyperthermophilic enzymes at higher temperatures than has been achieved to date. PCR amplification, DNA sequencing, and isothermal amplification reactions employ extension temperatures of ≦72° C. to ensure stability of the primer/template duplex. However, this temperature is well below the expected temperature optimum of DNA polymerases from hyperthermophilic archaea like *P. furiosus*. It may be possible to use elevated extension temperatures during these polymerization reactions (e.g., >80° C.), which would have the benefits of increasing polymerase activity (by operating closer to optimum reaction temperature) and reducing interference from secondary, structure in DNA templates.

In addition, the apparent stabilization of primer/M13 DNA duplexes by PCNA may have utility in improving applications that require high stability of nucleic acid duplexes. For example, PCNA may enhance the specificity of probe hybridization reactions by allowing the use of more stringent annealing temperatures or reaction conditions (lower ionic strength).

Figure 6:
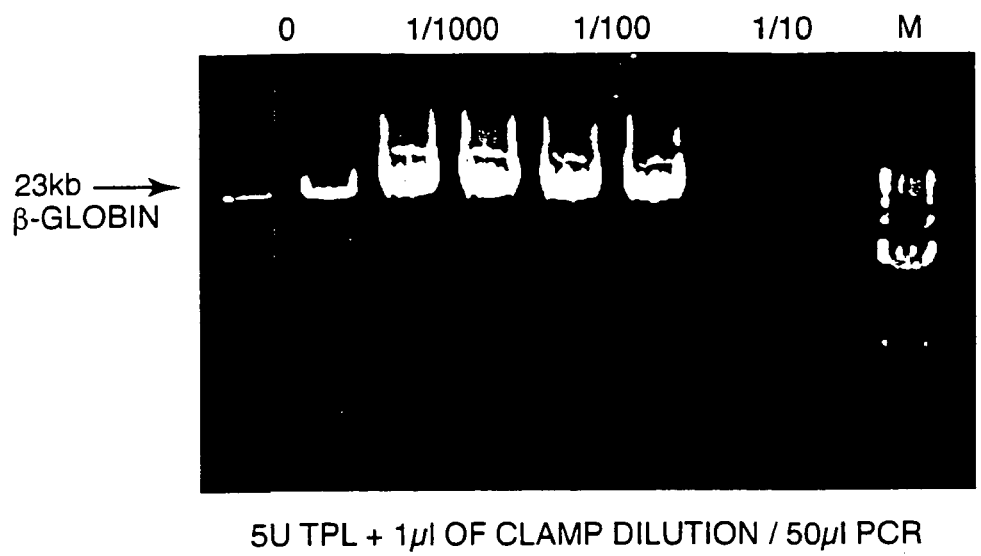
FIG. 6 illustrates the stimulation of TaqPlus® Long DNA polymerase blend (Stratagene) with PCNA. A 23 kb fragment was amplified from genomic DNA using 5U TaqPlus® Long polymerase blend, in the presence of native PEF, a no KCl buffer, and varying amounts of PCNA.
Figure 7:
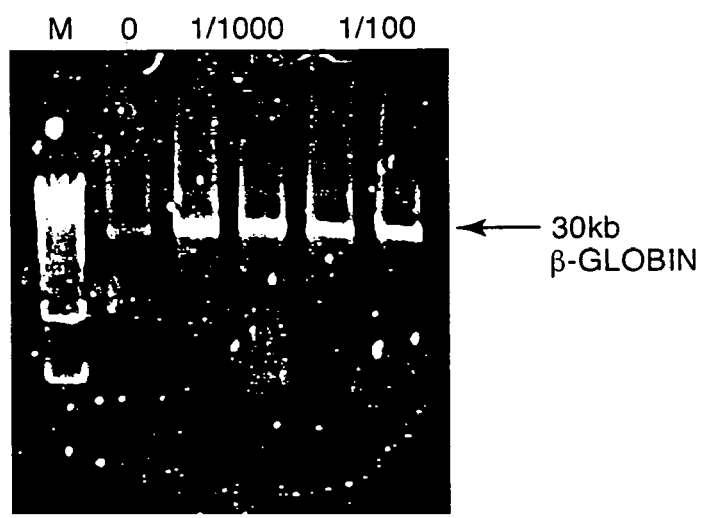
FIG. 7 illustrates the stimulation of TaqPlus® Long DNA polymerase blend with PCNA. A 30 kb fragment was amplified from genomic DNA using 5U TaqPlus® Long, in the presence of native PEF, a no KCl buffer, and varying amounts of PCNA.

The effect of adding PCNA without other accessory factors to PCR amplification reactions has been tested. In the absence of other accessory factors, relatively high concentrations of PCNA (100 ng-1 ug) can inhibit product synthesis by Pfu DNA polymerase. Lower concentrations of PCNA are tolerated in PCR amplification reactions (<100 ng). PCNA is functional and beneficial to PCR amplification reactions (FIGS. 6 and 7). PCNA can dramatically increase the yield of products amplified with DNA polymerase blends including Taq, Pfu, and *P. furiosus* dUTPase (PEF). In the blends that have been tested, Taq is present at 2.5-5 U and Pfu is present at 0.156-0.3125 U. The dUTPase may be in the form of native PEF or recombinant dUTPase (P45) (See WO 98/42860) and present at 1-10 ng per reaction. PCNA enhances the processivity of the minor proofreading component in the DNA polymerase blend, while dUTPase is preventing dUTP incorporation (and subsequent Pfu inhibition), so that greater Pfu polymerase activity can be realized. The dUTPase activity is discussed in International Patent Application WO98/42860, which is incorporated in its entirety by reference. Therefore, PCNA in its optimal concentration should enhance archaeal DNA polymerases (such as Pfu, pol II), either alone, or in combination or blended with other non-proofreading DNA polymerases of eubacterial or archaeal origin. In addition, PCNA activity can be improved by the further addition of other accessory factors including *P. furiosus* RFC, RFA and helicase.

2. RFC.

Before this invention, the inventors were not aware of the availability of an archaeal genome sequence other than the sequence of *Methanococcus jannaschii*. Genome sequence of *Methanococcus jannaschii* contained ORFs, which exhibited significant DNA sequence homology to DNA replication proteins from eukaryotes, including one Family B DNA polymerase, two RFC subunits, and PCNA (Bult et al., 1996 (Reference No. 6)). In eukaryotes, the RFC complex is composed of five distinct subunits (one large subunit and 4 small subunits that are associated with ATPase activity) and is stimulated by PCNA. However, only two genes were identified in *Methanococcus jannaschii* as exhibiting homology to RFC subunits: one sequence was identified as a putative homolog of the large RFC subunit and a second sequence was identified as a putative homolog of one of the small subunits. Initially, PCR primers were based upon the DNA sequences of the putative *Methanococcus jannaschii* rfc genes. However, these primers did not amplify a PCR product from *P. furiosus* genomic DNA, presumably because of the divergence in DNA sequence between *Methanococcus jannaschii* and *Pyrococcus furiosus*.

The inventors used an alternative approach to clone *P. furiosus* RFC subunits. Amino acid sequence alignments between *Methanococcus jannaschii* and human RFC identified a 67-amino acid region with 52% identity. A portion of RFC was likely to be highly conserved among archaea, since it was relatively conserved between more distantly related organisms, i.e., humans and archaea.

A 200 bp sequence encompassing the region encoding the 67-amino acid region was amplified from *Methanococcus jannaschii* genomic DNA using the following primers: 5' GAT GAA AGA GGG ATA GAT (SEQ ID NO: 36) and 5' ATC TCC AGT TAG ACA GCT (SEQ ID NO: 37). The *Methanococcus jannaschii* sequence was used to probe a *P. furiosus* genomic DNA library.

One positive genomic clone was recovered which contained the sequences encoding both the large and small subunits in tandem. The DNA sequence of the genomic clone is shown is FIG. 8 and the translated amino acid sequence is shown in FIG. 9. The genomic sequences of P38 and P55 are bracketed. The nucleotide sequence of P38 is nucleotides 197 to 2835 (the intein sequence is nucleotide 374 to 2028). The nucleotide sequence of P55 is nucleotides 2839 to 4281. Examination of the DNA sequence encoding the a small *P. furiosus* RFC subunit (P98) revealed the presence of an intein. An intein had also been identified in the gene encoding the putative *Methanococcus jannaschii* small RFC subunit (Bult et al, 1996).

Expression constructs were prepared by subcloning the sequences encoding the large and small subunits into the pCALnEK vector. To facilitate expression, the intein was removed from the small RFC subunit clone by amplification with primers designed to anneal to the 5' and 3' regions flanking the intein sequence and to prime in a direction opposite to the intein. The amino acid sequences of the large RFC subunit and the small "intein-less" RFC subunit are shown in FIGS. 10 and 11.

Figure 12A:
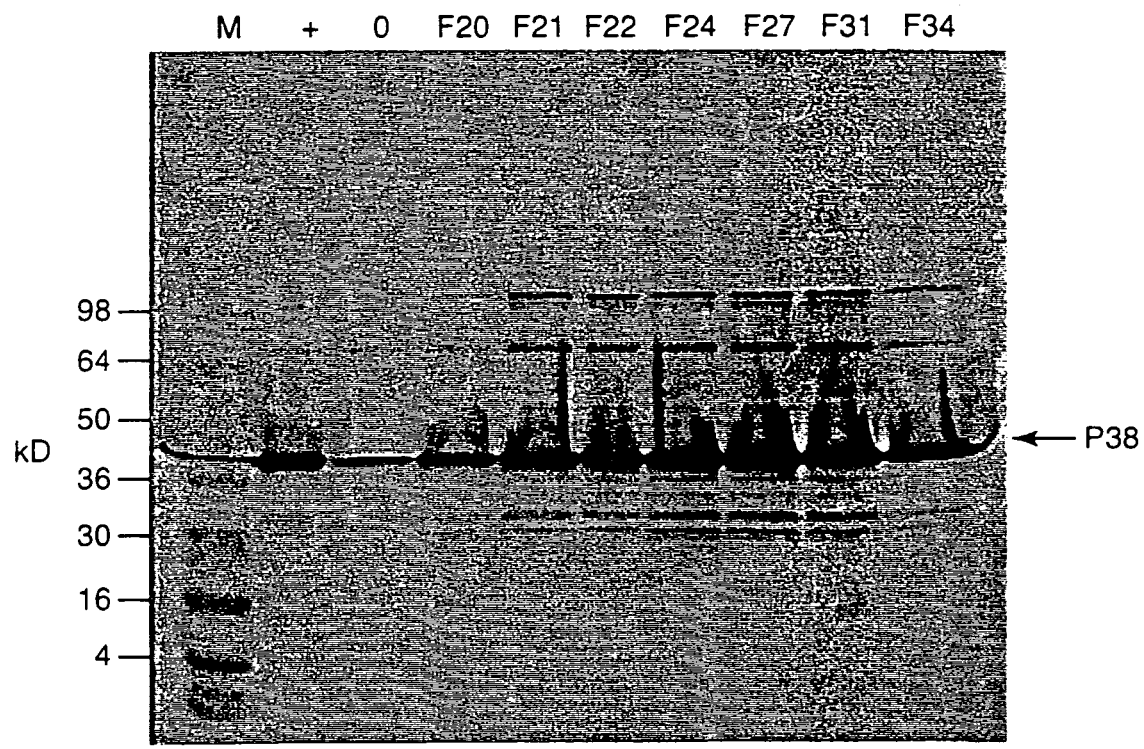
FIG. 12 illustrates a Western blot of immunoaffinity purified native RFC complex using anti-P38 IgG (panel A) or anti-P55 IgG (panel B). Immunoaffinity purification was carried out using rabbit anti P55 IgG as the capture reagent. Fractions are labeled as follows: +, positive control; 0, wash. F20-F34 refer to fractions eluted at pH 2.8 from the column.
Figure 12B:
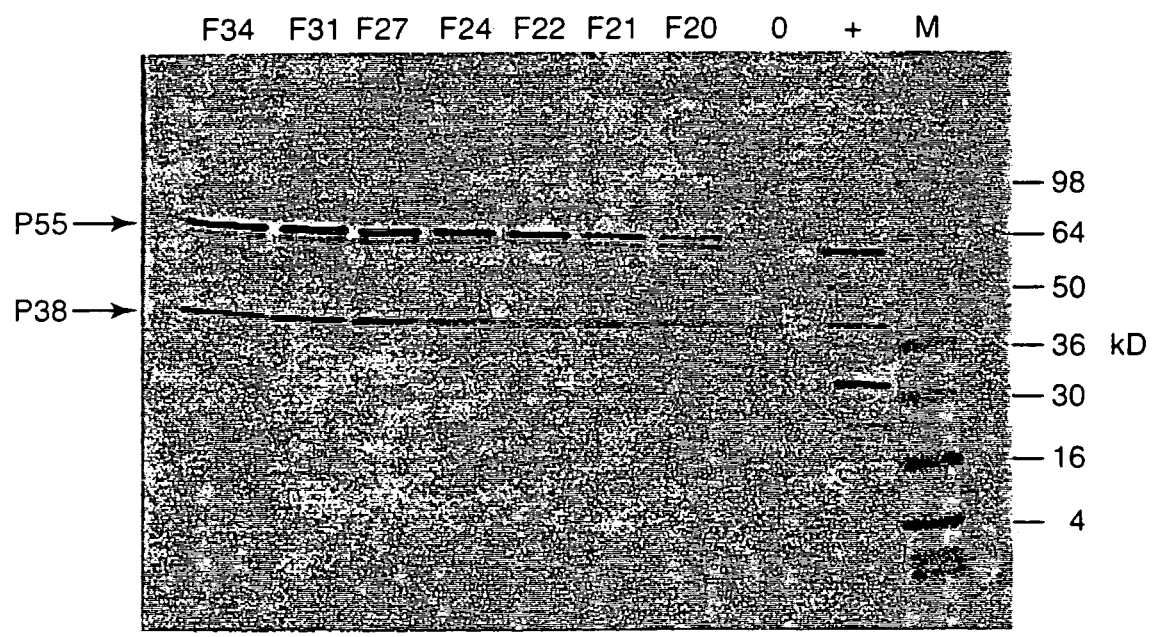
Figure 13:
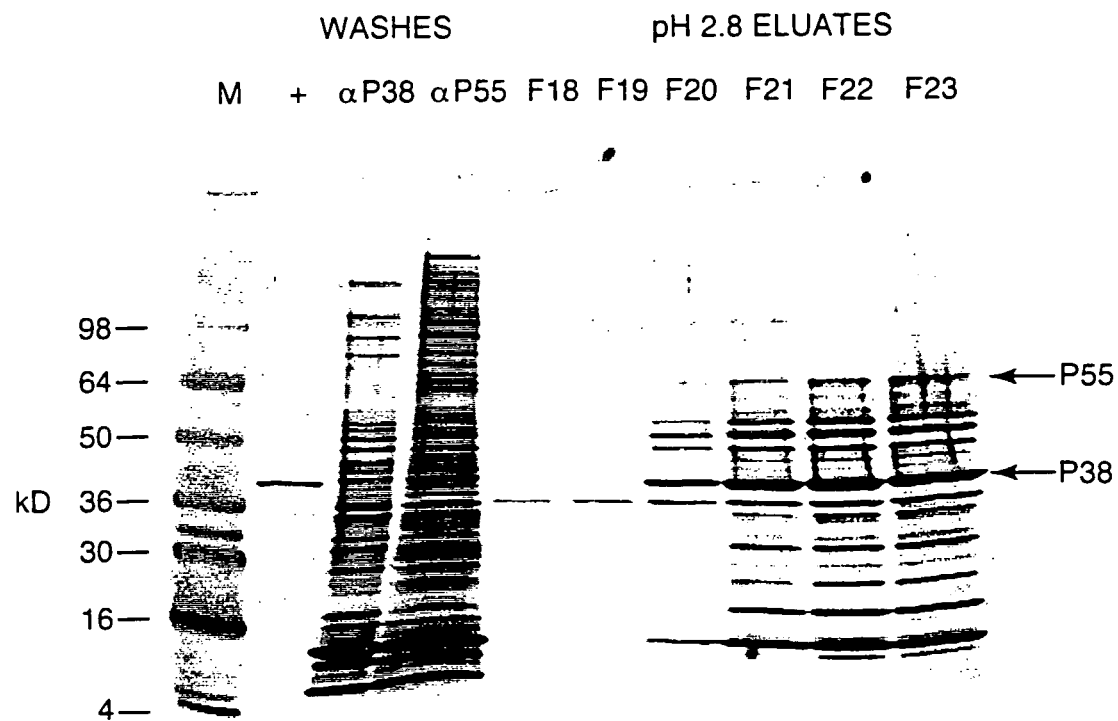
FIG. 13 illustrates a protein gel of immunoaffinity purified native RFC complex. Immunoaffinity purification was carried out using rabbit anti. P55 IgG as the capture reagent. Fractions are labeled as follows: +, positive P38 control; α-P38 (unrelated expt.) or α-P55 column washes (present expt.). F18-F23 refer to fractions eluted at pH 2.8 from the column.

Antibodies were raised in rabbits against the P55 and P38 subunits. The native RFC complex was purified from *P. furiosus* extracts by immunoaffinity chromatography using either immobilized anti-P55 or anti-P38 IgG. Western blot analysis of immunoaffinity-purified RFC complex shows the presence of both subunits regardless of the capture antibody (FIG. 12), indicating that P38 and P55 form a complex in *P. furiosus* as do the large and small RFC subunits in eukaryotes. The protein composition of one native RFC preparation is shown in FIG. 13. In addition to P55 and P38, there are other protein bands present which have not yet been identified.

Figure 15:
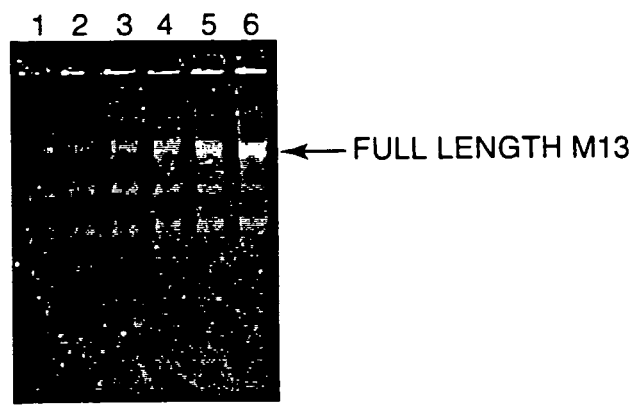
FIG. 15 illustrates that native clamp loader further stimulates primer extension by Pfu in the presence of PCNA. Primer extension reactions were carried out as described in the Detailed Description of Embodiments of the Invention.
Figure 14:
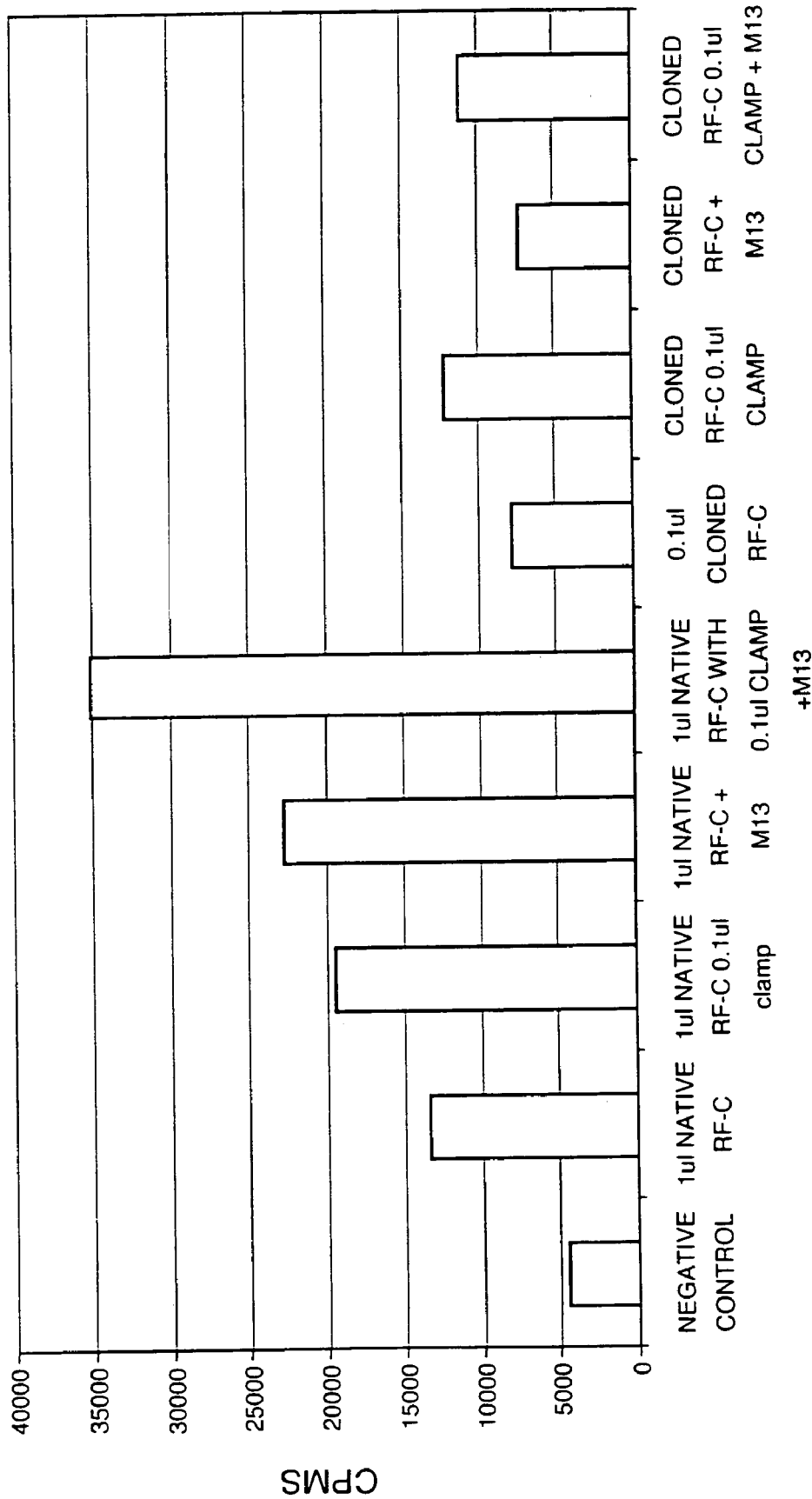
FIG. 14 illustrates the ATPase activity of native and recombinant RFC. Positions on the TLC plate containing the released radioactive phosphate were excised and counted in a scintillation counter.

The ATPase activity of the RFC preparations was tested (FIG. 14). RFC subunits are ATPases. That is, they convert ATP to ADP and phosphate. RFC complex in eukaryotes is known to load PCNA clamp onto DNA in a process that typically requires the conversion of ATP to ADP and phosphate. Recombinant P55 and P38 exhibited ATPase activity when assayed separately. A mixture of P55 and P38 subunits was also found to exhibit ATPase activity that increased in the presence of PCNA, but not in the presence of primed M13 DNA. In contrast, native RFC purified by immunoaffinity chromatography exhibited ATPase activity which was further stimulated by both PCNA and DNA. As the eukaryotic RFC complex is stimulated by both PCNA and DNA, it appears that the native RFC preparation is fully functional, while the mixture of recombinant P55 and P38 may be only partially active. This conclusion was supported by primer extension studies in which a native RFC preparation from *P. furiosus* (Immunopurified) was shown to enhance the yield of full-length products synthesized with Pfu DNA polymerase in the presence of PCNA (FIG. 15). In contrast, a mixture of recombinant P55 and P38 with similar ATPase activity showed less enhancement of primer extension by Pfu+PCNA. It is presently unknown whether the difference in activity between native and recombinant RFC is due to differences in the P55:P38 ratios or protein modification, or to the absence of additional proteins present in the native RFC preparations. One skilled in the art could determine a solution by attempting different ratios of P55 to P38 or different reaction conditions, or by adding additional protein factors such as the ones present in a native RFC preparation.

3. RFA.

The large subunit of eukaryotic RFA was used to search the archaeal protein databases with PSI-BLAST. Hits to archaeal sequences were examined. The inventors aligned corresponding sequences to identify the putative start and stop codons of the RFA sequence in the incomplete P. furiosus genome sequence. P. furiosus rfa sequence was PCR amplified and cloned into the pALnEK vector. The DNA sequence and translated protein sequences are shown in FIGS. 16 and 17. The apparent molecular weight of the expressed fully denatured protein was consistent with the size expected from the translated DNA sequence (41 kDa).

Figure 18:
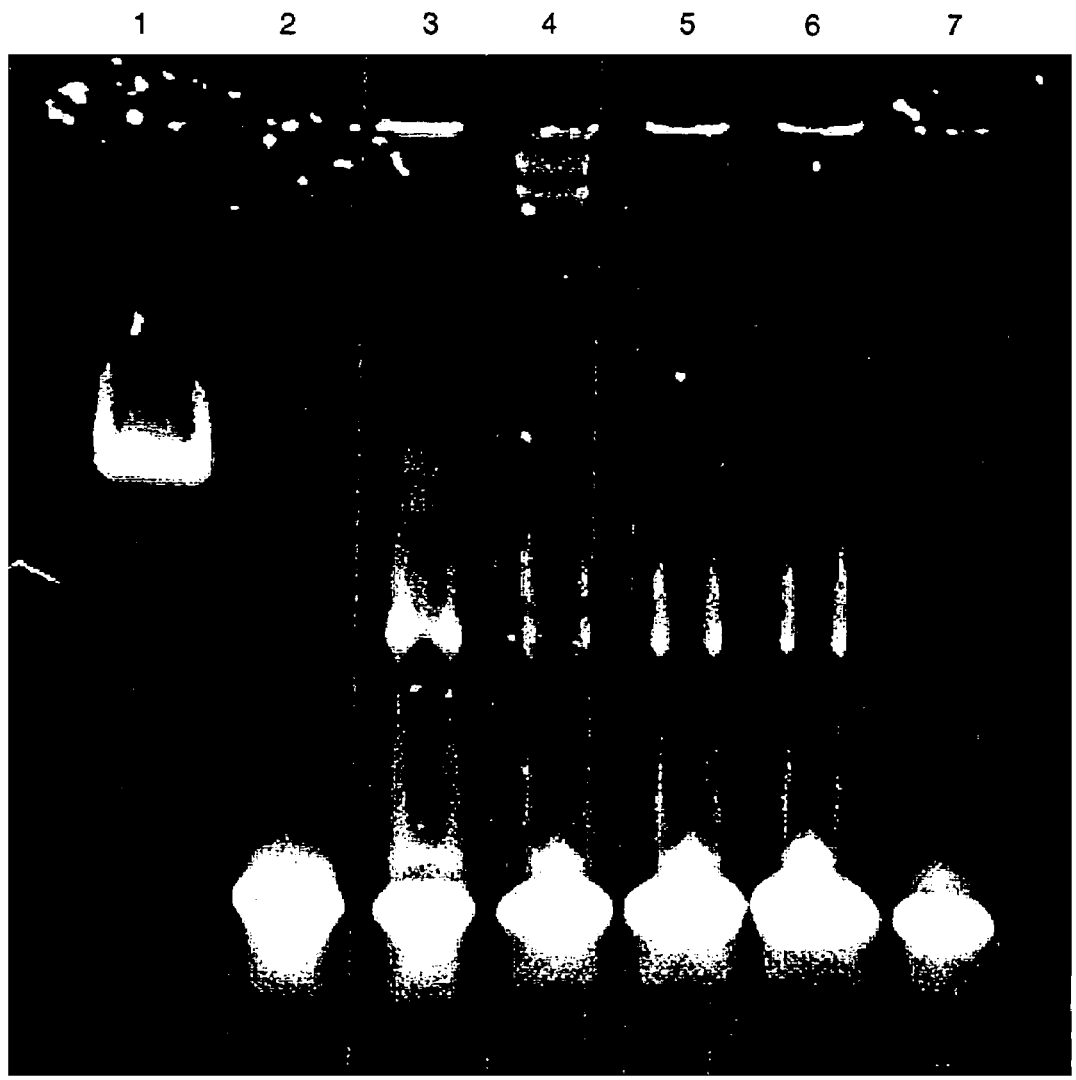
FIG. 18 illustrates a gel shift assay that demonstrates single-stranded DNA binding activity of P. furiosus RFA. 50 ng of a 38-mer oligo was incubated with E. coli SSB (lane 1), water (lane 2), or P. furiosus RFA (lanes 3-7) in TE buffer (lanes 1-3), 1×cloned Pfu buffer (lane 4), 50 mM Tris pH 8.5, 25 mM KCl, 2 mM $MgCl_2$ (lane 5), 50 mM Tris pH 8.5, 25 mM KCl, 5 mM $MgCl_2$ (lane 6), or 50 mM Tris pH 8.5, 25 mM KCl, 2 mM $ZnCl_2$ (lane 7). Samples were incubated at 95° C. for 10 minutes, followed by 72° C. for 2 minutes prior to loading on a 4-20% acrylamide gradient gel in 1×TBE buffer. Bands were visualized by SYBR green staining and UV illumination.

To assess function, P. furiosus RFA was tested for single-stranded DNA binding activity in a gel shift assay (FIG. 18). When RFA was incubated with a 38 base oligonucleotide, the migration of a percentage of the DNA was reduced, indicating that RFA does exhibit single stranded DNA binding activity. In comparison, E. coli SSB was found to completely retard the oligo. The weaker single stranded DNA binding activity exhibited by P. furiosus RFA may be explained by use of insufficient protein, the presence of the CBP tag, or the use of suboptimal reaction conditions. The degree of migration of the oligo is related to the mass of the protein-DNA complex and the formation of protein multimers. E. coli SSB is known to form tetramers, but it is presently unknown whether P. furiosus RFA produces multimers as well.

Figure 19:
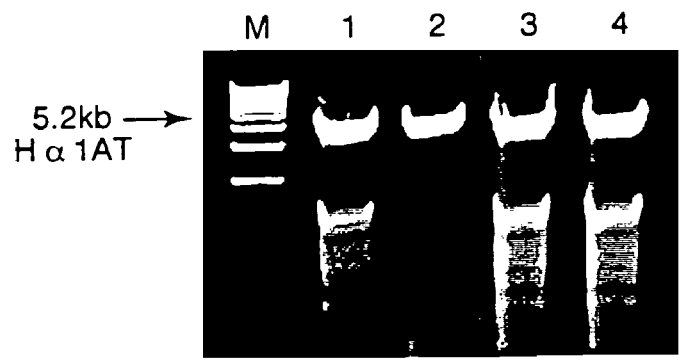
FIG. 19 illustrates an increase in amplification specificity with RFA using cloned Pfu+PEF (Pfu Turbo™ DNA polymerase (Stratagene)) (5.2 kb system).
Figure 20:
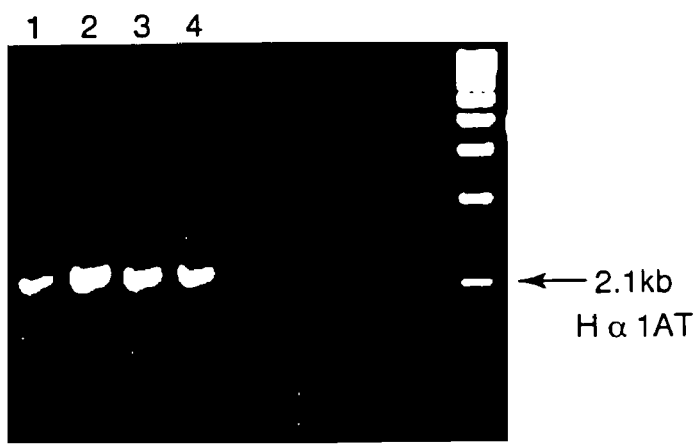
FIG. 20 illustrates an increase in product yield using RFA in combination with cloned Pfu Turbo™ DNA polymerase (2.1 kb system).
Figure 21:
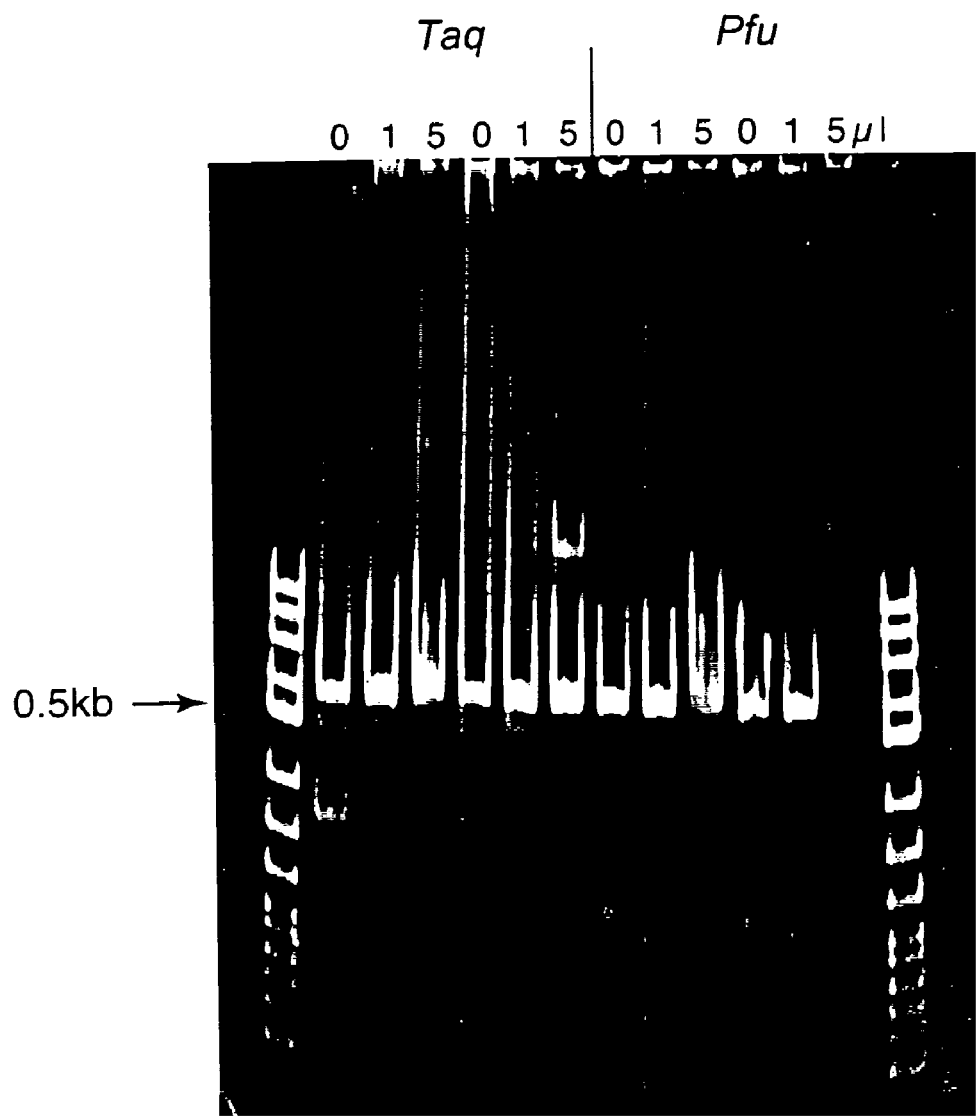
FIG. 21 illustrates an increase in yield and amplification specificity with RFA and E. coli SSB using Taq and Pfu DNA polymerases (0.5 kb system).

The addition of P. furiosus RFA to amplifications carried out with Pfu and Taq DNA polymerases was shown to increase amplification specificity (FIGS. 19 and 21) and PCR product yield (FIGS. 20 and 21). The conditions were as described in Section 6 above. In FIG. 21, P. furiosus RFA produced effects which were similar to those generated by E. coli single-stranded DNA binding protein (SSB; Stratagene's Perfect Match), including increased yield and amplification specificity and retardation of DNA migration at excess concentrations (5 µl). No evaluation of the relative performances of P. furiosus RFA and E. coli single-stranded DNA binding protein in PCR has been made; however, the increased thermostability of RFA should provide an additional benefit in temperature cycling.

4. Helicase.

Cells contain multiple helicases with specialized roles in a number of processes including replication, DNA repair, recombination, transcription, and translation. Known helicases have been classified into five families based upon sequence homology. Mechanistically, there are 2 classes of helicases depending upon whether unwinding requires a 3' overhang (3'-5' polarity) or a 5' overhang (5'-3' polarity), which is characteristic of helicases functioning in DNA replication. Archaeal replicative helicases were identified by identifying as many ORFs as possible in archaeal genomes that exhibited homology to any known eukaryotic helicase, regardless of specific metabolic role. No putative helicase sequences were excluded because helicase function between archaea and eukaryotes may be different. Moreover, the eukaryotic replicative helicase has not been conclusively identified. Using eukaryotic helicases, a PSI-BLAST search in the archaeal protein databases was conducted.

Eight putative helicases meeting the criteria were selected for analysis. The incomplete P. furiosus genome sequence was examined to identify the putative start and stop codons of these sequences and to design PCR primers for cloning. The DNA sequences are shown in FIGS. 22-28, and 40, respectively; the translated protein sequences are shown in FIGS. 29-35, and 41, respectively. The apparent molecular weights of the expressed proteins were consistent with the sizes expected from the translated DNA sequence (see figure description of FIGS. 29-35). Future corrections in the incomplete P. furiosus genome sequence may define alternative start and stop sites.

Helicases act to displace the complimentary strand of DNA or RNA to uncover template for DNA polymerases, RNA polymerases, accessory factors, and repair factors. Helicases melt the complimentary strand in a process coupled to hydrolysis of ribo- or deoxyribonucleotides. Most helicases displace either a 5' overhang or a 3' overhang, but some helicases displace both templates or utilize different templates under different reaction conditions. Typically, a helicase will utilize one or more nucleotide triphosphates preferentially. To assess the function of the identified eight helicases, recombinant helicases were tested for ATPase activity. The ribonucleotide ATP was used, although other ribo- or deoxyribonucleotides may serve as the preferred substrate. The resulting recombinant proteins were incubated with ATP, and phosphate was detected after separation by TLC. The results in FIGS. 36 and 37 demonstrate that all eight recombinant helicases exhibit ATPase activity.

Figure 38A:
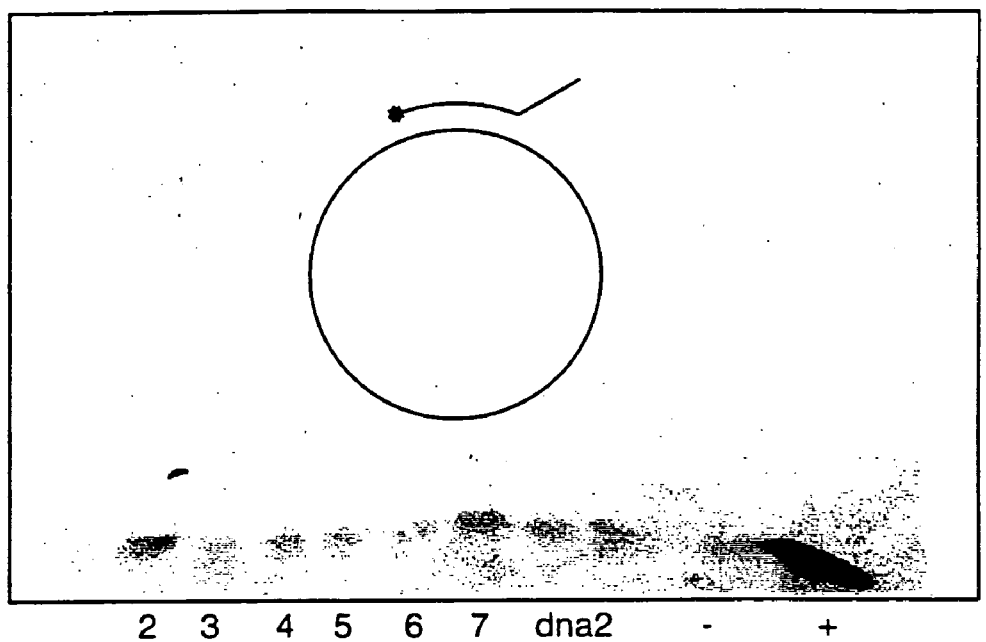
FIG. 38 illustrates the helicase displacement of bound oligos. Radioactively labeled oligonucleotides with a 3' overhang (A) or a 5' overhang (B) were annealed to M13mp18. The reactions were incubated with 0.5 μl of putative Pfu helicases 3-7 and Pfu helicase dna2 in 50 mM Tris pH 8.5, 25 mM KCl, 5 mM $MgCl_2$ and 5 mM ATP for 30 minutes at 55° C. 1 μl of Pfu helicase 2 was used in an identical reaction. The positive control was generated by thermally melting the annealed oligo prior to loading. The negative control was incubated with water. The samples were run on 4-20% gradient acrylamide gels in 1×TBE. The gels were dried and exposed to x-ray film.
Figure 38B:
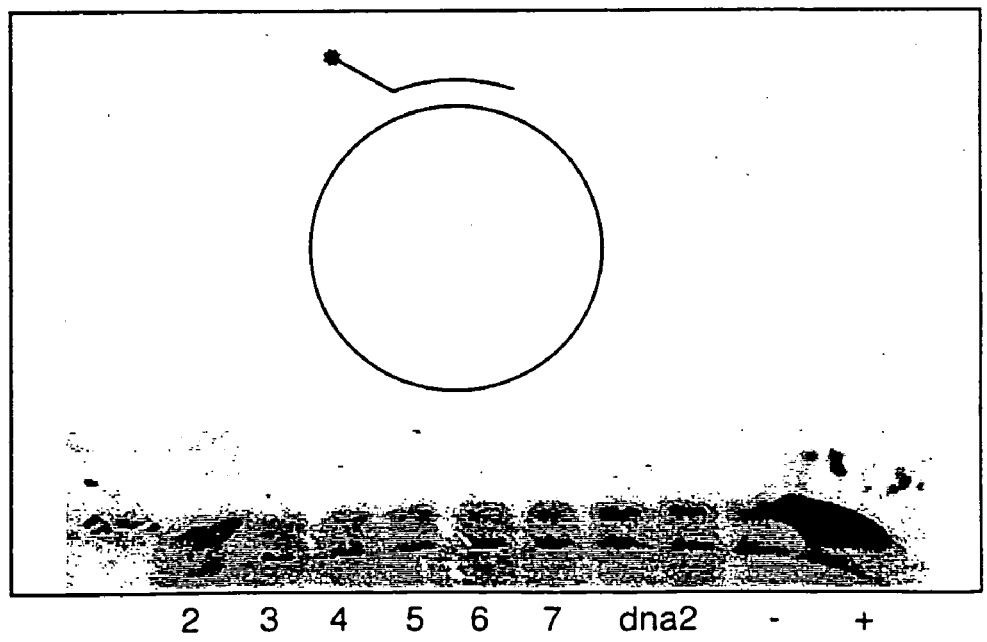
Figure 39:
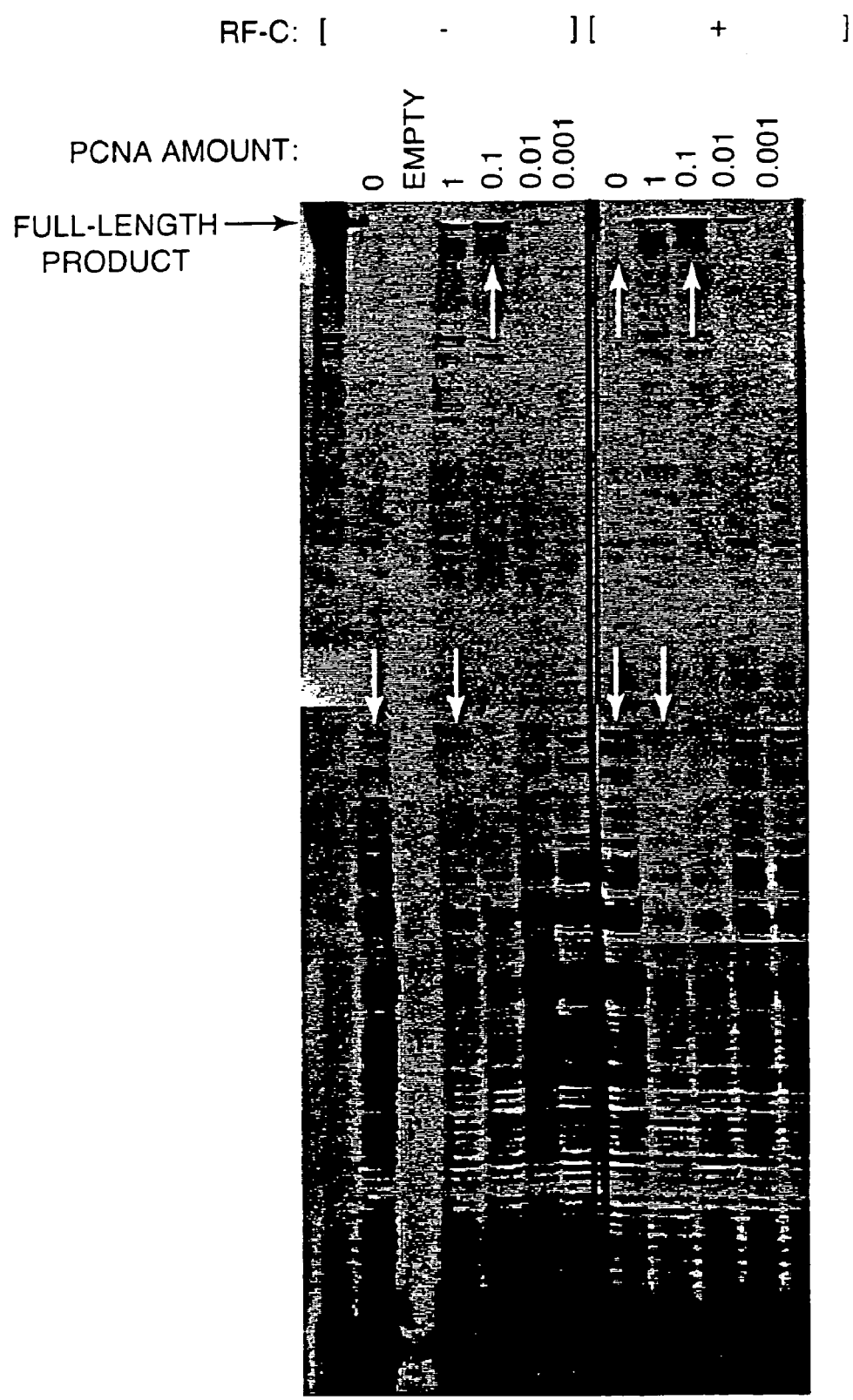
FIG. 39 illustrates the enhancement of Pfu processivity with Pfu PCNA and RF-C.

Eight recombinant helicases were tested for helicase activity. The templates used included labeled oligonucleotides annealed to single-stranded M13 mp18 DNA. The oligos had either 5' or 3' non-complementary ends. As shown in FIG. 38, helicase 2 was able to displace oligos from both templates. This helicase also melted a template which had non-complementary 5' and 3' ends (data not shown). Such a forked template mimics the "bubble" formed by the replication fork. In addition, helicase 7 displaced the oligo with a free 3' end (FIG. 38). The lack of detectable oligo displacement does not necessarily mean that the rest of the enzymes are not helicases, because lack of helicase activity may be attributed to the use of suboptimal buffers or reaction conditions, the presence of the N-terminal CBP tag, or the use of insufficient amounts of recombinant protein. Preliminary experiments showed that the addition of diluted preparations of helicase 2 or helicase dna2 to PCRs in combination with Pfu DNA polymerase can lead to increased PCR product yield (data not shown).

All documents mentioned in this application, including but not limited to, articles, books, reviews, patents and patent applications, are hereby incorporated by reference in their entirety into this specification.

REFERENCES

1. European Patent No. EP0870832, published on Oct. 14, 1998, invented by Kato, I., et al.; and assigned to Takara Shuzo Co.
2. International Patent Application Publication No. WO 98/42860, published on Oct. 1, 1998, invented by Hogrefe, H. and Hansen, C.; and assigned to Stratagene.
3. U.S. Pat. No. 5,866,395 issued on Feb. 2, 1999, to Eric J. Mathur.
4. U.S. Pat. No. 5,545,552 issued on Aug. 13, 1996, to Eric J. Mathur.

5. Baker, T. A. and Bell, S. P., "Polymerase and the Replisome: Machines within Machines" Cell 92:295-305 (1998).
6. Bult, C. J., et al, "Complete Genome Sequence of the Methanogenic Archeon, *Methoanccoccus jannaschii*" Science 273:1066-1073 (1996).
7. Chedin, F., et al., "Novel Homologs of Replication Protein A in Archaea: Implications for the Evolution of ssDNA-Binding Proteins" TIBS 23:273-277 (1998).
8. Cline, J., et al., "PCR Fidelity of Pfu DNA Polymerase and Other Thermostable DNA Polymerases" Nucl. Acids Res. 24: 3546-3551 (1996).
9. Edgell, D. R. and Doolittle, W. F., "Archaea and the Origin(s) of DNA Replication Proteins" Cell 89:995-998 (1997).
10. Kelly, T. J. et al., "Identification and Characterization of a single-stranded DNA Binding Protein from the archeon *Methanococcus jannaschii*" PNAS 95: 14634-14639 (1998).
11. Keohavong, P. and Sandhu, D. K., "Effects of the T4 Bacteriophage Gene 32 Product on the Efficiency and Fidelity of DNA Amplification Using T4 DNA Polymerase" Gene 144:5358 (1994).
12. Lundberg, K. S., et al., "High-Fidelity Amplification Using a Thermostable DNA Polymerase Isolated from *Pyrococcus furiosus*" Gene 108:1-6 (1991).
13. McHenry, C. S., et al., "A DNA Polymerase III Holoenzyme-like Subassembly from an Extreme Thermophilic Eubacterium" J. Mol. Biol. 272:178-189 (1997).
14. Mathur, E., et al., ffhe DNA Polymerase Gene from the Hyperthermophilic Marine Archaeabacterium, *Pyrococcus furiosus*, Shows Sequence Homology with α-like DNA Polymerases" Nucl. Acids, Res. 19: 6952 (1991).
15. Uemori, T., et al., "A Novel DNA Polymerase in the Hyperthermophilic Archeon, *Pyrococcus furiosus*: Gene Cloning, Expression, and Characterization" Genes to Cells 2:499-512 (1997).

---

What is claimed is:

1. An isolated and purified polynucleotide encoding an archaeal replication factor A ("RFA"), wherein the polynucleotide is selected from the group consisting of: a polynucleotide comprising the nucleotide sequence set forth in FIG. 16 (SEQ ID NO: 65); and a polynucleotide encoding the amino acid sequence set forth in FIG. 17 (SEQ ID NO: 66).

2. The polynucleotide of claim 1, wherein the polynucleotide is cDNA.

3. The polynucleotide of claim 1, wherein the polynucleotide is mRNA.

4. A vector comprising the polynucleotide of claim 1.

5. The vector of claim 4, wherein the vector is a plasmid.

6. The vector of claim 4, wherein the vector is a bacteriophage.

7. The vector of claim 4, wherein the vector is a retrovirus.

8. The vector of claim 4, wherein the vector is an adenovirus.

9. An isolated host cell comprising the vector of claim 4.

10. The isolated host cell of claim 9, wherein the isolated host cell is a prokaryotic cell.

11. The isolated host cell of claim 9, wherein the isolated host cell is a eukaryotic cell.

12. A method for producing replication accessory factors comprising: expressing the polynucleotide of the vector of claim 4 in a host cell; and purifying the expressed product.

13. The method of claim 12, wherein the host cell is a prokaryotic cell.

14. The method of claim 12, wherein the host cell is a eukaryotic cell.

15. An isolated and purified polynucleotide encoding an archaeal replication factor A ("RFA") comprising: (a) a polynucleotide comprising the nucleotide sequence set forth in FIG. 16 (SEQ ID NO: 65) or the nucleotide sequence of FIG. 16 starting with nucleotide 7; (b) a polynucleotide encoding the amino acid sequence set forth in FIG. 17 (SEQ ID NO: 66) or the amino acid sequence of FIG. 17 starting with amino acid 3; or (c) a polynucleotide encoding an amino acid sequence possessing 95% sequence identity to SEQ ID NO: 66, wherein the encoded amino acid sequence binds to and stabilizes single stranded DNA.

16. The polynucleotide of claim 15, wherein the polynucleotide is cDNA.

17. The polynucleotide of claim 15, wherein the polynucleotide is mRNA.

18. A vector comprising the polynucleotide of claim 15.

19. The vector of claim 18, wherein the vector is a plasmid.

20. The vector of claim 18, wherein the vector is a bacteriophage.

21. The vector of claim 18, wherein the vector is a retrovirus.

22. The vector of claim 18, wherein the vector is an adenovirus.

23. An isolated host cell comprising the vector of claim 18.

24. The isolated host cell of claim 23, wherein the isolated host cell is a prokaryotic cell.

25. The isolated host cell of claim 23, wherein the isolated host cell is a eukaryotic cell.

26. A method for producing replication accessory factors comprising:
expressing the polynucleotide of the vector of claim 18 in a host cell; and
purifying the expressed product.

27. The method of claim 26, wherein the host cell is a prokaryotic cell.

28. The method of claim 26, wherein the host cell is a eukaryotic cell.

* * * * *

UNITED STATES PATENT AND TRADEMARK OFFICE
CERTIFICATE OF CORRECTION

PATENT NO. : 7,442,766 B2  Page 1 of 1
APPLICATION NO. : 10/828924
DATED : October 28, 2008
INVENTOR(S) : Hogrefe et al.

It is certified that error appears in the above-identified patent and that said Letters Patent is hereby corrected as shown below:

On the Title page, Item (56), under "Other Publications", delete "9959-998." and insert -- 995-998. --, therefor.

Signed and Sealed this

Twenty-seventh Day of January, 2009

JOHN DOLL
*Acting Director of the United States Patent and Trademark Office*

SEQUENCE LISTING

```
<160> NUMBER OF SEQ ID NOS: 84

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Zinc finger
      motif
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MISC_FEATURE
<222> LOCATION: (5)..(8)
<223> OTHER INFORMATION: Xaa is any amino acid
<220> FEATURE:
<221> NAME/KEY: MISC_FEATURE
<222> LOCATION: (10)..(24)
<223> OTHER INFORMATION: Xaa is any amino acid
<220> FEATURE:
<221> NAME/KEY: MISC_FEATURE
<222> LOCATION: (26)..(27)
<223> OTHER INFORMATION: Xaa is any amino acid
<220> FEATURE:
<221> NAME/KEY: VARIANT
<222> LOCATION: (5)..(8)
<223> OTHER INFORMATION: This region may encompass 2-4 residues
<220> FEATURE:
<221> NAME/KEY: VARIANT
<222> LOCATION: (10)..(24)
<223> OTHER INFORMATION: This region may encompass 12-15 residues
<220> FEATURE:
<221> NAME/KEY: MISC_FEATURE
<222> LOCATION: (4)
<223> OTHER INFORMATION: Xaa is His or Cys
<220> FEATURE:
<221> NAME/KEY: MISC_FEATURE
<222> LOCATION: (9)
<223> OTHER INFORMATION: Xaa is His or Cys
<220> FEATURE:
<221> NAME/KEY: MISC_FEATURE
<222> LOCATION: (25)
<223> OTHER INFORMATION: Xaa is His or Cys
<220> FEATURE:
<221> NAME/KEY: MISC_FEATURE
<222> LOCATION: (28)
<223> OTHER INFORMATION: Xaa is His or Cys
```

```
<400> SEQUENCE: 1

Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa
             20                  25

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 2
gacgacgaca agatgagcga agagattaga gaa                          33

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 3
ggaacaagac ccgttcactt cttcccaatt agggt                        35

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 4
gacgacgaca agatgccaga gcttccctgg gta                          33

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 5
ggaacaagac ccgttcactt tttaagaaag tcaaa                        35

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 6
gacgacgaca agatgccatt cgaaatagtc tttg                         34

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 7
ggaacaagac ccgttcactc ctcaaccctt ggggcta                      37
```

```
<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 8
actacagcgg ctttgg                                                     16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 9
ctttccgaca ccaggg                                                     16

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 10 gacgacgcaca agatgatcat gagtgcattt acaaaagaag aaataatc                 48

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 11
ggaacaagac ccgttcacat cacccccaat tcttccaatt ccc                       43

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 12 gacgacgcaca agatgaacat aaagagcttc ataaacaggc tt                       42

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 13
ggaacaagac ccgttcaaat gctatccttc gttagcacaa cata                      44

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Primer
```

<400> SEQUENCE: 14
gacgacgaca agatgattga ggagctgttc aagggattag agagtgaaat                50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 15
ggaacaagac ccgttcatct ttttacggca aatgcgaatt cttctccctt                50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 16
gacgacgaca agatgttaat agttgtaaga ccaggaagaa aaagaatga                 50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 17
ggaacaagac ccgttcatcg tctctcaccc ttcaaaattt ttccttcttc                50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 18
gacgacgaca agatgcacat attgataaaa aaggcaataa aagagagatt                50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 19
ggaacaagac ccgtctattc ccaaaacttt ctagtttgga tgtagtgttt                50

<210> SEQ ID NO 20
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 20
gacgacgaca agatgttatt aaggagagac ttaatacagc ctaggatat                 49

<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 21
ggaacaagac ccgtctactc ctcatcctct atatatgggg cagttatta         49

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 22
gacgacgaca agatgctcat gaggccagtg aggctaatga tagctgatg          49

<210> SEQ ID NO 23
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 23
ggaacaagac ccgtctagct taacttaagt aaatgcctat ctttcttct          49

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 24
gacgacgaca agatgatcga aggttacgaa attaaactag ctgttgtaac         50

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 25
ggaacaagac ccgttcaaaa acctttccca ggtatgcggg ggtcgct            47

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 26
gacgacgaca agatgagggt tgatgagctg agagttgatg agaggata           48

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 27
ggaacaagac ccgttcaaga tttgagaaag taatcaaggg tacttttct                50

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 28
gacgacgaca agatggacag ggaggagatg attgagagat ttgcaaac                 48

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 29
ggaacaagac ccgttcagac ggttttgtag taaccactct ctggcat                  47

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 30
aagacctgct gcggaactac ttttg                                          25

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 31
actgctgcag cagttaggga tgagcg                                         26

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 32
gacgacgaca agatgaacga aggcatcaaa taaagcttga cgag                     44

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 33
ggaacaagac ccgtttagat caacctgctc actcttaagg ga                       42

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 34
gacgacgaca agatgggtgt cccaattggt gagattatac caagaaaag         49

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 35
ggaacaagac ccgtttatct cttgaaccaa ctttcaaggg ttgattgttt tccact         56

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 36
gatgaaagag ggatagat         18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 37
atctccagtt agacagct         18

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 38
ggttttccca gtcacgacgt tgtaaaacga cggccagtgc         40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 39
ggttttccca gtcacgacgt tgtaaaacga cggccagtgc         40

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 40
ggttttccca gtcacgacgt tgtaaaacga cggccagt                              38

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gagagaattc ataatgataa ggaggaaaaa attatgatcc tggacgatga ctacatcacc      60

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 42
cacaagggct actggttgcc gatt                                             24

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 43
cagggcattg acagcagtct tctcctcagg                                       30

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 44
cacaagggct actggttgcc gatt                                             24

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 45
agcttcccaa cgtgatcgcc t                                                21

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 46
ctcagatatg gccaaagatc tatacacacc                                       30
```

```
<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 47
agcttcccaa cgtgatcgcc tt                                              22

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 48
gaggagagca ggaaaggtgg aac                                             23

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 49
gaaaatagga gctcagctgc ag                                              22

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 50
gaggagagca ggaaaggtgg aac                                             23

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 51
gctgggagaa gacttcactg g                                               21

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 52
gacagtcact ccggcccg                                                   18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 53
cgacgactcg tggagccc                                                        18

<210> SEQ ID NO 54
<211> LENGTH: 36
<212> TYPE: PRT
<213> ORGANISM: Unknown Organism
<220> FEATURE:
<223> OTHER INFORMATION: Description of Unknown Organism: N-terminal
      sequence
<220> FEATURE:
<221> NAME/KEY: MISC_FEATURE
<222> LOCATION: (23)
<223> OTHER INFORMATION: Xaa is His or Ile

<400> SEQUENCE: 54

Pro Phe Glu Ile Val Phe Glu Gly Ala Lys Glu Phe Ala Gln Leu Ile
  1               5                  10                  15

Asp Thr Ala Ser Lys Leu Xaa Asp Glu Ala Ala Phe Lys Val Thr Glu
                 20                  25                  30

Asp Gly Met Arg
         35

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 55
gatgaaagag ggatagat                                                        18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 56
atctccagtt agacagct                                                        18

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 57
cacaagggct actggttgcc gatt                                                 24

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 58
cagggcattg acagcagtct tctcctcagg                                           30
```

<210> SEQ ID NO 59
<211> LENGTH: 750
<212> TYPE: DNA
<213> ORGANISM: Artificial Sequence
<220> FEATURE:
<223> OTHER INFORMATION: Description of Artificial Sequence: Recombinant PCNA

<400> SEQUENCE: 59

```
atgccattcg aaatagtctt tgaaggtgca aaagagtttg cccaacttat agacaccgca      60
agtaagttaa tagatgaggc cgcgtttaaa gttacagaag atgggataag catgagggcc     120
atggatccaa gtagagttgt cctgattgac ctaaatctcc cgtcaagcat atttagcaaa     180
tatgaagttg ttgaaccaga acaattgga gttaacatgg accacctaaa gaagatccta     240
aagagaggta aagcaaagga caccttaata ctcaagaaag gagaggaaaa cttcttagag     300
ataacaattc aaggaactgc aacaagaaca tttagagttc cctaataga tgtagaagag     360
atggaagttg acctcccaga acttccattc actgcaaagg ttgtagttct ggagaagtc     420
ctaaaagatg ctgttaaaga tgcctctcta gtgagtgaca gcataaaatt tattgccagg     480
gaaaatgaat ttataatgaa ggcagaggga gaaacccagg aagttgagat aaagctaact     540
cttgaagatg agggattatt ggacatcgag gttcaagagg agacaaagag cgcatatgga     600
gtcagctatc tctccgacat ggttaaagga cttggaaagg ccgatgaagt tacaataaag     660
tttggaaatg aaatgcccat gcaaatggag tattacatta gagatgaagg aagacttaca     720
ttcctactag ccctagggt tgaggagtga                                       750
```

<210> SEQ ID NO 60
<211> LENGTH: 249
<212> TYPE: PRT
<213> ORGANISM: Artificial Sequence
<220> FEATURE:
<223> OTHER INFORMATION: Description of Artificial Sequence: Recombinant PCNA

<400> SEQUENCE: 60

```
Met Pro Phe Glu Ile Val Phe Glu Gly Ala Lys Glu Phe Ala Gln Leu
  1               5                  10                  15

Ile Asp Thr Ala Ser Lys Leu Ile Asp Glu Ala Ala Phe Lys Val Thr
                 20                  25                  30

Glu Asp Gly Ile Ser Met Arg Ala Met Asp Pro Ser Arg Val Val Leu
             35                  40                  45

Ile Asp Leu Asn Leu Pro Ser Ser Ile Phe Ser Lys Tyr Glu Val Val
         50                  55                  60

Glu Pro Glu Thr Ile Gly Val Asn Met Asp His Leu Lys Lys Ile Leu
 65                  70                  75                  80

Lys Arg Gly Lys Ala Lys Asp Thr Leu Ile Leu Lys Lys Gly Glu Glu
                 85                  90                  95

Asn Phe Leu Glu Ile Thr Ile Gln Gly Thr Ala Thr Arg Thr Phe Arg
            100                 105                 110

Val Pro Leu Ile Asp Val Glu Glu Met Glu Val Asp Leu Pro Glu Leu
        115                 120                 125

Pro Phe Thr Ala Lys Val Val Val Leu Gly Glu Val Leu Lys Asp Ala
    130                 135                 140

Val Lys Asp Ala Ser Leu Val Ser Asp Ser Ile Lys Phe Ile Ala Arg
145                 150                 155                 160

Glu Asn Glu Phe Ile Met Lys Ala Glu Gly Glu Thr Gln Glu Val Glu
                165                 170                 175
```

```
Ile Lys Leu Thr Leu Glu Asp Glu Gly Leu Leu Asp Ile Glu Val Gln
            180                 185                 190

Glu Glu Thr Lys Ser Ala Tyr Gly Val Ser Tyr Leu Ser Asp Met Val
            195                 200                 205

Lys Gly Leu Gly Lys Ala Asp Val Thr Ile Lys Phe Gly Asn Glu
    210                 215                 220

Met Pro Met Gln Met Glu Tyr Tyr Ile Arg Asp Glu Gly Arg Leu Thr
225                 230                 235                 240

Phe Leu Leu Ala Pro Arg Val Glu Glu
                245

<210> SEQ ID NO 61
<211> LENGTH: 4848
<212> TYPE: DNA
<213> ORGANISM: Artificial Sequence
<220> FEATURE:
<223> OTHER INFORMATION: Description of Artificial Sequence: Genomic RFC
      clone
<220> FEATURE:
<221> NAME/KEY: misc_feature
<222> LOCATION: (20)
<223> OTHER INFORMATION: n is a, t, c, g, other, or unknown
<220> FEATURE:
<221> NAME/KEY: misc_feature
<222> LOCATION: (43)
<223> OTHER INFORMATION: n is a, t, c, g, other, or unknown
<220> FEATURE:
<221> NAME/KEY: misc_feature
<222> LOCATION: (107)..(108)
<223> OTHER INFORMATION: n is a, t, c, g, other, or unknown
<220> FEATURE:
<221> NAME/KEY: misc_feature
<222> LOCATION: (139)
<223> OTHER INFORMATION: n is a, t, c, g, other, or unknown
<220> FEATURE:
<221> NAME/KEY: misc_feature
<222> LOCATION: (3822)
<223> OTHER INFORMATION: n is a, t, c, g, other, or unknown
<220> FEATURE:
<221> NAME/KEY: misc_feature
<222> LOCATION: (4483)
<223> OTHER INFORMATION: n is a, t, c, g, other, or unknown
<220> FEATURE:
<221> NAME/KEY: misc_feature
<222> LOCATION: (4498)
<223> OTHER INFORMATION: n is a, t, c, g, other, or unknown
<220> FEATURE:
<221> NAME/KEY: misc_feature
<222> LOCATION: (4502)
<223> OTHER INFORMATION: n is a, t, c, g, other, or unknown
<220> FEATURE:
<221> NAME/KEY: misc_feature
<222> LOCATION: (4521)
<223> OTHER INFORMATION: n is a, t, c, g, other, or unknown
<220> FEATURE:
<221> NAME/KEY: misc_feature
<222> LOCATION: (4545)
<223> OTHER INFORMATION: n is a, t, c, g, other, or unknown
<220> FEATURE:
<221> NAME/KEY: misc_feature
<222> LOCATION: (4589)
<223> OTHER INFORMATION: n is a, t, c, g, other, or unknown
<220> FEATURE:
<221> NAME/KEY: misc_feature
<222> LOCATION: (4598)
<223> OTHER INFORMATION: n is a, t, c, g, other, or unknown
<220> FEATURE:
<221> NAME/KEY: misc_feature
<222> LOCATION: (4658)
<223> OTHER INFORMATION: n is a, t, c, g, other, or unknown
<220> FEATURE:
<221> NAME/KEY: misc_feature
<222> LOCATION: (4710)
<223> OTHER INFORMATION: n is a, t, c, g, other, or unknown
```

```
<220> FEATURE:
<221> NAME/KEY: misc_feature
<222> LOCATION: (4742)..(4743)
<223> OTHER INFORMATION: n is a, t, c, g, other, or unknown
<220> FEATURE:
<221> NAME/KEY: misc_feature
<222> LOCATION: (4753)..(4754)
<223> OTHER INFORMATION: n is a, t, c, g, other, or unknown
<220> FEATURE:
<221> NAME/KEY: misc_feature
<222> LOCATION: (4779)
<223> OTHER INFORMATION: n is a, t, c, g, other, or unknown
<220> FEATURE:
<221> NAME/KEY: misc_feature
<222> LOCATION: (4793)
<223> OTHER INFORMATION: n is a, t, c, g, other, or unknown
<220> FEATURE:
<221> NAME/KEY: misc_feature
<222> LOCATION: (4801)
<223> OTHER INFORMATION: n is a, t, c, g, other, or unknown
<220> FEATURE:
<221> NAME/KEY: misc_feature
<222> LOCATION: (4808)
<223> OTHER INFORMATION: n is a, t, c, g, other, or unknown
<220> FEATURE:
<221> NAME/KEY: misc_feature
<222> LOCATION: (4814)
<223> OTHER INFORMATION: n is a, t, c, g, other, or unknown
<220> FEATURE:
<221> NAME/KEY: misc_feature
<222> LOCATION: (4825)
<223> OTHER INFORMATION: n is a, t, c, g, other, or unknown

<400> SEQUENCE: 61
acccaaaatt gttattcagn tcaacggaga agacggagta ganttggaag gagcttatcc      60
agagaaatgt tcttagagaa gttactctca gctctcagct gatctanngt ttttccttct     120
tttcttctgt tcagttatng cctaggataa gcttaataat actttgatac ctttcttagt     180
ttaggtgtgt gagagtatga gcgaagagat tagagaagtt aaggttctag aaaaaccctg     240
ggttgagaag tatagacctc aaagacttga cgacattgta ggacaagagc acatagtgaa     300
aaggctcaag cactacgtca aaactggatc aatgccccac ctactcttcg caggcccccc     360
tggtgtcgga aagtgtctta ctggagatac caaagttata gctaatggcc aactctttga     420
acttggagaa cttgttgaaa agctttctgg ggggagattt ggaccaactc cagttaaagg     480
gctcaaagtt cttggaatag atgaggatgg aaagcttaga gagtttgaag tccaatacgt     540
ctacaaagat agaactgata ggttgataaa gataaaaact cagcttggca gggagcttaa     600
agtaactccg tatcacccac ttctagtgat tggagagaat ggcgaattaa agtggattaa     660
ggctgaagaa ctcaaacttg gcgacaagct tgcaataccg agctttctcc cacttataac     720
tggagaaaat ccccttgcag agtggcttgg ttactttatg ggaagtggct atgcttatcc     780
caagaattct gtcatcacgt tcactaacga agatccactc ataagacaac gctttatgga     840
actaacagag aaacttttcc ctgatgcaaa gataagggaa agaattcacg ctgatggaac     900
tccagaagtt tatgtggtat ctaggaaagc ttggagcctt gtaaactcta ttagcttaac     960 attaatacccc agggaggggt ggaaaggaat tcgttctttc cttagggcat attccgactg    1020
caatggtcgg attgaaagtg atgcaatagt tttatcaacc gataacaatg atatggccca    1080
gcagatagcc tatgctttag ccagctttgg aataatagct aaaatggatg gagaagatgt    1140
tattatctca ggctcggaca acatagagag gttcctaaat gagattggct ttagcaccca    1200
aagcaaactt aaagaagccc agaagctcat tagaaaaacc aatgtaagat ccgatggact    1260
aaagattaac tatgagctaa tctcctatgt aaaagacagg cttaggttaa atgtcaatga    1320
```

```
taaaagaaat ttgagctaca gaaatgcaaa ggagctttct tgggaactca tgaaagaaat    1380
ttattatcgc cttgaggaac tggagagact aaagaaggtc ttatcagaac ccatcttgat    1440
cgactggaat gaagtagcaa agaagagtga tgaagtaata gaaaaagcta aaattagagc    1500
agagaagctc ctagaataca taaaaggaga gagaaagcca agtttcaagg agtacattga    1560
gatagcaaaa gtccttggaa ttaacgttga acgtaccatc gaagctatga agatctttgc    1620
aaagagatac tcaagctatg ccgagattgg aagaaaactt ggaacttgga atttcaatgt    1680
aaaaacaatt cttgagagcg acacagtgga taacgttgaa atccttgaaa agataaggaa    1740
aattgagctt gagctcatag aggaaattct ttcggatgga aagctcaaag aaggtatagc    1800
atatctcatt ttcctcttcc agaatgagct ttactgggac gagataactg aagtaaaaga    1860
gcttagggga gactttataa tctatgatct tcatgttcct ggctaccaca actttattgc    1920
tgggaacatg ccaacagtag tccataacac tacagcggct ttggcccttg caagagagct    1980
tttcggcgaa aactggaggc ataacttcct cgagttgaat gcttcagatg aaagaggtat    2040
aaacgtaatt agagagaaag ttaaggagtt tgcgagaaca aagcctatag gaggagcaag    2100
cttcaagata attttccttg atgaggccga cgctttaact caagatgccc aacaagcctt    2160
aagaagaacc atggaaatgt ctcgagtaa cgttcgcttt atcttgagct gtaactacta    2220
ctccaagata attgaaccca tacagtctag atgtgcaata ttccgcttca gacctctccg    2280
cgatgaggat atagcgaaga gactaaggta cattgccgaa aatgagggct tagagctaac    2340
tgaagaaggt ctccaagcaa tactttacat agcagaagga gatatgagaa gagcaataaa    2400
cattctgcaa gctgcagcag ctctagacaa gaagatcacc gacgaaaacg tattcatggt    2460
agcgagtaga gctagacctg aagatataag agagatgatg cttcttgctc tcaaaggcaa    2520
cttcttgaag gccagagaaa agcttaggga gatacttctc aagcaaggac ttagtggaga    2580
agatgtacta gttcagatgc acaaagaagt cttcaacctg ccaatagagg agccaaagaa    2640
ggttctgctt gctgataaga taggagagta taacttcaga ctcgttgaag gggctaatga    2700
aataattcag cttgaagcac tcttagcaca gttcacccta attgggaaga agtgatgaag    2760
tatgccagag cttccctggg tagaaaaata caggccaaaa aagttaagtg aaattgtaaa    2820
ccaagaagag gctatagaga aagttagagc gtggatagag agctggttgc atggccaccc    2880
ccctaagaaa aaagccctat tattagcagg acccccaggg agcggaaaga caaccacagt    2940
ctacgctcta gcaaatgagt acaactttga agtcattgag ctcaacgcga gtgatgagag    3000
aacttatgaa aaaatctcca ggtatgttca agcagcatac actatggata tcctcggaaa    3060
gaggaggaag ataatcttcc tcgatgaagc agataatata gagcccagcg agctaagga    3120 aatcgcaaaa ctaattgata aggccaaaaa tccaataata atggctgcaa ataagtactg    3180
ggaagttcca aaagagatcc gagaaaaagc tgagctagta gagtacaaga ggttaaccca    3240
gagagatgta atgaatgcct taataaggat cctaaagagg gaaggtataa cagttccaaa    3300
agaaatcctc ctagaaatag caaaaagatc tagtggagat ctaagagcag ctataaatga    3360
tctacagacc gttgtagtgg gtggttacga agatgctacg caagtttt gg catatagaga    3420 tgtagaaaag acagtctttc aagccctagg actcgtcttt ggaagtgaca acgccaagag    3480
ggcaaagatg gcaatgtgga acttggacat gtcccctgat gaattcctgc tatgggtaga    3540
tgagaacatt cctcacctct acctaaatcc agaggagatt gcccaggcgt atgatgcaat    3600
tagtagagcc gacatatacc tcggaagggc cgccagaact ggaaactatt cactctggaa    3660
gtacgcaata gatatgatga ctgcaggagt tgccgtggca gggagaaaga aaggggatt    3720
```

```
tgtcaagttt tatcctccca acaccctaaa gattttagcg gaaagcaaag aagaaagaga    3780
gatcagagag tccataatta aaagataat acgagagatg cncatgagta ggctacaggc    3840
aatagaaacg atgaaaataa ttagagagat tttcgagaac aatctagacc ttgctgcgca    3900
ctttacagtg ttccttggtc tgtctgaaaa agaagttgag tttctagctg gaaaggaaaa    3960
agctggtacc atttggggca aagccttagc attaagaagg aaacttaagg agcttggaat    4020
aagagaggag gagaagccta agttgaaat tgaagaagag gaagaagagg aagaaaagac    4080
cgaagaagaa aaagaggaaa tagaagaaaa acccgaagaa gagaaagaag aggaagaa      4140 agaaaaggaa aagccaaaga aaggcaaaca agcaactctc tttgactttc ttaaaaagtg    4200
attacccttt ttcttctatt agagctccga ataaagttgg ccctctaatt ttttctattg    4260
tctcctccac attaatcttt acgaattgga attcctgcag cccgggggat ccactagtcc    4320
tagagcggcc gccaccgcgg tggagctcca gcttttgttc cctttagtga gggttaattt    4380
cgagcttggc gtaatcatgg tcatagctgt ttcctgtgtg aaattgttat ccgctcacaa    4440
ttccacacaa catacgaacc cggaagcata aattgtaaac ccnggggtgc ctaatgantg    4500
anctaactca cattaattgc nttgcgctca ctgcccgctt tccantcggg aaacctgtcg    4560
tgccagctgc attaatgaat cggccaacnc gcggggaaaa gcggttgcgt attgggcgct    4620
cttccgcttc ctcgctcatg actcgctgcg ctcggtcntc ggctgcggcg aacggtatca    4680
gctcatcaaa ggcggtaata cggttatccn caaatcaggg gataacgcag gaaaaaactt    4740
tnnacaaaag gcnncaaaag gcggaaacta aaaggcgcnt tctgggtttt tcntaggccc    4800 ncccccganaa ctcnaaaaat caacncattc aagtgggaaa ccaaagaa              4848
```

<210> SEQ ID NO 62
<211> LENGTH: 1603
<212> TYPE: PRT
<213> ORGANISM: Artificial Sequence
<220> FEATURE:
<223> OTHER INFORMATION: Description of Artificial Sequence: Amino acid
  sequence of the genomic RFC clone
<220> FEATURE:
<221> NAME/KEY: MISC_FEATURE
<222> LOCATION: (7)
<223> OTHER INFORMATION: Xaa is any amino acid
<220> FEATURE:
<221> NAME/KEY: MISC_FEATURE
<222> LOCATION: (14)
<223> OTHER INFORMATION: Xaa is any amino acid
<220> FEATURE:
<221> NAME/KEY: MISC_FEATURE
<222> LOCATION: (35)
<223> OTHER INFORMATION: Xaa is any amino acid
<220> FEATURE:
<221> NAME/KEY: MISC_FEATURE
<222> LOCATION: (45)
<223> OTHER INFORMATION: Xaa is any amino acid
<220> FEATURE:
<221> NAME/KEY: MISC_FEATURE
<222> LOCATION: (1269)
<223> OTHER INFORMATION: Xaa is any amino acid
<220> FEATURE:
<221> NAME/KEY: MISC_FEATURE
<222> LOCATION: (1490)..(1491)
<223> OTHER INFORMATION: Xaa is any amino acid
<220> FEATURE:
<221> NAME/KEY: MISC_FEATURE
<222> LOCATION: (1496)
<223> OTHER INFORMATION: Xaa is any amino acid
<220> FEATURE:
<221> NAME/KEY: MISC_FEATURE
<222> LOCATION: (1504)
<223> OTHER INFORMATION: Xaa is any amino acid

```
<220> FEATURE:
<221> NAME/KEY: MISC_FEATURE
<222> LOCATION: (1519)
<223> OTHER INFORMATION: Xaa is any amino acid
<220> FEATURE:
<221> NAME/KEY: MISC_FEATURE
<222> LOCATION: (1522)
<223> OTHER INFORMATION: Xaa is any amino acid
<220> FEATURE:
<221> NAME/KEY: MISC_FEATURE
<222> LOCATION: (1542)
<223> OTHER INFORMATION: Xaa is any amino acid
<220> FEATURE:
<221> NAME/KEY: MISC_FEATURE
<222> LOCATION: (1559)
<223> OTHER INFORMATION: Xaa is any amino acid
<220> FEATURE:
<221> NAME/KEY: MISC_FEATURE
<222> LOCATION: (1570)
<223> OTHER INFORMATION: Xaa is any amino acid
<220> FEATURE:
<221> NAME/KEY: MISC_FEATURE
<222> LOCATION: (1574)
<223> OTHER INFORMATION: Xaa is any amino acid
<220> FEATURE:
<221> NAME/KEY: MISC_FEATURE
<222> LOCATION: (1581)
<223> OTHER INFORMATION: Xaa is any amino acid
<220> FEATURE:
<221> NAME/KEY: MISC_FEATURE
<222> LOCATION: (1586)
<223> OTHER INFORMATION: Xaa is any amino acid
<220> FEATURE:
<221> NAME/KEY: MISC_FEATURE
<222> LOCATION: (1591)
<223> OTHER INFORMATION: Xaa is any amino acid
<220> FEATURE:
<221> NAME/KEY: MISC_FEATURE
<222> LOCATION: (1593)
<223> OTHER INFORMATION: Xaa is any amino acid

<400> SEQUENCE: 62

Pro Lys Ile Val Ile Gln Xaa Asn Gly Glu Asp Gly Val Xaa Leu Glu
  1               5                  10                  15

Gly Ala Tyr Pro Glu Lys Cys Ser Arg Ser Tyr Ser Gln Leu Ser Ala
                 20                  25                  30

Asp Leu Xaa Phe Phe Leu Leu Phe Phe Cys Ser Val Xaa Ala Asp Lys
             35                  40                  45

Leu Asn Asn Thr Leu Ile Pro Phe Leu Val Val Cys Glu Ser Met Ser
 50                  55                  60

Glu Glu Ile Arg Glu Val Lys Val Leu Glu Lys Pro Trp Val Glu Lys
 65                  70                  75                  80

Tyr Arg Pro Gln Arg Leu Asp Asp Ile Val Gly Gln Glu His Ile Val
                 85                  90                  95

Lys Arg Leu Lys His Tyr Val Lys Thr Gly Ser Met Pro His Leu Leu
            100                 105                 110

Phe Ala Gly Pro Pro Gly Val Gly Lys Cys Leu Thr Gly Asp Thr Lys
            115                 120                 125

Val Ile Ala Asn Gly Gln Leu Phe Glu Leu Gly Glu Leu Val Glu Lys
130                 135                 140

Leu Ser Gly Gly Arg Phe Gly Pro Thr Pro Val Lys Gly Leu Lys Val
145                 150                 155                 160

Leu Gly Ile Asp Glu Asp Gly Lys Leu Arg Glu Phe Glu Val Gln Tyr
                165                 170                 175

Val Tyr Lys Asp Arg Thr Asp Arg Leu Ile Lys Ile Lys Thr Gln Leu
            180                 185                 190
```

-continued

```
Gly Arg Glu Leu Lys Val Thr Pro Tyr His Pro Leu Leu Val Ile Gly
        195                 200                 205
Glu Asn Gly Glu Leu Lys Trp Ile Lys Ala Glu Glu Leu Lys Leu Gly
    210                 215                 220
Asp Lys Leu Ala Ile Pro Ser Phe Leu Pro Leu Ile Thr Gly Glu Asn
225                 230                 235                 240
Pro Leu Ala Glu Trp Leu Gly Tyr Phe Met Gly Ser Gly Tyr Ala Tyr
                245                 250                 255
Pro Lys Asn Ser Val Ile Thr Phe Thr Asn Glu Asp Pro Leu Ile Arg
            260                 265                 270
Gln Arg Phe Met Glu Leu Thr Glu Lys Leu Phe Pro Asp Ala Lys Ile
        275                 280                 285
Arg Glu Arg Ile His Ala Asp Gly Thr Pro Glu Val Tyr Val Val Ser
    290                 295                 300
Arg Lys Ala Trp Ser Leu Val Asn Ser Ile Ser Leu Thr Leu Ile Pro
305                 310                 315                 320
Arg Glu Gly Trp Lys Gly Ile Arg Ser Phe Leu Arg Ala Tyr Ser Asp
                325                 330                 335
Cys Asn Gly Arg Ile Glu Ser Asp Ala Ile Val Leu Ser Thr Asp Asn
            340                 345                 350
Asn Asp Met Ala Gln Gln Ile Ala Tyr Ala Leu Ala Ser Phe Gly Ile
        355                 360                 365
Ile Ala Lys Met Asp Gly Glu Asp Val Ile Ile Ser Gly Ser Asp Asn
    370                 375                 380
Ile Glu Arg Phe Leu Asn Glu Ile Gly Phe Ser Thr Gln Ser Lys Leu
385                 390                 395                 400
Lys Glu Ala Gln Lys Leu Ile Arg Lys Thr Asn Val Arg Ser Asp Gly
                405                 410                 415
Leu Lys Ile Asn Tyr Glu Leu Ile Ser Tyr Val Lys Asp Arg Leu Arg
            420                 425                 430
Leu Asn Val Asn Asp Lys Arg Asn Leu Ser Tyr Arg Asn Ala Lys Glu
        435                 440                 445
Leu Ser Trp Glu Leu Met Lys Glu Ile Tyr Tyr Arg Leu Glu Glu Leu
    450                 455                 460
Glu Arg Leu Lys Lys Val Leu Ser Glu Pro Ile Leu Ile Asp Trp Asn
465                 470                 475                 480
Glu Val Ala Lys Lys Ser Asp Glu Val Ile Glu Lys Ala Lys Ile Arg
                485                 490                 495
Ala Glu Lys Leu Leu Glu Tyr Ile Lys Gly Glu Arg Lys Pro Ser Phe
            500                 505                 510
Lys Glu Tyr Ile Glu Ile Ala Lys Val Leu Gly Ile Asn Val Glu Arg
        515                 520                 525
Thr Ile Glu Ala Met Lys Ile Phe Ala Lys Arg Tyr Ser Ser Tyr Ala
    530                 535                 540
Glu Ile Gly Arg Lys Leu Gly Thr Trp Asn Phe Asn Val Lys Thr Ile
545                 550                 555                 560
Leu Glu Ser Asp Thr Val Asp Asn Val Glu Ile Leu Glu Lys Ile Arg
                565                 570                 575
Lys Ile Glu Leu Glu Leu Ile Glu Ile Leu Ser Asp Gly Lys Leu
            580                 585                 590
Lys Glu Gly Ile Ala Tyr Leu Ile Phe Leu Phe Gln Asn Glu Leu Tyr
        595                 600                 605
```

```
Trp Asp Glu Ile Thr Glu Val Lys Glu Leu Arg Gly Asp Phe Ile Ile
610                 615                 620
Tyr Asp Leu His Val Pro Gly Tyr His Asn Phe Ile Ala Gly Asn Met
625                 630                 635                 640
Pro Thr Val Val His Asn Thr Thr Ala Ala Leu Ala Leu Ala Arg Glu
                645                 650                 655
Leu Phe Gly Glu Asn Trp Arg His Asn Phe Leu Glu Leu Asn Ala Ser
            660                 665                 670
Asp Glu Arg Gly Ile Asn Val Ile Arg Glu Lys Val Lys Glu Phe Ala
        675                 680                 685
Arg Thr Lys Pro Ile Gly Gly Ala Ser Phe Lys Ile Ile Phe Leu Asp
690                 695                 700
Glu Ala Asp Ala Leu Thr Gln Asp Ala Gln Gln Ala Leu Arg Arg Thr
705                 710                 715                 720
Met Glu Met Phe Ser Ser Asn Val Arg Phe Ile Leu Ser Cys Asn Tyr
                725                 730                 735
Ser Ser Lys Ile Ile Glu Pro Ile Gln Ser Arg Cys Ala Ile Phe Arg
            740                 745                 750
Phe Arg Pro Leu Arg Asp Glu Asp Ile Ala Lys Arg Leu Arg Tyr Ile
        755                 760                 765
Ala Glu Asn Glu Gly Leu Glu Leu Thr Glu Glu Gly Leu Gln Ala Ile
770                 775                 780
Leu Tyr Ile Ala Glu Gly Asp Met Arg Arg Ala Ile Asn Ile Leu Gln
785                 790                 795                 800
Ala Ala Ala Ala Leu Asp Lys Lys Ile Thr Asp Glu Asn Val Phe Met
                805                 810                 815
Val Ala Ser Arg Ala Arg Pro Glu Asp Ile Arg Glu Met Met Leu Leu
            820                 825                 830
Ala Leu Lys Gly Asn Phe Leu Lys Ala Arg Glu Lys Leu Arg Glu Ile
        835                 840                 845
Leu Leu Lys Gln Gly Leu Ser Gly Glu Asp Val Leu Val Gln Met His
850                 855                 860
Lys Glu Val Phe Asn Leu Pro Ile Glu Glu Pro Lys Lys Val Leu Leu
865                 870                 875                 880
Ala Asp Lys Ile Gly Glu Tyr Asn Phe Arg Leu Val Glu Gly Ala Asn
                885                 890                 895
Glu Ile Ile Gln Leu Glu Ala Leu Leu Ala Gln Phe Thr Leu Ile Gly
            900                 905                 910
Lys Lys Ser Met Pro Glu Leu Pro Trp Val Glu Lys Tyr Arg Pro Lys
        915                 920                 925
Lys Leu Ser Glu Ile Val Asn Gln Glu Glu Ala Ile Glu Lys Val Arg
930                 935                 940
Ala Trp Ile Glu Ser Trp Leu His Gly His Pro Pro Lys Lys Ala
945                 950                 955                 960
Leu Leu Leu Ala Gly Pro Pro Gly Ser Gly Lys Thr Thr Thr Val Tyr
                965                 970                 975
Ala Leu Ala Asn Glu Tyr Asn Phe Glu Val Ile Glu Leu Asn Ala Ser
            980                 985                 990
Asp Glu Arg Thr Tyr Glu Lys Ile Ser Arg Tyr Val Gln Ala Ala Tyr
        995                 1000                1005
Thr Met Asp Ile Leu Gly Lys Arg Arg Lys Ile Ile Phe Leu Asp Glu
    1010                1015                1020
```

```
Ala Asp Asn Ile Glu Pro Ser Gly Ala Lys Glu Ile Ala Lys Leu Ile
1025                1030                1035                1040

Asp Lys Ala Lys Asn Pro Ile Ile Met Ala Ala Asn Lys Tyr Trp Glu
            1045                1050                1055

Val Pro Lys Glu Ile Arg Glu Lys Ala Glu Leu Val Glu Tyr Lys Arg
        1060                1065                1070

Leu Thr Gln Arg Asp Val Met Asn Ala Leu Ile Arg Ile Leu Lys Arg
    1075                1080                1085

Glu Gly Ile Thr Val Pro Lys Glu Ile Leu Leu Glu Ile Ala Lys Arg
1090                1095                1100

Ser Ser Gly Asp Leu Arg Ala Ala Ile Asn Asp Leu Gln Thr Val Val
1105                1110                1115                1120

Val Gly Gly Tyr Glu Asp Ala Thr Gln Val Leu Ala Tyr Arg Asp Val
            1125                1130                1135

Glu Lys Thr Val Phe Gln Ala Leu Gly Leu Val Phe Gly Ser Asp Asn
        1140                1145                1150

Ala Lys Arg Ala Lys Met Ala Met Trp Asn Leu Asp Met Ser Pro Asp
    1155                1160                1165

Glu Phe Leu Leu Trp Val Asp Glu Asn Ile Pro His Leu Tyr Leu Asn
1170                1175                1180

Pro Glu Glu Ile Ala Gln Ala Tyr Asp Ala Ile Ser Arg Ala Asp Ile
1185                1190                1195                1200

Tyr Leu Gly Arg Ala Ala Arg Thr Gly Asn Tyr Ser Leu Trp Lys Tyr
            1205                1210                1215

Ala Ile Asp Met Met Thr Ala Gly Val Ala Val Ala Gly Arg Lys Arg
        1220                1225                1230

Arg Gly Phe Val Lys Phe Tyr Pro Pro Asn Thr Leu Lys Ile Leu Ala
    1235                1240                1245

Glu Ser Lys Glu Glu Arg Glu Ile Arg Glu Ser Ile Ile Lys Lys Ile
1250                1255                1260

Ile Arg Glu Met Xaa Met Ser Arg Leu Gln Ala Ile Glu Thr Met Lys
1265                1270                1275                1280

Ile Ile Arg Glu Ile Phe Glu Asn Asn Leu Asp Leu Ala Ala His Phe
            1285                1290                1295

Thr Val Phe Leu Gly Leu Ser Glu Lys Glu Val Glu Phe Leu Ala Gly
        1300                1305                1310

Lys Glu Lys Ala Gly Thr Ile Trp Gly Lys Ala Leu Ala Leu Arg Arg
    1315                1320                1325

Lys Leu Lys Glu Leu Gly Ile Arg Glu Glu Glu Lys Pro Lys Val Glu
1330                1335                1340

Ile Glu Glu Glu Glu Glu Glu Glu Lys Thr Glu Glu Lys Glu
1345                1350                1355                1360

Glu Ile Glu Glu Lys Pro Glu Glu Lys Glu Glu Lys Lys Glu
            1365                1370                1375

Lys Glu Lys Pro Lys Lys Gly Lys Gln Ala Thr Leu Phe Asp Phe Leu
        1380                1385                1390

Lys Lys Leu Pro Phe Phe Tyr Ser Ser Glu Ser Trp Pro Ser Asn
    1395                1400                1405

Phe Phe Tyr Cys Leu Leu His Ile Asn Leu Tyr Glu Leu Glu Phe Leu
1410                1415                1420

Gln Pro Gly Gly Ser Thr Ser Ser Arg Ala Ala Ala Thr Ala Val Glu
1425                1430                1435                1440
```

-continued

```
Leu Gln Leu Leu Phe Pro Leu Val Arg Val Asn Phe Glu Leu Gly Val
            1445                1450                1455

Ile Met Val Ile Ala Val Ser Cys Val Lys Leu Leu Ser Ala His Asn
        1460                1465                1470

Ser Thr Gln His Thr Asn Pro Glu Ala Ile Val Asn Pro Gly Val Pro
    1475                1480                1485

Asn Xaa Xaa Asn Ser His Leu Xaa Cys Ala His Cys Pro Leu Ser Xaa
    1490                1495                1500

Arg Glu Thr Cys Arg Ala Ser Cys Ile Asn Glu Ser Ala Asn Xaa Arg
1505                1510                1515                1520

Gly Xaa Ala Val Ala Tyr Trp Ala Leu Phe Arg Phe Leu Ala His Asp
        1525                1530                1535

Ser Leu Arg Ser Val Xaa Gly Cys Gly Glu Arg Tyr Gln Leu Ile Lys
        1540                1545                1550

Gly Gly Asn Thr Val Ile Xaa Lys Ser Gly Asp Asn Ala Gly Lys Asn
        1555                1560                1565

Phe Xaa Gln Lys Ala Xaa Lys Gly Gly Asn Lys Ala Xaa Ser Gly Phe
    1570                1575                1580

Phe Xaa Gly Pro Pro Arg Xaa Leu Xaa Lys Ser Thr His Ser Ser Gly
1585                1590                1595                1600

Lys Pro Lys

<210> SEQ ID NO 63
<211> LENGTH: 479
<212> TYPE: PRT
<213> ORGANISM: Artificial Sequence
<220> FEATURE:
<223> OTHER INFORMATION: Description of Artificial Sequence: Recombinant
      P55 clone
<220> FEATURE:
<221> NAME/KEY: MISC_FEATURE
<222> LOCATION: (354)
<223> OTHER INFORMATION: Xaa is any amino acid

<400> SEQUENCE: 63

Met Pro Glu Leu Pro Trp Val Glu Lys Tyr Arg Pro Lys Lys Leu Ser
1               5                   10                  15

Glu Ile Val Asn Gln Glu Ala Ile Glu Lys Val Arg Ala Trp Ile
            20                  25                  30

Glu Ser Trp Leu His Gly His Pro Pro Lys Lys Ala Leu Leu Leu
        35                  40                  45

Ala Gly Pro Pro Gly Ser Gly Lys Thr Thr Thr Val Tyr Ala Leu Ala
    50                  55                  60

Asn Glu Tyr Asn Phe Glu Val Ile Glu Leu Asn Ala Ser Asp Glu Arg
65                  70                  75                  80

Thr Tyr Glu Lys Ile Ser Arg Tyr Val Gln Ala Ala Tyr Thr Met Asp
                85                  90                  95

Ile Leu Gly Lys Arg Arg Lys Ile Ile Phe Leu Asp Glu Ala Asp Asn
            100                 105                 110

Ile Glu Pro Ser Gly Ala Lys Glu Ile Ala Lys Leu Ile Asp Lys Ala
        115                 120                 125

Lys Asn Pro Ile Ile Met Ala Ala Asn Lys Tyr Trp Glu Val Pro Lys
    130                 135                 140

Glu Ile Arg Glu Lys Ala Glu Leu Val Glu Tyr Lys Arg Leu Thr Gln
145                 150                 155                 160

Arg Asp Val Met Asn Ala Leu Ile Arg Ile Leu Lys Arg Glu Gly Ile
                165                 170                 175
```

```
Thr Val Pro Lys Glu Ile Leu Leu Glu Ile Ala Lys Arg Ser Ser Gly
            180                 185                 190

Asp Leu Arg Ala Ala Ile Asn Asp Leu Gln Thr Val Val Gly Gly
        195                 200                 205

Tyr Glu Asp Ala Thr Gln Val Leu Ala Tyr Arg Asp Val Glu Lys Thr
    210                 215                 220

Val Phe Gln Ala Leu Gly Leu Val Phe Gly Ser Asp Asn Ala Lys Arg
225                 230                 235                 240

Ala Lys Met Ala Met Trp Asn Leu Asp Met Ser Pro Asp Glu Phe Leu
                245                 250                 255

Leu Trp Val Asp Glu Asn Ile Pro His Leu Tyr Leu Asn Pro Glu Glu
            260                 265                 270

Ile Ala Gln Ala Tyr Asp Ala Ile Ser Arg Ala Asp Ile Tyr Leu Gly
        275                 280                 285

Arg Ala Ala Arg Thr Gly Asn Tyr Ser Leu Trp Lys Tyr Ala Ile Asp
    290                 295                 300

Met Met Thr Ala Gly Val Ala Val Gly Arg Lys Arg Gly Phe
305                 310                 315                 320

Val Lys Phe Tyr Pro Pro Asn Thr Leu Lys Ile Leu Ala Glu Ser Lys
                325                 330                 335

Glu Glu Arg Glu Ile Arg Glu Ser Ile Ile Lys Lys Ile Ile Arg Glu
            340                 345                 350

Met Xaa Met Ser Arg Leu Gln Ala Ile Glu Thr Met Lys Ile Ile Arg
        355                 360                 365

Glu Ile Phe Glu Asn Asn Leu Asp Leu Ala Ala His Phe Thr Val Phe
    370                 375                 380

Leu Gly Leu Ser Glu Lys Glu Val Glu Phe Leu Ala Gly Lys Glu Lys
385                 390                 395                 400

Ala Gly Thr Ile Trp Gly Lys Ala Leu Ala Leu Arg Arg Lys Leu Lys
                405                 410                 415

Glu Leu Gly Ile Arg Glu Glu Lys Pro Lys Val Glu Ile Glu Glu
            420                 425                 430

Glu Glu Glu Glu Glu Lys Thr Glu Glu Glu Lys Glu Ile Glu
        435                 440                 445

Glu Lys Pro Glu Glu Lys Glu Glu Lys Lys Glu Lys Glu Lys
    450                 455                 460

Pro Lys Lys Gly Lys Gln Ala Thr Leu Phe Asp Phe Leu Lys Lys
465                 470                 475

<210> SEQ ID NO 64
<211> LENGTH: 327
<212> TYPE: PRT
<213> ORGANISM: Artificial Sequence
<220> FEATURE:
<223> OTHER INFORMATION: Description of Artificial Sequence: Recombinant
      P38 clone

<400> SEQUENCE: 64

Met Ser Glu Glu Ile Arg Glu Val Lys Val Leu Glu Lys Pro Trp Val
1               5                   10                  15

Glu Lys Tyr Arg Pro Gln Arg Leu Asp Asp Ile Val Gly Gln Glu His
                20                  25                  30

Ile Val Lys Arg Leu Lys His Tyr Val Lys Thr Gly Ser Met Pro His
            35                  40                  45

Leu Leu Phe Ala Gly Pro Pro Gly Val Gly Lys Thr Thr Ala Ala Leu
        50                  55                  60
```

-continued

Ala Leu Ala Arg Glu Leu Phe Gly Glu Asn Trp Arg His Asn Phe Leu
 65                  70                  75                  80

Glu Leu Asn Ala Ser Asp Glu Arg Gly Ile Asn Val Ile Arg Glu Lys
                 85                  90                  95

Val Lys Glu Phe Ala Arg Thr Lys Pro Ile Gly Gly Ala Ser Phe Lys
            100                 105                 110

Ile Ile Phe Leu Asp Glu Ala Asp Ala Leu Thr Gln Asp Ala Gln Gln
        115                 120                 125

Ala Leu Arg Arg Thr Met Glu Met Phe Ser Ser Asn Val Arg Phe Ile
    130                 135                 140

Leu Ser Cys Asn Tyr Ser Ser Lys Ile Ile Glu Pro Ile Gln Ser Arg
145                 150                 155                 160

Cys Ala Ile Phe Arg Phe Arg Pro Leu Arg Asp Glu Asp Ile Ala Lys
                165                 170                 175

Arg Leu Arg Tyr Ile Ala Glu Asn Glu Gly Leu Glu Leu Thr Glu Glu
            180                 185                 190

Gly Leu Gln Ala Ile Leu Tyr Ile Ala Glu Gly Asp Met Arg Arg Ala
        195                 200                 205

Ile Asn Ile Leu Gln Ala Ala Ala Leu Asp Lys Lys Ile Thr Asp
    210                 215                 220

Glu Asn Val Phe Met Val Ala Ser Arg Ala Arg Pro Glu Asp Ile Arg
225                 230                 235                 240

Glu Met Met Leu Leu Ala Leu Lys Gly Asn Phe Leu Lys Ala Arg Glu
                245                 250                 255

Lys Leu Arg Glu Ile Leu Leu Lys Gln Gly Leu Ser Gly Glu Asp Val
            260                 265                 270

Leu Val Gln Met His Lys Glu Val Phe Asn Leu Pro Ile Glu Pro
        275                 280                 285

Lys Lys Val Leu Leu Ala Asp Lys Ile Gly Glu Tyr Asn Phe Arg Leu
    290                 295                 300

Val Glu Gly Ala Asn Glu Ile Ile Gln Leu Glu Ala Leu Leu Ala Gln
305                 310                 315                 320

Phe Thr Leu Ile Gly Lys Lys
                325

<210> SEQ ID NO 65
<211> LENGTH: 1077
<212> TYPE: DNA
<213> ORGANISM: Artificial Sequence
<220> FEATURE:
<223> OTHER INFORMATION: Description of Artificial Sequence: RFA clone

<400> SEQUENCE: 65
atgagtgcat ttacaaaaga agaaataatc aagaggatcc tggaagaagt ggaaggaata      60
actctagaag aaattgagaa ccaaataagg caaataatga gggaaaacaa tatttcagag     120
catgcagctg ctctcttact agcagaaagg ctggagttga agttaccaa agagaagaa       180 caacctttaa tgaagattag cgacctatat ccaggaatgg atccccacga ggtcaacatt     240
gttggaagaa tacttaagaa gtatccaccg cgagaataca caagaagga tggaagcatt      300 ggaagggttg ccagtctagt tatatacgat gatactggga gagcgagggt tgttctttgg     360
gattcaaaag ttttggagta ttacagcaag ctagaagtag gggatgttat taaggtttta     420
gacgcccagg ttagggagag cttatctggt ttgcctgaat tgcacattaa cttcagggct     480
agaataatta aaaacccaga tgatcctagg gttcaggata tcccacctct tgaagaagtt     540

-continued

```
agagtggcaa cttatacgag aaagaagatc agtgaggtcg agcctgggga tagatttgta    600
gagcttaggg gaacaattgc caaagtttac agagttttgg tatatgatgc atgtccagag    660
tgtaagaaga aggttgacta tgacccagga atggacgttt ggatatgtcc agaacatgga    720
gaggttgagc caataaaaat cactattctt gactttgggc ttgatgatgg ctcgggatac    780
attaggatta ccctctttgg agacgatgct gaagagttgc tgggagtagg gccagaagag    840
attgcccaaa agcttaagga atggagagc atgggcatga ctctcaagga ggcagcgaga    900
aaattggcgg aggaagagtt ctacaatata atagggaaag aaataatcgt gaggggaaat    960
gtaattgagg acaggttctt gggcctaatc ttaagggcct cctcctggga agaagttgac   1020
tacaagagag aaattgagag aattaagagg gaattggaag aattgggggt gatgtga      1077
```

<210> SEQ ID NO 66
<211> LENGTH: 360
<212> TYPE: PRT
<213> ORGANISM: Artificial Sequence
<220> FEATURE:
<223> OTHER INFORMATION: Description of Artificial Sequence: Amino acid
      sequence of RFA clone

<400> SEQUENCE: 66

```
Met Ile Met Ser Ala Phe Thr Lys Glu Glu Ile Ile Lys Arg Ile Leu
  1               5                  10                  15

Glu Glu Val Glu Gly Ile Thr Leu Glu Glu Ile Glu Asn Gln Ile Arg
             20                  25                  30

Gln Ile Met Arg Glu Asn Asn Ile Ser Glu His Ala Ala Ala Leu Leu
         35                  40                  45

Leu Ala Glu Arg Leu Gly Val Glu Val Thr Lys Arg Glu Glu Gln Pro
     50                  55                  60

Leu Met Lys Ile Ser Asp Leu Tyr Pro Gly Met Asp Pro His Glu Val
 65                  70                  75                  80

Asn Ile Val Gly Arg Ile Leu Lys Lys Tyr Pro Pro Arg Glu Tyr Thr
                 85                  90                  95

Lys Lys Asp Gly Ser Ile Gly Arg Val Ala Ser Leu Val Ile Tyr Asp
            100                 105                 110

Asp Thr Gly Arg Ala Arg Val Val Leu Trp Asp Ser Lys Val Leu Glu
        115                 120                 125

Tyr Tyr Ser Lys Leu Glu Val Gly Asp Val Ile Lys Val Leu Asp Ala
    130                 135                 140

Gln Val Arg Glu Ser Leu Ser Gly Leu Pro Glu Leu His Ile Asn Phe
145                 150                 155                 160

Arg Ala Arg Ile Ile Lys Asn Pro Asp Asp Pro Arg Val Gln Asp Ile
                165                 170                 175

Pro Pro Leu Glu Glu Val Arg Val Ala Thr Tyr Thr Arg Lys Lys Ile
            180                 185                 190

Ser Glu Val Glu Pro Gly Asp Arg Phe Val Glu Leu Arg Gly Thr Ile
        195                 200                 205

Ala Lys Val Tyr Arg Val Leu Val Tyr Asp Ala Cys Pro Glu Cys Lys
    210                 215                 220

Lys Lys Val Asp Tyr Asp Pro Gly Met Asp Val Trp Ile Cys Pro Glu
225                 230                 235                 240

His Gly Glu Val Glu Pro Ile Lys Ile Thr Ile Leu Asp Phe Gly Leu
                245                 250                 255

Asp Asp Gly Ser Gly Tyr Ile Arg Ile Thr Leu Phe Gly Asp Asp Ala
            260                 265                 270
```

```
Glu Glu Leu Leu Gly Val Gly Pro Glu Glu Ile Ala Gln Lys Leu Lys
            275                 280                 285

Glu Met Glu Ser Met Gly Met Thr Leu Lys Glu Ala Ala Arg Lys Leu
            290                 295                 300

Ala Glu Glu Glu Phe Tyr Asn Ile Ile Gly Lys Glu Ile Ile Val Arg
305                 310                 315                 320

Gly Asn Val Ile Glu Asp Arg Phe Leu Gly Leu Ile Leu Arg Ala Ser
                    325                 330                 335

Ser Trp Glu Glu Val Asp Tyr Lys Arg Glu Ile Glu Arg Ile Lys Arg
                340                 345                 350

Glu Leu Glu Glu Leu Gly Val Met
            355                 360

<210> SEQ ID NO 67
<211> LENGTH: 2604
<212> TYPE: DNA
<213> ORGANISM: Artificial Sequence
<220> FEATURE:
<223> OTHER INFORMATION: Description of Artificial Sequence: Recombinant
      helicase 2

<400> SEQUENCE: 67
```

| | | | | | |
|---|---|---|---|---|---|
| atgattgagg | agctgttcaa | gggattagag | agtgaaatcg | ttggacttca | cgagattccc | 60 |
| ccaaagaggg | gagagtatgg | ggagttcaaa | ttcaggaatg | aagaagttaa | tgagttagtt | 120 |
| aagaggctcg | gatttagact | ttattctcac | caagttaaag | ccctagaaaa | gctgtattca | 180 |
| gggaaaaacg | tagttgtttc | aacgcccaca | gctagtggga | aaagcgagat | atttaggttg | 240 |
| tttatctttg | acgaaatact | gtcaagcccg | tcctcaactt | ttctcttaat | ctacccaaca | 300 |
| agagcccttaa | taaacaacca | aatggaaaaa | ttcgaaaaga | aaacactat | ctttgaggag | 360 |
| atttgtggaa | aaagagttcg | agcagaagtc | ttaactggag | atacggaatg | ggaaaagaga | 420 |
| agagaaatca | ttaggagcaa | accaaacgta | atcttcacga | cacccgatat | gcttcatcat | 480 |
| cacattcttc | ccaggtggag | ggattatttc | tggcttttaa | aggggcttag | acttcttgtc | 540 |
| gtggacgaat | gcacgtttta | taggggatc | tttggaacaa | atgttgctta | tgttttcaag | 600 |
| agactctttc | tcaggcttaa | gagattaagt | tcaagccccc | aaatactggc | cctttcagca | 660 |
| actttgagaa | accccaaaga | atttgctgaa | caatttttg | agactgaatt | tgaggaggtc | 720 |
| aaggaagctg | gaagtccaag | cccgagaaga | attatagtca | tgtttgagcc | aagaaggttt | 780 |
| actggagaac | aactaatcaa | gcaaattgtt | gagagactaa | ctagaaagaa | cataaagacc | 840 |
| ttggtatttt | ttgactccag | aaaggggaca | gaaagaatca | tgaggctttt | cctgttctca | 900 |
| gatgcttttg | ataggatcac | aacatacaaa | gggacgctaa | ctaagaggga | aggtttcta | 960 |
| atagagagag | actttaggga | gggcaacctc | acagttctcc | taacgacaaa | tgcactcgag | 1020 |
| ttgggaattg | acattggaga | tttagatgca | gtaataaact | atgggattcc | ttcagatgga | 1080 |
| ttgttttcac | taattcaaag | atttggtagg | gccggaaggg | atccaaatag | aattgcaata | 1140 |
| aacgggataa | ttttgagaag | aaatggattg | gactactatt | acaaagaaca | tttcgatgag | 1200 |
| ctcgttgagg | gaatagaaaa | gggcctagtg | agaaaatcc | ccgttaactt | ggacaatgaa | 1260 |
| aagatagcga | aaaagcacct | ccactatgcc | atagctgaac | ttggagttgt | ctcaattaaa | 1320 |
| gaaattgagg | ggagatggaa | gagattcata | aagaccctcg | tagaggaggg | atacgtggaa | 1380 |
| gttacaagaa | atccaataac | tggagaggaa | gaaataagac | tcagaagacc | tcctgtctat | 1440 |
| tcttcaatta | gaacggcgag | cgatgaaagc | tacttcttag | tcgtggatga | accctggata | 1500 |

```
agggggagctt tgcagaggaa gaggggagcc gaacttctcc gttttgtaaa ctacctcaaa   1560
gttagaggaa tggtagttga ggaagttgat gagatagaat tccacagaag tctactccct   1620
ggaatggtct acctttcaag gggaaggccc tacatggcag ttgataagat aaagattgag   1680
aagttccact tcgtttttgc gaggcctctt ccaatcgaag aagaaataga tactagttca   1740
agtaaaattg aaaacattga gatacttgag gttaaagacg agaaaactgt tgggcccaata  1800 aaagtgaagt tcggaagact tagagtaagg cacgaataca ctggatacgc cgtgagggga   1860
agagacgttg aaaggcacgt taagagatta aagagctaa aagatgaggg gatactaagg    1920
ggagagattg acatcgtccc atacatttgg gaatcctgga gtttgcgag ggtactcttt    1980 gacacccct acattagaga gtttgaaact gaaggtttct ggcttgagtt tccaaacgat    2040
attaggatag ttcccgaaga gggagtttagg gaattctttg cagtggcctc tgagatagat   2100
ccagagctcg cgatgttcct ctacaacaga attagtagaa aatctctatt ccccacgctt    2160
ctgggagcaa ccacacacta cataaggagt ttcatccttc accacgccaa agataaggga   2220
gaagaattcg catttgccgt aaaaaagatg atcgacagca aggatgggat aggctcaggg    2280
cttcatgcaa ttgagcccaa tataataaag cttgctccag ttgtgactca tgtggattcg   2340
agagaaatag gcggctacag ctacgatgac ttccatgaaa agccagtgat cttcatctat   2400
gatgggaata aggcggaag cggaataatt aggcaggtgt atgagaacgt agaaaagctg    2460
atgtacagga gtttggagca tataaagaag tgtccatgca agacggctg tcctgcctgc    2520 atatattctc ccaagtgcgg aactttcaat gaattcctcg acaagtggat ggcaataaga    2580
atatgggaaa aagtccttcc ttaa                                           2604

<210> SEQ ID NO 68
<211> LENGTH: 2511
<212> TYPE: DNA
<213> ORGANISM: Artificial Sequence
<220> FEATURE:
<223> OTHER INFORMATION: Description of Artificial Sequence: Recombinant
      helicase 3

<400> SEQUENCE: 68
atgttaatag ttgtaagacc aggaagaaaa aagaatgagc tcgaggcttt tataattgaa    60
aaccctccag aaaagctctc tcaaagaaga aatttaaaag ctgataggt agttaggctc    120 ataatgagag ataatagact ttttaaagct cttgaaggaa gtcagtattt aaatccaaag    180
gaagtggaga gagcccttag aaattcaagg atagttctgg tgaatgccaa cgagtgggaa    240
gagtacttta agaagaggtt aatgaacaaa agagttgaaa aagctgacat ctgtaggctc    300
tgccttctca atgggaagat tacagtactc actgagggaa acaggataag atacagagat    360
gaatacatat gtgaaagttg tgccgaggag gagttgaaga gagagttaag atttcgattt    420
aattccatag gaatgcttga acaggcaaag aagcttttag agagattcag agatttagac    480
aaggtgattt caattttga tccatccttt gaccccacta gcatccaga gataacaaaa    540 tgggatgagc taaaggccaa gcatataagg gtcgagaaga tgcatataga tgagctcaac   600
atccccgaag aattcaaaaa agttctaaag gccgaaggaa taacgaact actccccgtt    660 caggtgctag cgattaaaaa cggcctccta gagggggaga atttattggt ggtttcagca    720
actgcgagtg gaaaaactct aatcggagag cttgcaggta ttcctaaggc tctaaaggga   780
aagaaaatgc tgttcctagt tcctctagta gctttagcaa accaaaagta cgaggacttc    840
aagagaagat actcaaagct tggattaaaa gtagccatta gagtcggaat gagcaggata    900
```

```
aagaccaagg aagagccaat agttctggat actggaacag atgcacacat aatagtgggg      960
acttacgaag gaatagacta ccttctcaga gctggtaaaa agataggaaa cgttggaacg     1020
gttgtaatag atgaaataca catgctcgat gatgaggaga gaggagctag gctagatggg     1080
ctcattgcaa ggttaaggaa gctctattca aatgcccaat ttattgggct ttcagcaacc     1140
gtaggaaacc ctcaggagtt agccaggaag ctagggatga aactagtgct ttacgatgaa     1200
aggcccgttg acttagagag gcatttaata attgcgagaa atgagagtga gaagtggagg     1260
tatatagcta agctgtgcaa agccgaggcc atgagaaaga gcgagaaggg attcaagggg     1320
cagacgatag tatttacatt ttcaaggaga agatgccatg agcttgcctc attcctaacg     1380
gggcagggat tgaaggctaa ggcctaccac tcgggcctcc cctatgttca gagaaagctt     1440
accgaaatgg agtttcaagc tcaaatgatt gatgtagttg taacaacagc tgctttagga     1500
gcgggagttg atttccagc atcccaagtc atcttcgaaa gcttggccat gggaaacaag     1560
tggataacag ttagggagtt tcaccaaatg cttggcaggg ctggaaggcc acagtaccat     1620
gagaaaggta agtttacat aatagtcgag cctgggaaaa agtactcagc tcagatggag     1680
ggaactgaag atgaagtcgc cctcaagctc ttgacttcac ccatagaacc agtaattgtt     1740
gagtggagcg atgaatttga agaggataat gtcttagctc atgcctgtgt gtttaataga     1800
cttaaagtta ttgaagaagt tcaatccctc tgcctgggag caaaccaaag tgctaaaaat     1860
gttttggaaa aacttatgga aaaggggctc gtcaaaatat atggagataa agttgaagca     1920
accccatatg aagggcggt gagcatgagt ttcctacttc ctagggaggc agagttcatc     1980
agagataact tggagagcac tgatccaatt gagatagcaa ttaaactgct accgttcgaa     2040
aacgtttacc tcccaggatc gctccagagg gaaatagagt cagctgttag aggaaagata     2100
agctcaaaca tcttttcaag ctcctttgca tcagtgctag aagagcttga caagattata     2160
cccgaaataa gcccaaatgc tgcagaaagg ctattcctaa tataccaaga tttcttcaac     2220
tgcccagagc aagactgtac ggagtttgca atggagagaa ttgggagaaa gatcattgac     2280
ttaagaagag agggatacga gccctcaaaa atctctgagc actttaggaa ggtctatgca     2340
ttaatattat accctggaga tgtttttaca tggttagacg gaattgtgag aaaactcgag     2400
gcaattgaaa gaatagcccg agtgttcaat aagagaagag tggtagaaga cacaatcagg     2460
gttagaaggg aaattgaaga aggaaaaatt ttgaagggtg agagacgatg a              2511
```

<210> SEQ ID NO 69
<211> LENGTH: 2943
<212> TYPE: DNA
<213> ORGANISM: Artificial Sequence
<220> FEATURE:
<223> OTHER INFORMATION: Description of Artificial Sequence: Recombinant helicase 4

<400> SEQUENCE: 69

```
atgcacaaat acttctttcc attacctgca actaagtcaa ctttcttgct ccctgccgac       60
ctcaccacag caaatccatg cttttccaag agcttaatca attctctctc tgcctgggcc      120 cctttctat acatacaatg ttttttcctat ctacctctta taaactttt aaactccttg      180 acataccctc tcgagatgca catattgata aaaaaggcaa taaagagag atttggaaag      240 ttgaatgccc ttcaacaatt agcctttcat aaaattaggg gagaaggtaa aagtgtttta      300
ataatagctc cgacaggaag cggaaaaact gaagccgcag taattccaat cttagacgca      360
atactacggg agaatcttaa acctatagca gctatttata tagcccccatt gaaggcacta      420
```

```
aatagggact tgctagagag actaaagtgg tgggaagaaa aaactggggt aataatagag    480
gttaggcatg gggacacgcc tacctcaaaa agattgaagc aggtaaaaaa tcctccccac    540
ctattaatta caaccccctga aatgctccct gctattctta cgacaaagtc cttccgtccc   600
tatcttaaga acactaaatt tatcgtgata gacgagattg gtgaacttat agagaataaa   660
agaggaaccc agctaatcct aaatctaaaa agacttgaat taattacaga agataaacca   720
ataaggattg gcctttctgc aacaattgga agtgaagaaa aggtaaggct ttggatggaa   780
gcggatgaag tggtaaagcc tcgactaaaa aagaagtaca aatttaccgt tttataccct   840
cagccaattc cagaggatga aaagcttgct gaagagctca aagttccaat agaagttgca   900
acgaggctaa gagttgtgtg ggatattgta gaaaagcaca agaaggtatt gatctttgtt   960
aatacccgac aatttgcaga gatcttaggg catagactta aagcttgggg aaaacctgtt  1020
gaagttcacc atggtagcct ttcaagggaa gcaagaatag aggcagagaa gaaacttaag  1080
gaaggaaaaa taaaagcact aatttgtacc tcatcaatgg aacttggcat tgacataggg  1140
gatgttgatg cagttattca gtacatgagt cctcgacagg taaataggct agtccagaga  1200 gctgaagaa gcaaacatag actgtgggaa acaagcgagg cttacatcat aaccacaaac  1260
gtagaagatt atctccaaag cttggcaata gcaaagctcg cactagaagg aaaactggaa  1320
gatgtaaatc cctacgaaaa tgcccttgat gtcctggctc actttatagt tggtttgaca  1380
atagaataca gaaatgttaa cattactgaa ccctattccc ttgcgaaatc tacttatccc  1440
tacagaaagc tctcctggga agactatcag aaagttttag agattttaga agaggctaga  1500
ataataagaa gagatggaga tgcaattaag ctgggaaaaa atgcctttaa gtattatttc  1560
gagaacctct caacaatacc tgacgaaata agttatgcag ttatagatat tgcaagtgga  1620
aaatctgttg gaagactaga tgaaaacttt gttacggaac ttgaagagag tatggaattc  1680
atcatgcatg gaagaagctg gatcgtgctg gaaattaacg aaaaagaaag gataataaag  1740
gttaaggaga gcaacaattt agaaagtgca ctgccaagtt gggaagggga gctcattcca  1800
gttcctttgg aagttgcaga atttgttgga aagctgaaga gagagctcct atgggacaaa  1860
gagagagcat taaaactgct tgagggcgtt gaatttaata aggaagaact cgaggttgca  1920
atttcccaac tagtagaatc agaaccagtg gcgagtgata gagatatcat tatagaatcc  1980
tatccaaaat ttgtgataat tcatgctgat tttggaaata aaattaacga agggctcaca  2040
agatttatct cagtgttttt atccgcccga tatgggaata ttttcctccc aagaagtcaa  2100
gctcatggaa ttataattag aagcccattt aggcttaatc ctgaagaaat aaaggaaata  2160
ctgttaatga aagcagaagt tggagatatt gttgctagag gaattagaga cactccaata  2220
taccgctgga agatgagtgc aattgctaag agattcggtg ccctaagaag ggacgcgaga  2280
ataaaaaaag tagaaaggct gtttgaaggg acaataatag agaaggagac ttttaatgaa  2340
atttaccatg ataaaatcga cattgataaa acagagaaaa ttctagaaaa aataagaaag  2400
ggagaaatta gaatgaaaac tttgttcaga gaggaaataa cgcctctttc ctcttctttg  2460
gcaaccctag gaggagagtt tctaattaga gatatactta cccaggagga agtagaagag  2520
atatttaggg agaagttact cgatgctgag ttagtcatgg tttgtacaaa ctgcggattt  2580
tcctggagaa caaaagttcg cagggttatg gatagagtca atgagttaag ctgtcccaag  2640
tgtgattcca aaatgatagc tcctctacac cccaaagatt ccgaaacttt catctcagct  2700
ctcaaaaagt taaaaagagg agaaaagctt agtagggaag aagaaaagta ttaccttaga  2760
ggtttaaagg cggctgattt acttaaagcc tacgggaagg acgctctttt agcattagct  2820
```

-continued

```
acctatgggg ttggggtaga aagcgccacc agaatactta gggattatag aggaaaatcc      2880
cttataaaag cacttatcga ggcagagaaa cactacatcc aaactagaaa gttttgggaa      2940
tag                                                                   2943

<210> SEQ ID NO 70
<211> LENGTH: 2295
<212> TYPE: DNA
<213> ORGANISM: Artificial Sequence
<220> FEATURE:
<223> OTHER INFORMATION: Description of Artificial Sequence: Recombinant
      helicase 5

<400> SEQUENCE: 70
gtgatgttat taaggagaga cttaatacag cctaggatat atcaagaggt aatatacgcc        60
aagtgcaaag aaacaaactg cttgattgtt ctgcccacag gattaggtaa gacgctgata       120
gctatgatga tagcagagta tagattaacg aaatatggcg gaaaagttct aatgctcgcc       180
cccactaagc ctctcgttct tcaacatgcg gaaagtttta ggaggctatt taacctccct       240
ccagaaaaaa ttgtagcact tactggagag aagagcccag aagagagaag taaggcctgg       300
gcgagagcaa aagtaattgt agccactcct caaactattg aaaatgactt attggcggga       360
agaatatctt tagaagacgt ttcgctaata gtattcgatg aagctcacag agctgtgggc       420
aattacgctt acgtctttat agcaagagag tataaaagac aggccaaaaa cccacttgtt       480 ataggggttaa cagcctcccc tgggagcact cctgaaaaga tcatggaggt aataaataac       540
ttgggaattg agcatattga ataccgctcc gaaaattctc ccgatgttag accttacgtt       600
aagggaataa ggtttgaatg ggttagggtt gatctcccag aaatatacaa ggaagtaagg       660
aaacttttaa gagaaatgct tagagatgcc cttaaaccgt tggcagaaac tggacttctt       720
gaatcttctt ccccagacat tccaaagaaa gaagttctta gagctgggca ataataaac       780 gaagaaatgg cgaaaggtaa tcatgatctc agaggcttgc ttctctatca cgcaatggct       840
cttaagctac atcatgcaat tgagctgttg gaaacccaag ggttatccgc cctgagggct       900
tatataaaga agttgtatga ggaggcaaaa gcgggatcaa caaaggctag caaggaaata       960
ttctcggata agagaatgaa aaaggcaatc tcactttttag ttcaagcgaa ggagattggg      1020
cttgatcacc ccaagatgga caagttaaaa gaataattga gggaacaact ccaaaggaaa      1080
caaaattcca aaatcatagt tttcactaac tacagagaaa ctgcaaaaaa gatagtcaat      1140
gaacttgtga agatggaat aaaagctaaa aggttcgttg acaggccag caaagaaaat       1200 gaccgtggac tgagtcagag agagcagaaa ttaattcttg acgaattcgc tagaggagaa      1260
ttcaacgttc tagtggcaac gagtgtagga gaggaaggac ttgacgtgcc ggaagttgat      1320
ttggttgtgt tttatgagcc agtaccatct gccataagga gcatccaaag aagggtaga      1380 actggcaggc atatgccggg gagagttata atcctaatgg ccaaggggac tagagatgaa      1440
gcatactact ggagttccag gcaaaaggaa aagataatgc aagagacaat agctaaggtg      1500
agtcaggcaa ttaaaaagca gaagcaaact tctctagttg attttgtgag agaaaaagag      1560
agcgaaaaga cctctctaga caagtggttg aaaaaggaaa aagaagaagc aactgaaaaa      1620
gaggaaaaga aggtaaaggc tcaagagggt gtaaaagtcg tcgtagatag cagagagctt      1680
aggagtgagg ttgtgaagag acttaaaactt cttggtgtaa agttagaggt taaaacgctc      1740
gatgtgggag attatataat tagtgaggac gttgcaattg agaggaagtc agctaacgac      1800
ttcattcagt caattattga tggtagactt tttgatcaag ttaagaggct caaagaggca      1860
```

| | |
|---|---|
| tactcaagac cgataatgat agtcgaaggt tctttatacg gaattagaaa cgtccatcca | 1920 |
| aatgcaataa gggggggcaat agcagcggta accgtagact ttggggtccc aataatattt | 1980 |
| tcatctactc cagaggaaac cgctcaatac atctttctaa ttgcaaagag ggagcaagag | 2040 |
| gagagagaaa aacctgtgag aattagaagt gagaagaagg cccttaccct tgccgagagg | 2100 |
| cagaggttaa tagttgaggg attacctcac gtctcagcaa ctctagctag gagattgttg | 2160 |
| aagcactttg gaagtgtgga aagggtattc actgcaagcg ttgctgagtt aatgaaagtt | 2220 |
| gaaggcatag gagagaagat tgctaaggag attagaaggg taataactgc cccatatata | 2280 |
| gaggatgagg agtag | 2295 |

<210> SEQ ID NO 71
<211> LENGTH: 2823
<212> TYPE: DNA
<213> ORGANISM: Artificial Sequence
<220> FEATURE:
<223> OTHER INFORMATION: Description of Artificial Sequence: Recombinant helicase 6

<400> SEQUENCE: 71

| | |
|---|---|
| ttgaaagggt tgtttaggga cgttatcctc cacaaccccc acctttttgt ttattcctat | 60 |
| tctgataaag gcatcattcc tttcaagcat cagttccaga ccctctatca tgccatgctc | 120 |
| atgaggccag tgaggctaat gatagctgat gagataggtc tcggaaagac cattcaagct | 180 |
| cttttaatag ccaagtacct cgattttagg ggagagattg agaaagcctt gatagtcgtt | 240 |
| ccaaaagttc tgagggagca gtggagggaa gaagtaaaga ggatcttaga ggaagctccg | 300 |
| gaagtgatag agaatggtag cgaaattgaa tggaagttga aaaggccgag gaagtacttc | 360 |
| ataatatcaa tagacctagc taagagatac accgaggaaa tactccgtca aaagtgggat | 420 |
| ttagtaatag ttgacgaagt ccacaacgcc accctgggaa cacagagata tgagttctta | 480 |
| aaagaactaa ccaagaacaa ggatttgaac gttatattcc tttcagcaac cccccacagg | 540 |
| ggaaacaata gagattacct tgcgaggctt aggctcctcg acccaactat accagaggaa | 600 |
| atatccccaa tgcacgaaag gaagatctac atgaagtcaa gagggacatt ggtactaagg | 660 |
| cgaactaaga aggttgtcaa cgaacttgaa ggagaagtgt tcaagaagtg tcactttggg | 720 |
| gctgtcgtgg tagaagttag cagagaggag agggagttct ttgaagagtt aaatagagcg | 780 |
| ctattcgagc tgattaagga tcaagctgat tactctccct taactcttct tgcagtaatc | 840 |
| attaggaaga gagcctcgtc cagctacgaa gcggctctaa aaacccctaac caggatcgtt | 900 |
| gaaagcgctt atataagtgg gcaagaaaga gccagaggcg ttgaatcata cattgaaaag | 960 |
| atctttagaa tggggtatga ggaattgaaa atagaagaat ttaacgagat agatgatgcg | 1020 |
| atacacaaaa taatagatga atataggga ttcttaactg aagagcaact cgaaaggctt | 1080 |
| agaagagttc tcgagcttgg aaagaaaatt ggcagcaagg atagcaagct tgaggttata | 1140 |
| tccgatatag ttgcttatca cattaggaac ggcgaaaagg tcataatatt cacggaattt | 1200 |
| agagataccc tcgaatacgt acttgagagg ttaccagata tcctaaggag aaagcacggc | 1260 |
| attgttttgg aaaagatgac cattgcaaaa cttcatgggg gcatgaaatc tgaggaaata | 1320 |
| gagagggaaa tcaacaagtt tcatgaaagg gctaacctat tagtctctac ggatgttgca | 1380 |
| tccgaaggac ttaacctgca cgttgcaagt gttgtaataa actacgaggc cccctggagc | 1440 |
| ccaataaagc tcgaacagag ggtgggaaga atatggaggc tcaaccaaac gagagaaacc | 1500 |
| aaagcatata ccatatttct tgcaacggaa acggacttgg atgttctaaa caacctctat | 1560 |

```
agaaagatta tgaacataaa ggaagccgtg ggaagtggac ccattattgg aaggccaata    1620
tttgaaggag actttgaaaa tctatggaat gaaggtgccg aggaagaaaa tagagaagtc    1680
tcagagtatg agcttatcct agcctcaatt aagggagaac tcaagggcta tgccggggct    1740
ctagttagga ctctcagaat cctaaagcag aaagtggagg gagcagttcc tgtaaatcct    1800
gcgggaagca taaggagaga gctcgagata attttagagg acactcctga tgtggaagta    1860
ttaaagaaaa tcgttaatag gaacgttcca aatccgttcc gcttggtgag aggactttta    1920
agagaagccg aggggattga gggaattaga gtattagtta agggctatga tggctctatg    1980
gatgtgtact atgccatatt ctacgacgaa gatgggagag aaatttatag atatccaatt    2040
cttgctgaga acggaaagta ccttgttgga ttcaacttac tcaagaggat tagtgaggta    2100
ctatccaaag agtacaaggt cgttagaggg gcaagtgaag aggtggacta taaagttaag    2160
acgctagtta tggacaacat atacaattta atcgtgaaga agtatctgga atacgatagc    2220
ttaaacatca aagaaggtaa aatcttcaag aggcttaagg ttgaaataaa gaaagccctc    2280
gaggtaaagg ggataagtga agaagaattc gaagtcatca agagagttcc ccctgagatt    2340
atggaagttc tagggttaga ttccacaaaa atagaactac ctaccaacga atacctcaag    2400
atcttcgaaa ggaactttgt tcctctggat aaaatccttg agagtgaaaa gaaggccatg    2460
gaaatagtca tggagctaga agagcagaga ggatataacg ttgaggacgt atctttaagg    2520
gagcactatg acataagggc cttttacagat ggtgaagaga agtacataga ggtcaaaggc    2580
cactatccaa tgctcctact tgcggagtta acggaaaagg aatttgagtt cgcacaaaaa    2640
aatgaagata agtactggat atacatagtc tcgaacattg ccaaagaccc cgtaattgta    2700
aaaatttaca aaccatttc ccaggataga agagtattcg tggttaagaa tggggaagat    2760
gttgaggtta atatcaacat tgagataaag aagaaagata ggcatttact taagttaagc    2820
tag                                                                  2823

<210> SEQ ID NO 72
<211> LENGTH: 3837
<212> TYPE: DNA
<213> ORGANISM: Artificial Sequence
<220> FEATURE:
<223> OTHER INFORMATION: Description of Artificial Sequence: Recombinant
      helicase 7

<400> SEQUENCE: 72
gtgattactt tggagctaca tccaagtgag atagctagat atttcgagct tgaagagtgt      60
tcccactatt tctctaacct actttttaaga aagagaggcg aattgcagga atttgagccg    120
ataataagga gaaagaaat agaaaccata gagctcgcca aatggggaga cgagttcgag    180
ctctcccttc ttcaggaatt taaaaaaggt gaagcattaa aaaagcttgg agttaaagaa    240
ctaccaagat tctatggttt tttaacggaa aacgacaccc ctgtaagaaa gttctttgaa    300
aagtacttta aagatggaat aatagtggaa gaagatccag acaaactttt agaaattata    360
aacagtgaga aaagtgccgt tatctatcaa gccccttaa aaggcagaat agggaaattt      420
gatgtctcag gaagggcaga cttcataata aaggttggga aaacactta cctactcgag    480 gctaagttta ctaaggaaga gaagttctac cacaggattc aggccattat ctatgctcac    540
cttctaagtc aaatgatcga aggttacgaa attaaactag ctgttgtaac aaaggagaac    600
tttcccattc cctcaaactt cctaagattc ccaggagacg tggaagagtt aaagataacc    660
ctagaagaaa agcttggtgg aatactaaga gaacaagaac tttggataga cgcaaggtgt    720
```

-continued

```
actacttgcc cctttgaggc tttatgcttg tctaaggctc ttgaggaaag aagtctagga      780
ctattaagcc ttccccctgg gataattaga atactcaaag aagaagggat aaaagactta      840
aaagacatgg ctaagctatt tgaattcaaa gaaaattccc ctacaaactt gaagagccc       900 tcaataaaag atccaaagaa gactcaagag atagcaaaaa gaacgggaat aaacttacta      960
aagctctcaa ggatagctca ggcaatcctt aaatatttag atgagggaga acaacaccc      1020 ctgttcatcc ccaggacggg gtataatctg ccaatggatg agagagtagg tgatgttgag     1080
ccctcttact atcctccaag gagcttagtg aaagtgttct tctatgtcca gacaagccca     1140
ataacagaca caataatcgg aatttcagcc cttgtaaaga ataggcaaaa tggagagcgg     1200
ataattgtta agttcgtcga tgagcccccc atagaagttt cagatgccca agaaaaggag     1260
agaatgcttc taattgagtt ctttagggat gttattgatg ccgtaaagtc actatctcca     1320
accgataaag tctacctaca catgtacttt tacaatagaa aacagagaga tgaccttatg     1380
gatgccgtaa agagacacaa agagataaga gaaaacaatg cagtcatggc cttgctaagc     1440
ttgagaagag ccatagattg ggagagcttt tcaataataa aggatgagat aataaggagg     1500
catgccttac cactttctcc tggcctggga ttcgttacag ttgctactca gtttggatac     1560
agatggagaa ggaacaaaac ctttgcgcga atgcttgagg ttgtagcaag aagagaaaat     1620
ggtaagataa atctcaaaac tctccttaac atttctgaaa cgggaattgg gccagaatat     1680
tatccaatca tcgataggga taacgaagga ataccctttca cacttttctg gagcgcactg    1740
gtcaaattag ctactgagga agacaattca agaattaaga gggatataag ggacatactc     1800
tcccaaatgg ttgaggccct caaaacaatt gaagagagaa ttcccgagca atataaagac     1860
gccttcgtga aaaagagggg aatacccaaa gaagatctcg aaaactttga cataaagaag     1920
gaagaattag ctgatatcct tcttgaatac ttacaattag agttcgatgc aagatttaga     1980
gaacgatccg aatactatag gcttccccta tcaataagag catactcaga ggaatcagca     2040
ctaattaaga tagaaaacat tgaaaagaag aaaaatgact gtctgttgtt tggaaaaatc     2100
gtgctaattg acgaaaatgg aagaataaaa gagtataatc caaaagaagt tcttatagat     2160
attgatgaag gttctcttgt agttgtaacg ccaaagaaat tcttagataa gctaagaaga     2220
gatcccgttc aaagaataag caaatcaccg ttaggaatag ttgaggctat agatcacgag     2280
acaggaaaag ttgttataag gttaataaga gtctctccag gcagatttac actcaaacac     2340 tctaagtttta gttgtaaaaa tggactattg acaataaccct atcctgaagg ggaagtgaaa     2400
gttactcctg gagagatagt tatagtagat cctagcgtcg atgacatagg aatggaaagg     2460
gcatacaatg tgctctcaga aatatcccaa ggggaactca agcatgaaat ttatcagaag     2520
gtcaaagcaa tatacgaagg gaacacggaa tcaagatacg aagtcaacat ctggaagaaa     2580
aagcacatag aagaatttct ctccagagtt aagaagatca acgaagaaca gaaaaagttt     2640
gcaattgaca taaacaactt tctagtcacc cttcaaggcc cccctgggac tgggaagaca     2700
tcaggggcca tagccccagc aattctcgca agagcatatt caatggtgaa ggacaaaaag     2760
aatggcctct ttgtagttac tggagtctca cacagggcag ttaatgaggc cctgataaag     2820
actttaaagc taaagaaaga gctggagaat acattaaaag agcttagaaa gatagatcta     2880
attagagcag tctctgggga agaggcaatc aaaataatta agaggaact agagagggaa     2940 ataaaggatg atgtcgacag aattagattt acagcacaag aaattaccca ctccttcaaag    3000 caaagatcat tagacaaata ttttgctaat tctggaactg tgaggatagt atttggaaca     3060
ccacagactt tgaacaagct tatgaagaat acaaaagaag tcgaactagt tgtcatagat     3120
```

| | |
|---|---|
| gaagctagta tgatggactt accaatgttc ttcctctcaa caaaagtttg taaaggtcaa | 3180 |
| gttctcttgg tcggggatca caggcagatg gagccaattc aagtccatga atggcaatta | 3240 |
| gaggacagaa agacatttga agagcactat ccattccttt cagcccttaa cttcattaga | 3300 |
| tttctcaggg gagagttgga tgaaagagaa cttaagaagt ttaagagaat ccttggaagg | 3360 |
| gaacctccag aatggaagaa ggacaagaac gaggttctcc ctctctatag gttagtaaga | 3420 |
| acttataggt tgccccagga aatagctgat ctactgagtg atgcaatata cagagcagat | 3480 |
| ggcataaaat tgattagtga aaagaaaaag aggagaaaga taattgccag gcacaaggat | 3540 |
| gagtttctat cgatagtttt agatgacagg tatccttttcg ttctaatact tcatgacgag | 3600 |
| ggcaattcca caaagattaa cgagctggaa gcaaagatag tagagaagat aatcaaaaga | 3660 |
| gtagagaata ttgatatagg agttgtagtt ccatatagac tcaaaagag attaatagct | 3720 |
| tcattaatag atagtgccca ggtggacaca gttgagagat tccaaggggg agagaaatct | 3780 |
| ttaatagtaa tttcaatgac ttccagcgac ccccgcatac ctgggaaagg tttttga | 3837 |

<210> SEQ ID NO 73
<211> LENGTH: 1968
<212> TYPE: DNA
<213> ORGANISM: Artificial Sequence
<220> FEATURE:
<223> OTHER INFORMATION: Description of Artificial Sequence: Recombinant helicase dna2

<400> SEQUENCE: 73

| | |
|---|---|
| atgaacataa agagcttcat aaacaggctt aaggagctag ttgaaatcga gagggaagct | 60 |
| gaaatagagg ctatgaggtt ggagatgaaa aggcttagcg gagtggagag ggagaggtta | 120 |
| ggtagggcaa ttctcagctt aaacggtaaa atcgttggtg aagagctcgg ttatttcttg | 180 |
| gttaagtacg gaaggaataa ggagataaag accgagatca gcgttgggga tttggttgtt | 240 |
| ataagcaaga gggatcccct gaagagcgac ctcctgggaa ctgttgttga aaggggaag | 300 |
| agattcatcg tcgttgcctt agaaccagtc ccagagtggg cccttagaga tgtgaggata | 360 |
| gacctctacg ccaacgatat aacattcaag aggtggatcg aaaacctcga cagggttagg | 420 |
| aaggctggaa aaaaggcttt agagttttac ttaggtttag atgagccttc ccaggggag | 480 |
| gaagtgagct ttgaacccct tgataagagc ctaaacccct ctcaaaggaa agcgatagct | 540 |
| aaggctttag gtagtgaaga cttcttcctt atccacggcc cctttggaac tggaaagacg | 600 |
| aggactttag ttgagctgat taggcaggag gtaaagaggg ggaacaaagt tctagctaca | 660 |
| gctgagagca acgttgccgt ggacaattta gttgaaagat tggccaaaga tggagttaag | 720 |
| atagttaggg ttgggcaccc aagtagggtt tcgaggcatt tgcacgagac aactttagct | 780 |
| tacctcatta ctcagcacga gctctacggt gagcttaggg agcttagggt gatagggcag | 840 |
| agtttggcag agaagaggga cacatataca aagccgactc caaagttcag gaggggactg | 900 |
| agtgatgctg agataattaa gttggccgag aagggaagag gggctagagg actctcagct | 960 |
| agactaataa aggagatggc cgagtggata aagctaaaca ggcaggttca gaaggccttt | 1020 |
| gaagatgcta gaaagcttga ggagaggatt gcgagggata taattaggga agccgatgtg | 1080 |
| gttttgacaa ctaactcttc tgcagcccctt gatgttgttg atgctaccga ttatgatgtt | 1140 |
| gcgataatag atgaagcaac tcaggcaact ataccgagca tattaataccc tctcaacaag | 1200 |
| gttgataggt ttatacttgc tggagaccac aagcaactac caccaactat cttaagcttg | 1260 |
| gaggcccagg agctctccca cacgcttttc gagggtttaa ttgagaagta cccatggaag | 1320 |

-continued

```
agcgaaatgc tgacaattca gtataggatg aatgagagga taatggagtt tccgagcagg  1380
gagttttacg atggaagaat agttgctgat gaaagtgtaa aaaacataac tctggccgac  1440
ctgggaatta agttaatgc tagtggaata tggagggaca tcctagatcc aaacaacgtc   1500
ctcgtgttca tagatacttg catgctcgaa ataggttcg agaggcagag aaggggaagc   1560
gaaagcaggg agaatccctt ggaggccaag atagtgagca aaatcgttga aaagctcttg   1620
gaaagtgggg ttaaagcgga aatgatggga gtgattacac cttacgatga ccagagggat   1680
ttgataagct tgaatgttcc cgaagaagtt gaggtcaaga ctgtggatgg ttaccaggga   1740
agggagaagg aagtgataat tctatcattt gtccgctcta acaaagcggg agagatcggc   1800
tttctcaagg acttgaggag gctaaacgtg tccttaacta gggctaagag gaagcttatc   1860
atgattggcg attcctcaac gctttcatct cacgaaacct acaggaggtt aatcgagcac   1920
gtgagggaga aggggttata tgttgtgcta acgaaggata gcatttga               1968
```

<210> SEQ ID NO 74
<211> LENGTH: 867
<212> TYPE: PRT
<213> ORGANISM: Artificial Sequence
<220> FEATURE:
<223> OTHER INFORMATION: Description of Artificial Sequence: Helicase 2

<400> SEQUENCE: 74

```
Met Ile Glu Glu Leu Phe Lys Gly Leu Glu Ser Glu Ile Val Gly Leu
  1               5                  10                  15

His Glu Ile Pro Pro Lys Arg Gly Glu Tyr Gly Glu Phe Lys Phe Arg
                 20                  25                  30

Asn Glu Glu Val Asn Glu Leu Val Lys Arg Leu Gly Phe Arg Leu Tyr
             35                  40                  45

Ser His Gln Val Lys Ala Leu Glu Lys Leu Tyr Ser Gly Lys Asn Val
         50                  55                  60

Val Val Ser Thr Pro Thr Ala Ser Gly Lys Ser Glu Ile Phe Arg Leu
 65                  70                  75                  80

Phe Ile Phe Asp Glu Ile Leu Ser Ser Pro Ser Ser Thr Phe Leu Leu
                 85                  90                  95

Ile Tyr Pro Thr Arg Ala Leu Ile Asn Asn Gln Met Glu Lys Phe Glu
            100                 105                 110

Lys Glu Asn Thr Ile Phe Glu Glu Ile Cys Gly Lys Arg Val Arg Ala
        115                 120                 125

Glu Val Leu Thr Gly Asp Thr Glu Trp Glu Lys Arg Arg Glu Ile Ile
    130                 135                 140

Arg Ser Lys Pro Asn Val Ile Phe Thr Thr Pro Asp Met Leu His His
145                 150                 155                 160

His Ile Leu Pro Arg Trp Arg Asp Tyr Phe Trp Leu Leu Lys Gly Leu
                165                 170                 175

Arg Leu Leu Val Val Asp Glu Leu His Val Tyr Arg Gly Ile Phe Gly
            180                 185                 190

Thr Asn Val Ala Tyr Val Phe Lys Arg Leu Phe Leu Arg Leu Lys Arg
        195                 200                 205

Leu Ser Ser Ser Pro Gln Ile Leu Ala Leu Ser Ala Thr Leu Arg Asn
    210                 215                 220

Pro Lys Glu Phe Ala Glu Gln Phe Glu Thr Glu Phe Glu Glu Val
225                 230                 235                 240

Lys Glu Ala Gly Ser Pro Ser Pro Arg Arg Ile Ile Val Met Phe Glu
                245                 250                 255
```

```
Pro Arg Arg Phe Thr Gly Glu Gln Leu Ile Lys Gln Ile Val Glu Arg
            260                 265                 270
Leu Thr Arg Lys Asn Ile Lys Thr Leu Val Phe Phe Asp Ser Arg Lys
        275                 280                 285
Gly Thr Glu Arg Ile Met Arg Leu Phe Leu Phe Ser Asp Ala Phe Asp
    290                 295                 300
Arg Ile Thr Thr Tyr Lys Gly Thr Leu Thr Lys Arg Glu Arg Phe Leu
305                 310                 315                 320
Ile Glu Arg Asp Phe Arg Glu Gly Asn Leu Thr Val Leu Leu Thr Thr
                325                 330                 335
Asn Ala Leu Glu Leu Gly Ile Asp Ile Gly Asp Leu Asp Ala Val Ile
            340                 345                 350
Asn Tyr Gly Ile Pro Ser Asp Gly Leu Phe Ser Leu Ile Gln Arg Phe
        355                 360                 365
Gly Arg Ala Gly Arg Asp Pro Asn Arg Ile Ala Ile Asn Gly Ile Ile
    370                 375                 380
Leu Arg Arg Asn Gly Leu Asp Tyr Tyr Tyr Lys Glu His Phe Asp Glu
385                 390                 395                 400
Leu Val Glu Gly Ile Glu Lys Gly Leu Val Glu Lys Ile Pro Val Asn
                405                 410                 415
Leu Asp Asn Glu Lys Ile Ala Lys Lys His Leu His Tyr Ala Ile Ala
            420                 425                 430
Glu Leu Gly Val Val Ser Ile Lys Glu Ile Glu Gly Arg Trp Lys Arg
        435                 440                 445
Phe Ile Lys Thr Leu Val Glu Glu Gly Tyr Val Glu Val Thr Arg Asn
    450                 455                 460
Pro Ile Thr Gly Glu Glu Glu Ile Arg Leu Arg Arg Pro Pro Val Tyr
465                 470                 475                 480
Ser Ser Ile Arg Thr Ala Ser Asp Glu Ser Tyr Phe Leu Val Val Asp
                485                 490                 495
Glu Pro Trp Ile Arg Gly Ala Leu Gln Arg Lys Arg Gly Ala Glu Leu
            500                 505                 510
Leu Arg Phe Val Asn Tyr Leu Lys Val Arg Gly Met Val Val Glu Glu
        515                 520                 525
Val Asp Glu Ile Glu Phe His Arg Ser Leu Leu Pro Gly Met Val Tyr
    530                 535                 540
Leu Ser Arg Gly Arg Pro Tyr Met Ala Val Asp Lys Ile Lys Ile Glu
545                 550                 555                 560
Lys Phe His Phe Val Phe Ala Arg Pro Leu Pro Ile Glu Glu Glu Ile
                565                 570                 575
Asp Thr Ser Ser Ser Lys Ile Glu Asn Ile Glu Ile Leu Glu Val Lys
            580                 585                 590
Asp Glu Lys Thr Val Gly Pro Ile Lys Val Lys Phe Gly Arg Leu Arg
        595                 600                 605
Val Arg His Glu Tyr Thr Gly Tyr Ala Val Arg Gly Arg Asp Val Glu
    610                 615                 620
Arg His Val Lys Arg Leu Glu Glu Leu Lys Asp Glu Gly Ile Leu Arg
625                 630                 635                 640
Gly Glu Ile Asp Ile Val Pro Tyr Ile Trp Glu Ser Trp Lys Phe Ala
                645                 650                 655
Arg Val Leu Phe Asp Thr Pro Tyr Ile Arg Glu Phe Glu Thr Glu Gly
            660                 665                 670
```

```
Phe Trp Leu Glu Phe Pro Asn Asp Ile Arg Ile Val Pro Glu Glu Glu
            675                 680                 685

Phe Arg Glu Phe Phe Ala Val Ala Ser Glu Ile Asp Pro Glu Leu Ala
        690                 695                 700

Met Phe Leu Tyr Asn Arg Ile Ser Arg Lys Ser Leu Phe Pro Thr Leu
705                 710                 715                 720

Leu Gly Ala Thr Thr His Tyr Ile Arg Ser Phe Ile Leu His His Ala
                725                 730                 735

Lys Asp Lys Gly Glu Glu Phe Ala Phe Ala Val Lys Lys Met Ile Asp
            740                 745                 750

Ser Lys Asp Gly Ile Gly Ser Gly Leu His Ala Ile Glu Pro Asn Ile
        755                 760                 765

Ile Lys Leu Ala Pro Val Val Thr His Val Asp Ser Arg Glu Ile Gly
770                 775                 780

Gly Tyr Ser Tyr Asp Asp Phe His Gly Lys Pro Val Ile Phe Ile Tyr
785                 790                 795                 800

Asp Gly Asn Glu Gly Gly Ser Gly Ile Ile Arg Gln Val Tyr Glu Asn
                805                 810                 815

Val Glu Lys Leu Met Tyr Arg Ser Leu Glu His Ile Lys Lys Cys Pro
            820                 825                 830

Cys Lys Asp Gly Cys Pro Ala Cys Ile Tyr Ser Pro Lys Cys Gly Thr
        835                 840                 845

Phe Asn Glu Phe Leu Asp Lys Trp Met Ala Ile Arg Ile Trp Glu Lys
    850                 855                 860

Val Leu Pro
865

<210> SEQ ID NO 75
<211> LENGTH: 836
<212> TYPE: PRT
<213> ORGANISM: Artificial Sequence
<220> FEATURE:
<223> OTHER INFORMATION: Description of Artificial Sequence: Helicase 3

<400> SEQUENCE: 75

Met Leu Ile Val Val Arg Pro Gly Arg Lys Lys Asn Glu Leu Glu Ala
  1               5                  10                  15

Phe Ile Ile Glu Asn Pro Pro Glu Lys Leu Ser Gln Arg Arg Asn Leu
            20                  25                  30

Lys Ala Asp Arg Val Val Arg Leu Ile Met Arg Asp Asn Arg Leu Phe
        35                  40                  45

Lys Ala Leu Glu Gly Ser Gln Tyr Leu Asn Pro Lys Glu Val Glu Arg
    50                  55                  60

Ala Leu Arg Asn Ser Arg Ile Val Leu Val Asn Ala Asn Glu Trp Glu
65                  70                  75                  80

Glu Tyr Phe Lys Lys Arg Leu Met Asn Lys Arg Val Glu Lys Ala Asp
                85                  90                  95

Ile Cys Arg Leu Cys Leu Leu Asn Gly Lys Ile Thr Val Leu Thr Glu
            100                 105                 110

Gly Asn Arg Ile Arg Tyr Arg Asp Glu Tyr Ile Cys Glu Ser Cys Ala
        115                 120                 125

Glu Glu Glu Leu Lys Arg Glu Leu Arg Phe Arg Phe Asn Ser Ile Gly
    130                 135                 140

Met Leu Glu Gln Ala Lys Lys Leu Leu Glu Arg Phe Arg Asp Leu Asp
145                 150                 155                 160
```

-continued

```
Lys Val Ile Ser Ile Phe Asp Pro Ser Phe Asp Pro Thr Lys His Pro
                165                 170                 175
Glu Ile Thr Lys Trp Asp Glu Leu Lys Ala Lys His Ile Arg Val Glu
            180                 185                 190
Lys Met His Ile Asp Glu Leu Asn Ile Pro Glu Glu Phe Lys Lys Val
        195                 200                 205
Leu Lys Ala Glu Gly Ile Asn Glu Leu Leu Pro Val Gln Val Leu Ala
    210                 215                 220
Ile Lys Asn Gly Leu Leu Gly Glu Asn Leu Leu Val Val Ser Ala
225                 230                 235                 240
Thr Ala Ser Gly Lys Thr Leu Ile Gly Glu Leu Ala Gly Ile Pro Lys
                245                 250                 255
Ala Leu Lys Gly Lys Lys Met Leu Phe Leu Val Pro Leu Val Ala Leu
            260                 265                 270
Ala Asn Gln Lys Tyr Glu Asp Phe Lys Arg Arg Tyr Ser Lys Leu Gly
        275                 280                 285
Leu Lys Val Ala Ile Arg Val Gly Met Ser Arg Ile Lys Thr Lys Glu
    290                 295                 300
Glu Pro Ile Val Leu Asp Thr Gly Thr Asp Ala His Ile Ile Val Gly
305                 310                 315                 320
Thr Tyr Glu Gly Ile Asp Tyr Leu Leu Arg Ala Gly Lys Lys Ile Gly
                325                 330                 335
Asn Val Gly Thr Val Val Ile Asp Glu Ile His Met Leu Asp Asp Glu
            340                 345                 350
Glu Arg Gly Ala Arg Leu Asp Gly Leu Ile Ala Arg Leu Arg Lys Leu
        355                 360                 365
Tyr Ser Asn Ala Gln Phe Ile Gly Leu Ser Ala Thr Val Gly Asn Pro
    370                 375                 380
Gln Glu Leu Ala Arg Lys Leu Gly Met Lys Leu Val Leu Tyr Asp Glu
385                 390                 395                 400
Arg Pro Val Asp Leu Glu Arg His Leu Ile Ile Ala Arg Asn Glu Ser
                405                 410                 415
Glu Lys Trp Arg Tyr Ile Ala Lys Leu Cys Lys Ala Glu Ala Met Arg
            420                 425                 430
Lys Ser Glu Lys Gly Phe Lys Gly Gln Thr Ile Val Phe Thr Phe Ser
        435                 440                 445
Arg Arg Arg Cys His Glu Leu Ala Ser Phe Leu Thr Gly Gln Gly Leu
    450                 455                 460
Lys Ala Lys Ala Tyr His Ser Gly Leu Pro Tyr Val Gln Arg Lys Leu
465                 470                 475                 480
Thr Glu Met Glu Phe Gln Ala Gln Met Ile Asp Val Val Thr Thr
                485                 490                 495
Ala Ala Leu Gly Ala Gly Val Asp Phe Pro Ala Ser Gln Val Ile Phe
            500                 505                 510
Glu Ser Leu Ala Met Gly Asn Lys Trp Ile Thr Val Arg Glu Phe His
        515                 520                 525
Gln Met Leu Gly Arg Ala Gly Arg Pro Gln Tyr His Glu Lys Gly Lys
    530                 535                 540
Val Tyr Ile Ile Val Glu Pro Gly Lys Lys Tyr Ser Ala Gln Met Glu
545                 550                 555                 560
Gly Thr Glu Asp Glu Val Ala Leu Lys Leu Leu Thr Ser Pro Ile Glu
                565                 570                 575
```

```
Pro Val Ile Val Glu Trp Ser Asp Glu Phe Glu Asp Asn Val Leu
            580                 585                 590

Ala His Ala Cys Val Phe Asn Arg Leu Lys Val Ile Glu Glu Val Gln
            595                 600                 605

Ser Leu Cys Leu Gly Ala Asn Gln Ser Ala Lys Asn Val Leu Glu Lys
    610                 615                 620

Leu Met Glu Lys Gly Leu Val Lys Ile Tyr Gly Asp Lys Val Glu Ala
625                 630                 635                 640

Thr Pro Tyr Gly Arg Ala Val Ser Met Ser Phe Leu Leu Pro Arg Glu
                645                 650                 655

Ala Glu Phe Ile Arg Asp Asn Leu Glu Ser Thr Asp Pro Ile Glu Ile
                660                 665                 670

Ala Ile Lys Leu Leu Pro Phe Glu Asn Val Tyr Leu Pro Gly Ser Leu
            675                 680                 685

Gln Arg Glu Ile Glu Ser Ala Val Arg Gly Lys Ile Ser Ser Asn Ile
    690                 695                 700

Phe Ser Ser Ser Phe Ala Ser Val Leu Glu Glu Leu Asp Lys Ile Ile
705                 710                 715                 720

Pro Glu Ile Ser Pro Asn Ala Ala Glu Arg Leu Phe Leu Ile Tyr Gln
                725                 730                 735

Asp Phe Phe Asn Cys Pro Glu Gln Asp Cys Thr Glu Phe Ala Met Glu
                740                 745                 750

Arg Ile Gly Arg Lys Ile Ile Asp Leu Arg Arg Glu Gly Tyr Glu Pro
            755                 760                 765

Ser Lys Ile Ser Glu His Phe Arg Lys Val Tyr Ala Leu Ile Leu Tyr
    770                 775                 780

Pro Gly Asp Val Phe Thr Trp Leu Asp Gly Ile Val Arg Lys Leu Glu
785                 790                 795                 800

Ala Ile Glu Arg Ile Ala Arg Val Phe Asn Lys Arg Val Val Glu
                805                 810                 815

Asp Thr Ile Arg Val Arg Arg Glu Ile Glu Glu Gly Lys Ile Leu Lys
                820                 825                 830

Gly Glu Arg Arg
        835

<210> SEQ ID NO 76
<211> LENGTH: 980
<212> TYPE: PRT
<213> ORGANISM: Artificial Sequence
<220> FEATURE:
<223> OTHER INFORMATION: Description of Artificial Sequence: Helicase 4

<400> SEQUENCE: 76

Met His Lys Tyr Phe Phe Pro Leu Pro Ala Thr Lys Ser Thr Phe Leu
1               5                   10                  15

Leu Pro Ala Asp Leu Thr Thr Ala Asn Pro Cys Phe Ser Lys Ser Leu
                20                  25                  30

Ile Asn Ser Leu Ser Ala Trp Ala Pro Phe Leu Tyr Ile Gln Cys Phe
            35                  40                  45

Ser Tyr Leu Pro Leu Ile Asn Phe Leu Asn Ser Leu Thr Tyr Pro Leu
    50                  55                  60

Glu Met His Ile Leu Ile Lys Lys Ala Ile Lys Glu Arg Phe Gly Lys
65                  70                  75                  80

Leu Asn Ala Leu Gln Gln Leu Ala Phe His Lys Ile Arg Gly Glu Gly
                85                  90                  95
```

-continued

```
Lys Ser Val Leu Ile Ile Ala Pro Thr Gly Ser Gly Lys Thr Glu Ala
            100                 105                 110
Ala Val Ile Pro Ile Leu Asp Ala Ile Leu Arg Glu Asn Leu Lys Pro
            115                 120                 125
Ile Ala Ala Ile Tyr Ile Ala Pro Leu Lys Ala Leu Asn Arg Asp Leu
        130                 135                 140
Leu Glu Arg Leu Lys Trp Trp Glu Lys Thr Gly Val Ile Ile Glu
145                 150                 155                 160
Val Arg His Gly Asp Thr Pro Thr Ser Lys Arg Leu Lys Gln Val Lys
                165                 170                 175
Asn Pro Pro His Leu Leu Ile Thr Thr Pro Glu Met Leu Pro Ala Ile
            180                 185                 190
Leu Thr Thr Lys Ser Phe Arg Pro Tyr Leu Lys Asn Thr Lys Phe Ile
            195                 200                 205
Val Ile Asp Glu Ile Gly Glu Leu Ile Glu Asn Lys Arg Gly Thr Gln
        210                 215                 220
Leu Ile Leu Asn Leu Lys Arg Leu Glu Leu Ile Thr Glu Asp Lys Pro
225                 230                 235                 240
Ile Arg Ile Gly Leu Ser Ala Thr Ile Gly Ser Glu Glu Lys Val Arg
                245                 250                 255
Leu Trp Met Glu Ala Asp Glu Val Val Lys Pro Arg Leu Lys Lys Lys
            260                 265                 270
Tyr Lys Phe Thr Val Leu Tyr Pro Gln Pro Ile Pro Glu Asp Glu Lys
            275                 280                 285
Leu Ala Glu Glu Leu Lys Val Pro Ile Glu Val Ala Thr Arg Leu Arg
        290                 295                 300
Val Val Trp Asp Ile Val Glu Lys His Lys Lys Val Leu Ile Phe Val
305                 310                 315                 320
Asn Thr Arg Gln Phe Ala Glu Ile Leu Gly His Arg Leu Lys Ala Trp
                325                 330                 335
Gly Lys Pro Val Glu Val His His Gly Ser Leu Ser Arg Glu Ala Arg
            340                 345                 350
Ile Glu Ala Glu Lys Lys Leu Lys Glu Gly Lys Ile Lys Ala Leu Ile
            355                 360                 365
Cys Thr Ser Ser Met Glu Leu Gly Ile Asp Ile Gly Asp Val Asp Ala
        370                 375                 380
Val Ile Gln Tyr Met Ser Pro Arg Gln Val Asn Arg Leu Val Gln Arg
385                 390                 395                 400
Ala Gly Arg Ser Lys His Arg Leu Trp Glu Thr Ser Glu Ala Tyr Ile
                405                 410                 415
Ile Thr Thr Asn Val Glu Asp Tyr Leu Gln Ser Leu Ala Ile Ala Lys
            420                 425                 430
Leu Ala Leu Glu Gly Lys Leu Glu Asp Val Asn Pro Tyr Glu Asn Ala
            435                 440                 445
Leu Asp Val Leu Ala His Phe Ile Val Gly Leu Thr Ile Glu Tyr Arg
        450                 455                 460
Asn Val Asn Ile Thr Glu Pro Tyr Ser Leu Ala Lys Ser Thr Tyr Pro
465                 470                 475                 480
Tyr Arg Lys Leu Ser Trp Glu Asp Tyr Gln Lys Val Leu Glu Ile Leu
                485                 490                 495
Glu Glu Ala Arg Ile Ile Arg Arg Asp Gly Asp Ala Ile Lys Leu Gly
            500                 505                 510
```

```
Lys Asn Ala Phe Lys Tyr Tyr Phe Glu Asn Leu Ser Thr Ile Pro Asp
            515                 520                 525

Glu Ile Ser Tyr Ala Val Ile Asp Ile Ala Ser Gly Lys Ser Val Gly
        530                 535                 540

Arg Leu Asp Glu Asn Phe Val Thr Glu Leu Glu Glu Ser Met Glu Phe
545                 550                 555                 560

Ile Met His Gly Arg Ser Trp Ile Val Leu Glu Ile Asn Glu Lys Glu
                565                 570                 575

Arg Ile Ile Lys Val Lys Glu Ser Asn Asn Leu Glu Ser Ala Leu Pro
            580                 585                 590

Ser Trp Glu Gly Glu Leu Ile Pro Val Pro Leu Glu Val Ala Glu Phe
        595                 600                 605

Val Gly Lys Leu Lys Arg Glu Leu Leu Trp Asp Lys Glu Arg Ala Leu
    610                 615                 620

Lys Leu Leu Glu Gly Val Glu Phe Asn Lys Glu Glu Leu Glu Val Ala
625                 630                 635                 640

Ile Ser Gln Leu Val Glu Ser Glu Pro Val Ala Ser Asp Arg Asp Ile
                645                 650                 655

Ile Ile Glu Ser Tyr Pro Lys Phe Val Ile His Ala Asp Phe Gly
            660                 665                 670

Asn Lys Ile Asn Glu Gly Leu Thr Arg Phe Ile Ser Val Phe Leu Ser
        675                 680                 685

Ala Arg Tyr Gly Asn Ile Phe Leu Pro Arg Ser Gln Ala His Gly Ile
    690                 695                 700

Ile Ile Arg Ser Pro Phe Arg Leu Asn Pro Glu Glu Ile Lys Glu Ile
705                 710                 715                 720

Leu Leu Met Lys Ala Glu Val Gly Asp Ile Val Ala Arg Gly Ile Arg
                725                 730                 735

Asp Thr Pro Ile Tyr Arg Trp Lys Met Ser Ala Ile Ala Lys Arg Phe
            740                 745                 750

Gly Ala Leu Arg Arg Asp Ala Arg Ile Lys Lys Val Glu Arg Leu Phe
        755                 760                 765

Glu Gly Thr Ile Ile Glu Lys Glu Thr Phe Asn Glu Ile Tyr His Asp
    770                 775                 780

Lys Ile Asp Ile Asp Lys Thr Glu Lys Ile Leu Glu Lys Ile Arg Lys
785                 790                 795                 800

Gly Glu Ile Arg Met Lys Thr Leu Phe Arg Glu Glu Ile Thr Pro Leu
                805                 810                 815

Ser Ser Ser Leu Ala Thr Leu Gly Gly Glu Phe Leu Ile Arg Asp Ile
            820                 825                 830

Leu Thr Gln Glu Glu Val Glu Glu Ile Phe Arg Glu Lys Leu Leu Asp
        835                 840                 845

Ala Glu Leu Val Met Val Cys Thr Asn Cys Gly Phe Ser Trp Arg Thr
    850                 855                 860

Lys Val Arg Arg Val Met Asp Arg Val Asn Glu Leu Ser Cys Pro Lys
865                 870                 875                 880

Cys Asp Ser Lys Met Ile Ala Pro Leu His Pro Lys Asp Ser Glu Thr
                885                 890                 895

Phe Ile Ser Ala Leu Lys Lys Leu Lys Arg Gly Glu Lys Leu Ser Arg
            900                 905                 910

Glu Glu Glu Lys Tyr Tyr Leu Arg Gly Leu Lys Ala Ala Asp Leu Leu
        915                 920                 925
```

-continued

```
Lys Ala Tyr Gly Lys Asp Ala Leu Leu Ala Leu Ala Thr Tyr Gly Val
            930                 935                 940

Gly Val Glu Ser Ala Thr Arg Ile Leu Arg Asp Tyr Arg Gly Lys Ser
945                 950                 955                 960

Leu Ile Lys Ala Leu Ile Glu Ala Glu Lys His Tyr Ile Gln Thr Arg
                965                 970                 975

Lys Phe Trp Glu
            980

<210> SEQ ID NO 77
<211> LENGTH: 764
<212> TYPE: PRT
<213> ORGANISM: Artificial Sequence
<220> FEATURE:
<223> OTHER INFORMATION: Description of Artificial Sequence: Helicase 5

<400> SEQUENCE: 77

Val Met Leu Leu Arg Arg Asp Leu Ile Gln Pro Arg Ile Tyr Gln Glu
 1               5                  10                  15

Val Ile Tyr Ala Lys Cys Lys Glu Thr Asn Cys Leu Ile Val Leu Pro
                20                  25                  30

Thr Gly Leu Gly Lys Thr Leu Ile Ala Met Met Ile Ala Glu Tyr Arg
            35                  40                  45

Leu Thr Lys Tyr Gly Gly Lys Val Leu Met Leu Ala Pro Thr Lys Pro
 50                  55                  60

Leu Val Leu Gln His Ala Glu Ser Phe Arg Arg Leu Phe Asn Leu Pro
 65                  70                  75                  80

Pro Glu Lys Ile Val Ala Leu Thr Gly Glu Lys Ser Pro Glu Glu Arg
                85                  90                  95

Ser Lys Ala Trp Ala Arg Ala Lys Val Ile Val Ala Thr Pro Gln Thr
            100                 105                 110

Ile Glu Asn Asp Leu Leu Ala Gly Arg Ile Ser Leu Glu Asp Val Ser
        115                 120                 125

Leu Ile Val Phe Asp Glu Ala His Arg Ala Val Gly Asn Tyr Ala Tyr
130                 135                 140

Val Phe Ile Ala Arg Glu Tyr Lys Arg Gln Ala Lys Asn Pro Leu Val
145                 150                 155                 160

Ile Gly Leu Thr Ala Ser Pro Gly Ser Thr Pro Glu Lys Ile Met Glu
                165                 170                 175

Val Ile Asn Asn Leu Gly Ile Glu His Ile Glu Tyr Arg Ser Glu Asn
            180                 185                 190

Ser Pro Asp Val Arg Pro Tyr Val Lys Gly Ile Arg Phe Glu Trp Val
        195                 200                 205

Arg Val Asp Leu Pro Glu Ile Tyr Lys Glu Val Arg Lys Leu Leu Arg
    210                 215                 220

Glu Met Leu Arg Asp Ala Leu Lys Pro Leu Ala Glu Thr Gly Leu Leu
225                 230                 235                 240

Glu Ser Ser Ser Pro Asp Ile Pro Lys Lys Glu Val Leu Arg Ala Gly
                245                 250                 255

Gln Ile Ile Asn Glu Glu Met Ala Lys Gly Asn His Asp Leu Arg Gly
            260                 265                 270

Leu Leu Leu Tyr His Ala Met Ala Leu Lys Leu His His Ala Ile Glu
        275                 280                 285

Leu Leu Glu Thr Gln Gly Leu Ser Ala Leu Arg Ala Tyr Ile Lys Lys
    290                 295                 300
```

```
Leu Tyr Glu Glu Ala Lys Ala Gly Ser Thr Lys Ala Ser Lys Glu Ile
305                 310                 315                 320

Phe Ser Asp Lys Arg Met Lys Lys Ala Ile Ser Leu Leu Val Gln Ala
                325                 330                 335

Lys Glu Ile Gly Leu Asp His Pro Lys Met Asp Lys Leu Lys Glu Ile
            340                 345                 350

Ile Arg Glu Gln Leu Gln Arg Lys Gln Asn Ser Lys Ile Ile Val Phe
        355                 360                 365

Thr Asn Tyr Arg Glu Thr Ala Lys Lys Ile Val Asn Glu Leu Val Lys
    370                 375                 380

Asp Gly Ile Lys Ala Lys Arg Phe Val Gly Gln Ala Ser Lys Glu Asn
385                 390                 395                 400

Asp Arg Gly Leu Ser Gln Arg Glu Gln Lys Leu Ile Leu Asp Glu Phe
                405                 410                 415

Ala Arg Gly Glu Phe Asn Val Leu Val Ala Thr Ser Val Gly Glu Glu
            420                 425                 430

Gly Leu Asp Val Pro Glu Val Asp Leu Val Val Phe Tyr Glu Pro Val
        435                 440                 445

Pro Ser Ala Ile Arg Ser Ile Gln Arg Arg Gly Arg Thr Gly Arg His
    450                 455                 460

Met Pro Gly Arg Val Ile Ile Leu Met Ala Lys Gly Thr Arg Asp Glu
465                 470                 475                 480

Ala Tyr Tyr Trp Ser Ser Arg Gln Lys Glu Lys Ile Met Gln Glu Thr
                485                 490                 495

Ile Ala Lys Val Ser Gln Ala Ile Lys Lys Gln Lys Gln Thr Ser Leu
            500                 505                 510

Val Asp Phe Val Arg Glu Lys Glu Ser Glu Lys Thr Ser Leu Asp Lys
        515                 520                 525

Trp Leu Lys Lys Glu Lys Glu Glu Ala Thr Glu Lys Glu Lys Lys
    530                 535                 540

Val Lys Ala Gln Glu Gly Val Lys Val Val Asp Ser Arg Glu Leu
545                 550                 555                 560

Arg Ser Glu Val Val Lys Arg Leu Lys Leu Leu Gly Val Lys Leu Glu
                565                 570                 575

Val Lys Thr Leu Asp Val Gly Asp Tyr Ile Ile Ser Glu Asp Val Ala
            580                 585                 590

Ile Glu Arg Lys Ser Ala Asn Asp Phe Ile Gln Ser Ile Ile Asp Gly
        595                 600                 605

Arg Leu Phe Asp Gln Val Lys Arg Leu Lys Glu Ala Tyr Ser Arg Pro
    610                 615                 620

Ile Met Ile Val Glu Gly Ser Leu Tyr Gly Ile Arg Asn Val His Pro
625                 630                 635                 640

Asn Ala Ile Arg Gly Ala Ile Ala Val Thr Val Asp Phe Gly Val
                645                 650                 655

Pro Ile Ile Phe Ser Ser Thr Pro Glu Glu Thr Ala Gln Tyr Ile Phe
            660                 665                 670

Leu Ile Ala Lys Arg Glu Gln Glu Glu Arg Glu Lys Pro Val Arg Ile
        675                 680                 685

Arg Ser Glu Lys Lys Ala Leu Thr Leu Ala Glu Arg Gln Arg Leu Ile
    690                 695                 700

Val Glu Gly Leu Pro His Val Ser Ala Thr Leu Ala Arg Arg Leu Leu
705                 710                 715                 720
```

```
Lys His Phe Gly Ser Val Glu Arg Val Phe Thr Ala Ser Val Ala Glu
                725                 730                 735

Leu Met Lys Val Glu Gly Ile Gly Glu Lys Ile Ala Lys Glu Ile Arg
            740                 745                 750

Arg Val Ile Thr Ala Pro Tyr Ile Glu Asp Glu Glu
        755                 760

<210> SEQ ID NO 78
<211> LENGTH: 940
<212> TYPE: PRT
<213> ORGANISM: Artificial Sequence
<220> FEATURE:
<223> OTHER INFORMATION: Description of Artificial Sequence: Helicase 6

<400> SEQUENCE: 78

Leu Lys Gly Leu Phe Arg Asp Val Ile Leu His Asn Pro His Leu Phe
 1               5                  10                  15

Val Tyr Ser Tyr Ser Asp Lys Gly Ile Ile Pro Phe Lys His Gln Phe
                20                  25                  30

Gln Thr Leu Tyr His Ala Met Leu Met Arg Pro Val Arg Leu Met Ile
            35                  40                  45

Ala Asp Glu Ile Gly Leu Gly Lys Thr Ile Gln Ala Leu Leu Ile Ala
    50                  55                  60

Lys Tyr Leu Asp Phe Arg Gly Glu Ile Glu Lys Ala Leu Ile Val Val
 65                 70                  75                  80

Pro Lys Val Leu Arg Glu Gln Trp Arg Glu Glu Val Lys Arg Ile Leu
                85                  90                  95

Glu Glu Ala Pro Glu Val Ile Glu Asn Gly Ser Glu Ile Glu Trp Lys
            100                 105                 110

Leu Lys Arg Pro Arg Lys Tyr Phe Ile Ile Ser Ile Asp Leu Ala Lys
        115                 120                 125

Arg Tyr Thr Glu Glu Ile Leu Arg Gln Lys Trp Asp Leu Val Ile Val
    130                 135                 140

Asp Glu Val His Asn Ala Thr Leu Gly Thr Gln Arg Tyr Glu Phe Leu
145                 150                 155                 160

Lys Glu Leu Thr Lys Asn Lys Asp Leu Asn Val Ile Phe Leu Ser Ala
                165                 170                 175

Thr Pro His Arg Gly Asn Asn Arg Asp Tyr Leu Ala Arg Leu Arg Leu
            180                 185                 190

Leu Asp Pro Thr Ile Pro Glu Glu Ile Ser Pro Met His Glu Arg Lys
        195                 200                 205

Ile Tyr Met Lys Ser Arg Gly Thr Leu Val Leu Arg Arg Thr Lys Lys
    210                 215                 220

Val Val Asn Glu Leu Glu Gly Glu Val Phe Lys Lys Cys His Phe Gly
225                 230                 235                 240

Ala Val Val Glu Val Ser Arg Glu Glu Arg Glu Phe Phe Glu Glu
                245                 250                 255

Leu Asn Arg Ala Leu Phe Glu Leu Ile Lys Asp Gln Ala Asp Tyr Ser
            260                 265                 270

Pro Leu Thr Leu Leu Ala Val Ile Ile Arg Lys Arg Ala Ser Ser Ser
        275                 280                 285

Tyr Glu Ala Ala Leu Lys Thr Leu Thr Arg Ile Val Glu Ser Ala Tyr
    290                 295                 300

Ile Ser Gly Gln Glu Arg Ala Arg Gly Val Glu Ser Tyr Ile Glu Lys
305                 310                 315                 320
```

-continued

```
Ile Phe Arg Met Gly Tyr Glu Glu Leu Glu Ile Glu Phe Asn Glu
            325                 330                 335

Ile Asp Asp Ala Ile His Lys Ile Ile Asp Glu Tyr Arg Gly Phe Leu
            340                 345                 350

Thr Glu Glu Gln Leu Glu Arg Leu Arg Arg Val Leu Glu Leu Gly Lys
            355                 360                 365

Lys Ile Gly Ser Lys Asp Ser Lys Leu Glu Val Ile Ser Asp Ile Val
370                 375                 380

Ala Tyr His Ile Arg Asn Gly Glu Lys Val Ile Ile Phe Thr Glu Phe
385                 390                 395                 400

Arg Asp Thr Leu Glu Tyr Val Leu Glu Arg Leu Pro Asp Ile Leu Arg
            405                 410                 415

Arg Lys His Gly Ile Val Leu Glu Lys Asp Asp Ile Ala Lys Leu His
            420                 425                 430

Gly Gly Met Lys Ser Glu Glu Ile Glu Arg Glu Ile Asn Lys Phe His
            435                 440                 445

Glu Arg Ala Asn Leu Leu Val Ser Thr Asp Val Ala Ser Glu Gly Leu
            450                 455                 460

Asn Leu His Val Ala Ser Val Val Ile Asn Tyr Glu Ala Pro Trp Ser
465                 470                 475                 480

Pro Ile Lys Leu Glu Gln Arg Val Gly Arg Ile Trp Arg Leu Asn Gln
            485                 490                 495

Thr Arg Glu Thr Lys Ala Tyr Thr Ile Phe Leu Ala Thr Glu Thr Asp
            500                 505                 510

Leu Asp Val Leu Asn Asn Leu Tyr Arg Lys Ile Met Asn Ile Lys Glu
            515                 520                 525

Ala Val Gly Ser Gly Pro Ile Ile Gly Arg Pro Ile Phe Glu Gly Asp
530                 535                 540

Phe Glu Asn Leu Trp Asn Glu Gly Ala Glu Glu Asn Arg Glu Val
545                 550                 555                 560

Ser Glu Tyr Glu Leu Ile Leu Ala Ser Ile Lys Gly Glu Leu Lys Gly
            565                 570                 575

Tyr Ala Gly Ala Leu Val Arg Thr Leu Arg Ile Leu Lys Gln Lys Val
            580                 585                 590

Glu Gly Ala Val Pro Val Asn Pro Ala Gly Ser Ile Arg Arg Glu Leu
            595                 600                 605

Glu Ile Ile Leu Glu Asp Thr Pro Asp Val Glu Val Leu Lys Lys Ile
            610                 615                 620

Val Asn Arg Asn Val Pro Asn Pro Phe Arg Leu Val Arg Gly Leu Leu
625                 630                 635                 640

Arg Glu Ala Glu Gly Ile Glu Gly Ile Arg Val Leu Val Lys Gly Tyr
            645                 650                 655

Asp Gly Ser Met Asp Val Tyr Tyr Ala Ile Phe Tyr Asp Glu Asp Gly
            660                 665                 670

Arg Glu Ile Tyr Arg Tyr Pro Ile Leu Ala Glu Asn Gly Lys Tyr Leu
            675                 680                 685

Val Gly Phe Asn Leu Leu Lys Arg Ile Ser Glu Val Leu Ser Lys Glu
            690                 695                 700

Tyr Lys Val Val Arg Gly Ala Ser Glu Glu Val Asp Tyr Lys Val Lys
705                 710                 715                 720

Thr Leu Val Met Asp Asn Ile Tyr Asn Leu Ile Val Lys Lys Tyr Leu
            725                 730                 735
```

-continued

```
Glu Tyr Asp Ser Leu Asn Ile Lys Glu Gly Lys Ile Phe Lys Arg Leu
                740                 745                 750

Lys Val Glu Ile Lys Lys Ala Leu Glu Val Lys Gly Ile Ser Glu Glu
        755                 760                 765

Glu Phe Glu Val Ile Lys Arg Val Pro Pro Glu Ile Met Glu Val Leu
    770                 775                 780

Gly Leu Asp Ser Thr Lys Ile Glu Leu Pro Thr Asn Glu Tyr Leu Lys
785                 790                 795                 800

Ile Phe Glu Arg Asn Phe Val Pro Leu Asp Lys Ile Leu Glu Ser Glu
                805                 810                 815

Lys Lys Ala Met Glu Ile Val Met Glu Leu Glu Lys Ser Arg Gly Tyr
            820                 825                 830

Asn Val Glu Asp Val Ser Leu Arg Glu His Tyr Asp Ile Arg Ala Phe
        835                 840                 845

Thr Asp Gly Glu Glu Lys Tyr Ile Glu Val Lys Gly His Tyr Pro Met
    850                 855                 860

Leu Leu Leu Ala Glu Leu Thr Glu Lys Glu Phe Glu Phe Ala Gln Lys
865                 870                 875                 880

Asn Glu Asp Lys Tyr Trp Ile Tyr Ile Val Ser Asn Ile Ala Lys Asp
                885                 890                 895

Pro Val Ile Val Lys Ile Tyr Lys Pro Phe Ser Gln Asp Arg Arg Val
            900                 905                 910

Phe Val Val Lys Asn Gly Glu Asp Val Glu Val Asn Ile Asn Ile Glu
        915                 920                 925

Ile Lys Lys Asp Arg His Leu Leu Lys Leu Ser
    930                 935                 940

<210> SEQ ID NO 79
<211> LENGTH: 1278
<212> TYPE: PRT
<213> ORGANISM: Artificial Sequence
<220> FEATURE:
<223> OTHER INFORMATION: Description of Artificial Sequence: Helicase 7

<400> SEQUENCE: 79

Val Ile Thr Leu Glu Leu His Pro Ser Glu Ile Ala Arg Tyr Phe Glu
  1               5                  10                  15

Leu Glu Glu Cys Ser His Tyr Phe Ser Asn Leu Leu Arg Lys Arg
                20                  25                  30

Gly Glu Leu Gln Glu Phe Glu Pro Ile Ile Arg Arg Lys Glu Ile Glu
            35                  40                  45

Thr Ile Glu Leu Ala Lys Trp Gly Asp Glu Phe Glu Leu Ser Leu Leu
    50                  55                  60

Gln Glu Phe Lys Lys Gly Glu Ala Leu Lys Lys Leu Gly Val Lys Glu
65                  70                  75                  80

Leu Pro Arg Phe Tyr Gly Phe Leu Thr Glu Asn Asp Thr Pro Val Arg
                85                  90                  95

Lys Phe Phe Glu Lys Tyr Phe Lys Asp Gly Ile Ile Val Glu Glu Asp
            100                 105                 110

Pro Asp Lys Leu Leu Glu Ile Ile Asn Ser Glu Lys Ser Ala Val Ile
    115                 120                 125

Tyr Gln Ala Pro Leu Lys Gly Arg Ile Gly Lys Phe Asp Val Ser Gly
    130                 135                 140

Arg Ala Asp Phe Ile Ile Lys Val Gly Lys Thr Leu Tyr Leu Leu Glu
145                 150                 155                 160
```

```
Ala Lys Phe Thr Lys Glu Glu Lys Phe Tyr His Arg Ile Gln Ala Ile
            165                 170                 175

Ile Tyr Ala His Leu Leu Ser Gln Met Ile Glu Gly Tyr Glu Ile Lys
            180                 185                 190

Leu Ala Val Val Thr Lys Glu Asn Phe Pro Ile Pro Ser Asn Phe Leu
            195                 200                 205

Arg Phe Pro Gly Asp Val Glu Glu Leu Lys Ile Thr Leu Glu Glu Lys
210                 215                 220

Leu Gly Gly Ile Leu Arg Glu Gln Glu Leu Trp Ile Asp Ala Arg Cys
225                 230                 235                 240

Thr Thr Cys Pro Phe Glu Ala Leu Cys Leu Ser Lys Ala Leu Glu Glu
            245                 250                 255

Arg Ser Leu Gly Leu Leu Ser Leu Pro Pro Gly Ile Ile Arg Ile Leu
            260                 265                 270

Lys Glu Glu Gly Ile Lys Asp Leu Lys Asp Met Ala Lys Leu Phe Glu
            275                 280                 285

Phe Lys Glu Asn Ser Pro Thr Asn Phe Glu Glu Pro Ser Ile Lys Asp
            290                 295                 300

Pro Lys Lys Thr Gln Glu Ile Ala Lys Arg Thr Gly Ile Asn Leu Leu
305                 310                 315                 320

Lys Leu Ser Arg Ile Ala Gln Ala Ile Leu Lys Tyr Leu Asp Glu Gly
            325                 330                 335

Glu Thr Thr Pro Leu Phe Ile Pro Arg Thr Gly Tyr Asn Leu Pro Met
            340                 345                 350

Asp Glu Arg Val Gly Asp Val Glu Pro Ser Tyr Tyr Pro Pro Arg Ser
            355                 360                 365

Leu Val Lys Val Phe Phe Tyr Val Gln Thr Ser Pro Ile Thr Asp Thr
            370                 375                 380

Ile Ile Gly Ile Ser Ala Leu Val Lys Asn Arg Gln Asn Gly Glu Arg
385                 390                 395                 400

Ile Ile Val Lys Phe Val Asp Glu Pro Pro Ile Glu Val Ser Asp Ala
            405                 410                 415

Gln Glu Lys Glu Arg Met Leu Leu Ile Glu Phe Phe Arg Asp Val Ile
            420                 425                 430

Asp Ala Val Lys Ser Leu Ser Pro Thr Asp Lys Val Tyr Leu His Met
            435                 440                 445

Tyr Phe Tyr Asn Arg Lys Gln Arg Asp Asp Leu Met Asp Ala Val Lys
            450                 455                 460

Arg His Lys Glu Ile Arg Glu Asn Asn Ala Val Met Ala Leu Leu Ser
465                 470                 475                 480

Leu Arg Arg Ala Ile Asp Trp Glu Ser Phe Ser Ile Ile Lys Asp Glu
            485                 490                 495

Ile Ile Arg Arg His Ala Leu Pro Leu Ser Pro Gly Leu Gly Phe Val
            500                 505                 510

Thr Val Ala Thr Gln Phe Gly Tyr Arg Trp Arg Asn Lys Thr Phe
            515                 520                 525

Ala Arg Met Leu Glu Val Val Ala Arg Arg Glu Asn Gly Lys Ile Asn
            530                 535                 540

Leu Lys Thr Leu Leu Asn Ile Ser Glu Thr Gly Ile Gly Pro Glu Tyr
545                 550                 555                 560

Tyr Pro Ile Ile Asp Arg Asp Asn Glu Gly Ile Pro Phe Thr Leu Phe
            565                 570                 575
```

-continued

```
Trp Ser Ala Leu Val Lys Leu Ala Thr Glu Glu Asp Asn Ser Arg Ile
            580                 585                 590

Lys Arg Asp Ile Arg Asp Ile Leu Ser Gln Met Val Glu Ala Leu Lys
        595                 600                 605

Thr Ile Glu Glu Arg Ile Pro Glu Gln Tyr Lys Asp Ala Phe Val Lys
    610                 615                 620

Lys Glu Gly Ile Pro Lys Glu Asp Leu Glu Asn Phe Asp Ile Lys Lys
625                 630                 635                 640

Glu Glu Leu Ala Asp Ile Leu Leu Glu Tyr Leu Gln Leu Glu Phe Asp
            645                 650                 655

Ala Arg Phe Arg Glu Arg Ser Glu Tyr Tyr Arg Leu Pro Leu Ser Ile
        660                 665                 670

Arg Ala Tyr Ser Glu Glu Ser Ala Leu Ile Lys Ile Glu Asn Ile Glu
    675                 680                 685

Lys Lys Lys Asn Asp Cys Leu Leu Phe Gly Lys Ile Val Leu Ile Asp
690                 695                 700

Glu Asn Gly Arg Ile Lys Glu Tyr Asn Pro Lys Glu Val Leu Ile Asp
705                 710                 715                 720

Ile Asp Glu Gly Ser Leu Val Val Thr Pro Lys Lys Phe Leu Asp
            725                 730                 735

Lys Leu Arg Arg Asp Pro Val Gln Arg Ile Ser Lys Ser Pro Leu Gly
        740                 745                 750

Ile Val Glu Ala Ile Asp His Glu Thr Gly Lys Val Val Ile Arg Leu
    755                 760                 765

Ile Arg Val Ser Pro Gly Arg Phe Thr Leu Lys His Ser Lys Phe Ser
770                 775                 780

Cys Lys Asn Gly Leu Leu Thr Ile Thr Tyr Pro Glu Gly Glu Val Lys
785                 790                 795                 800

Val Thr Pro Gly Glu Ile Val Ile Val Asp Pro Ser Val Asp Asp Ile
            805                 810                 815

Gly Met Glu Arg Ala Tyr Asn Val Leu Ser Glu Ile Ser Gln Gly Glu
        820                 825                 830

Leu Lys His Glu Ile Tyr Gln Lys Val Lys Ala Ile Tyr Glu Gly Asn
    835                 840                 845

Thr Glu Ser Arg Tyr Glu Val Asn Ile Trp Lys Lys His Ile Glu
850                 855                 860

Glu Phe Leu Ser Arg Val Lys Lys Ile Asn Glu Glu Gln Lys Lys Phe
865                 870                 875                 880

Ala Ile Asp Ile Asn Asn Phe Leu Val Thr Leu Gln Glu Pro Pro Gly
            885                 890                 895

Thr Gly Lys Thr Ser Gly Ala Ile Ala Pro Ala Ile Leu Ala Arg Ala
        900                 905                 910

Tyr Ser Met Val Lys Asp Lys Asn Gly Leu Phe Val Val Thr Gly
    915                 920                 925

Val Ser His Arg Ala Val Asn Glu Ala Leu Ile Lys Thr Leu Lys Leu
930                 935                 940

Lys Lys Glu Leu Glu Asn Thr Leu Lys Glu Leu Arg Lys Ile Asp Leu
945                 950                 955                 960

Ile Arg Ala Val Ser Gly Glu Glu Ala Ile Lys Ile Lys Glu Glu
            965                 970                 975

Leu Glu Arg Glu Ile Lys Asp Asp Val Asp Arg Ile Arg Phe Thr Ala
        980                 985                 990
```

```
Gln Glu Ile Thr His Ser Ser Lys Gln Arg Ser Leu Asp Lys Tyr Phe
        995                 1000                1005

Ala Asn Ser Gly Thr Val Arg Ile Val Phe Gly Thr Pro Gln Thr Leu
    1010                1015                1020

Asn Lys Leu Met Lys Asn Thr Lys Glu Val Glu Leu Val Val Ile Asp
1025                1030                1035                1040

Glu Ala Ser Met Met Asp Leu Pro Met Phe Phe Leu Ser Thr Lys Val
        1045                1050                1055

Cys Lys Gly Gln Val Leu Leu Val Gly Asp His Arg Gln Met Glu Pro
            1060                1065                1070

Ile Gln Val His Glu Trp Gln Leu Glu Asp Arg Lys Thr Phe Glu Glu
        1075                1080                1085

His Tyr Pro Phe Leu Ser Ala Leu Asn Phe Ile Arg Phe Leu Arg Gly
        1090                1095                1100

Glu Leu Asp Glu Arg Glu Leu Lys Lys Phe Lys Arg Ile Leu Gly Arg
1105                1110                1115                1120

Glu Pro Pro Glu Trp Lys Lys Asp Lys Asn Glu Val Leu Pro Leu Tyr
            1125                1130                1135

Arg Leu Val Arg Thr Tyr Arg Leu Pro Gln Ile Ala Asp Leu Leu
        1140                1145                1150

Ser Asp Ala Ile Tyr Arg Ala Asp Gly Ile Lys Leu Ile Ser Glu Lys
        1155                1160                1165

Lys Lys Arg Arg Lys Ile Ile Ala Arg His Lys Asp Glu Phe Leu Ser
        1170                1175                1180

Ile Val Leu Asp Asp Arg Tyr Pro Phe Val Leu Ile Leu His Asp Glu
1185                1190                1195                1200

Gly Asn Ser Thr Lys Ile Asn Glu Leu Glu Ala Lys Ile Val Glu Lys
            1205                1210                1215

Ile Ile Lys Arg Val Glu Asn Ile Asp Ile Gly Val Val Val Pro Tyr
        1220                1225                1230

Arg Ala Gln Lys Arg Leu Ile Ala Ser Leu Ile Asp Ser Ala Gln Val
        1235                1240                1245

Asp Thr Val Glu Arg Phe Gln Gly Gly Glu Lys Ser Leu Ile Val Ile
    1250                1255                1260

Ser Met Thr Ser Ser Asp Pro Arg Ile Pro Gly Lys Gly Phe
1265                1270                1275

<210> SEQ ID NO 80
<211> LENGTH: 655
<212> TYPE: PRT
<213> ORGANISM: Artificial Sequence
<220> FEATURE:
<223> OTHER INFORMATION: Description of Artificial Sequence: Helicase dna2

<400> SEQUENCE: 80

Met Asn Ile Lys Ser Phe Ile Asn Arg Leu Lys Glu Leu Val Glu Ile
1               5                   10                  15

Glu Arg Glu Ala Glu Ile Glu Ala Met Arg Leu Glu Met Lys Arg Leu
            20                  25                  30

Ser Gly Val Glu Arg Glu Arg Leu Gly Arg Ala Ile Leu Ser Leu Asn
        35                  40                  45

Gly Lys Ile Val Gly Glu Glu Leu Gly Tyr Phe Leu Val Lys Tyr Gly
    50                  55                  60

Arg Asn Lys Glu Ile Lys Thr Glu Ile Ser Val Gly Asp Leu Val Val
65                  70                  75                  80
```

-continued

```
Ile Ser Lys Arg Asp Pro Leu Lys Ser Asp Leu Leu Gly Thr Val Val
                85                  90                  95
Glu Lys Gly Lys Arg Phe Ile Val Val Ala Leu Glu Pro Val Pro Glu
            100                 105                 110
Trp Ala Leu Arg Asp Val Arg Ile Asp Leu Tyr Ala Asn Asp Ile Thr
        115                 120                 125
Phe Lys Arg Trp Ile Glu Asn Leu Asp Arg Val Arg Lys Ala Gly Lys
    130                 135                 140
Lys Ala Leu Glu Phe Tyr Leu Gly Leu Asp Glu Pro Ser Gln Gly Glu
145                 150                 155                 160
Glu Val Ser Phe Glu Pro Phe Asp Lys Ser Leu Asn Pro Ser Gln Arg
                165                 170                 175
Lys Ala Ile Ala Lys Ala Leu Gly Ser Glu Asp Phe Phe Leu Ile His
            180                 185                 190
Gly Pro Phe Gly Thr Gly Lys Thr Arg Thr Leu Val Glu Leu Ile Arg
        195                 200                 205
Gln Glu Val Lys Arg Gly Asn Lys Val Leu Ala Thr Ala Glu Ser Asn
    210                 215                 220
Val Ala Val Asp Asn Leu Val Glu Arg Leu Ala Lys Asp Gly Val Lys
225                 230                 235                 240
Ile Val Arg Val Gly His Pro Ser Arg Val Ser Arg His Leu His Glu
                245                 250                 255
Thr Thr Leu Ala Tyr Leu Ile Thr Gln His Glu Leu Tyr Gly Glu Leu
            260                 265                 270
Arg Glu Leu Arg Val Ile Gly Gln Ser Leu Ala Glu Lys Arg Asp Thr
        275                 280                 285
Tyr Thr Lys Pro Thr Pro Lys Phe Arg Arg Gly Leu Ser Asp Ala Glu
    290                 295                 300
Ile Ile Lys Leu Ala Glu Lys Gly Arg Gly Ala Arg Gly Leu Ser Ala
305                 310                 315                 320
Arg Leu Ile Lys Glu Met Ala Glu Trp Ile Lys Leu Asn Arg Gln Val
                325                 330                 335
Gln Lys Ala Phe Glu Asp Ala Arg Lys Leu Glu Glu Arg Ile Ala Arg
            340                 345                 350
Asp Ile Ile Arg Glu Ala Asp Val Val Leu Thr Thr Asn Ser Ser Ala
        355                 360                 365
Ala Leu Asp Val Val Asp Ala Thr Asp Tyr Asp Val Ala Ile Ile Asp
    370                 375                 380
Glu Ala Thr Gln Ala Thr Ile Pro Ser Ile Leu Ile Pro Leu Asn Lys
385                 390                 395                 400
Val Asp Arg Phe Ile Leu Ala Gly Asp His Lys Gln Leu Pro Pro Thr
                405                 410                 415
Ile Leu Ser Leu Glu Ala Gln Glu Leu Ser His Thr Leu Phe Glu Gly
            420                 425                 430
Leu Ile Glu Lys Tyr Pro Trp Lys Ser Glu Met Leu Thr Ile Gln Tyr
        435                 440                 445
Arg Met Asn Glu Arg Ile Met Glu Phe Pro Ser Arg Glu Phe Tyr Asp
    450                 455                 460
Gly Arg Ile Val Ala Asp Glu Ser Val Lys Asn Ile Thr Leu Ala Asp
465                 470                 475                 480
Leu Gly Ile Lys Val Asn Ala Ser Gly Ile Trp Arg Asp Ile Leu Asp
                485                 490                 495
```

|   |   |   |   |   |   |   |   |   |   |   |   |   |
|---|---|---|---|---|---|---|---|---|---|---|---|---|
| Pro | Asn | Asn | Val | Leu | Val | Phe | Ile | Asp | Thr | Cys | Met | Leu | Glu | Asn | Arg |
| | | 500 | | | | | 505 | | | | | 510 | | | |
| Phe | Glu | Arg | Gln | Arg | Arg | Gly | Ser | Glu | Ser | Arg | Glu | Asn | Pro | Leu | Glu |
| | | 515 | | | | | 520 | | | | | 525 | | | |
| Ala | Lys | Ile | Val | Ser | Lys | Ile | Val | Glu | Lys | Leu | Leu | Glu | Ser | Gly | Val |
| | | 530 | | | | | 535 | | | | | 540 | | | |
| Lys | Ala | Glu | Met | Met | Gly | Val | Ile | Thr | Pro | Tyr | Asp | Asp | Gln | Arg | Asp |
| 545 | | | | | 550 | | | | | 555 | | | | | 560 |
| Leu | Ile | Ser | Leu | Asn | Val | Pro | Glu | Val | Glu | Val | Lys | Thr | Val | Asp |
| | | | 565 | | | | | 570 | | | | | 575 | |
| Gly | Tyr | Gln | Gly | Arg | Glu | Lys | Glu | Val | Ile | Ile | Leu | Ser | Phe | Val | Arg |
| | | | 580 | | | | | 585 | | | | | 590 | | |
| Ser | Asn | Lys | Ala | Gly | Glu | Ile | Gly | Phe | Leu | Lys | Asp | Leu | Arg | Arg | Leu |
| | | 595 | | | | | 600 | | | | | 605 | | | |
| Asn | Val | Ser | Leu | Thr | Arg | Ala | Lys | Arg | Lys | Leu | Ile | Met | Ile | Gly | Asp |
| | | 610 | | | | | 615 | | | | | 620 | | | |
| Ser | Ser | Thr | Leu | Ser | Ser | His | Glu | Thr | Tyr | Arg | Arg | Leu | Ile | Glu | His |
| 625 | | | | | 630 | | | | | 635 | | | | | 640 |
| Val | Arg | Glu | Lys | Gly | Leu | Tyr | Val | Leu | Thr | Lys | Asp | Ser | Ile |
| | | | | 645 | | | | | 650 | | | | | 655 |

<210> SEQ ID NO 81
<211> LENGTH: 2163
<212> TYPE: DNA
<213> ORGANISM: Artificial Sequence
<220> FEATURE:
<223> OTHER INFORMATION: Description of Artificial Sequence: Recombinant helicase 8

<400> SEQUENCE: 81

| | |
|---|---|
| atgagggttg atgagctgag agttgatgag aggataaaga gtactttgaa ggagagaggt | 60 |
| atcgaatcct tttaccctcc ccaagccgag gccttaaaga gcgggatatt ggaaggtaag | 120 |
| aatgcattaa tttcaattcc aacggccagc ggaaaaacac taattgctga gattgccatg | 180 |
| gttcatagga ttttgaccca gggaggaaag gctgtataca tagtcccgct gaaggccttg | 240 |
| gctgaagaaa agtttcagga gttccaggat gggagaaga ttgggttaag agtagcgatg | 300 |
| gccactgggg attacgactc aaaggatgag tggttgggga aatacgacat aatcattgcg | 360 |
| acggctgaga gtttgattc ccttttaagg catggctcaa gttggattaa ggatgtgaag | 420 |
| attttagttg ctgacgagat tcatttgatt ggttcaagag acagaggagc tacgcttgaa | 480 |
| gttatcctag ctcatatgct cggaaaggcc caaataattg gactctctgc aacgatagga | 540 |
| aatccagaga agcttgcgga gtggttaaat gccgagctaa tagtcagtga ctggaggccc | 600 |
| gttaagctta aaggggagt tttttaccaa ggctttgtta cctgggaaga tggaagtata | 660 |
| gacaggtttt cctcctggga agagttagtt tacgatgcaa ttaggaagaa gaaaggagcg | 720 |
| ctaattttg taaacatgag aaggaaggct gagagagtag ctttggagct ttctaaaaaa | 780 |
| gttaagtctc tcctcacgaa acctgagatt agagctttaa atgaattggc tgattccctc | 840 |
| gaggaaaatc ccacaaatga aaagctagct aaggccatta ggggtggagt tgcgttccac | 900 |
| cacgctggtc ttgggagaga tgagagggtt ctcgtggagg agaactttag aaagggtata | 960 |
| ataaaggccg tagttgccac cccaacactt tcggcgggaa ttaacactcc agcgtttagg | 1020 |
| gtgattataa gggatatttg gaggtactct gactttggaa tggagagaat tccgataatc | 1080 |
| gaggttcacc aaatgcttgg gagagctgga aggccgaagt atgatgaggt tgggagggga | 1140 |

```
ataatagttt ctacaagcga tgatccgaga gaggtaatga atcactacat atttggaaag    1200
cctgaaaaac tgttctccca gctctccaac gagagtaatt tgagaagtca agttttggcc    1260
ctaatagcga cctttggcta ttcaactgtg gaggagattt tgaagttcat ctcaaacaca    1320
ttctatgctt atcaaaggaa ggacacatac tctttagagg agaagataag gaacatactc    1380
tacttcctcc tagagaatga gttcatagag atatccttag aggataaaat aaggccgctt    1440
tccctgggaa ttaggactgc aaagctttat atcgatccct atacggccaa gatgttcaag    1500
gataaaatgg aggaagttgt taaagatcca atcctatag gaatatttca cttaatctcc    1560
ctaactccgg atataacccc cttcaactac tcaaagagaa aatttgaaag gctcgaagag    1620
gaatactacg aattcaagga taggttatac tttgacgatc cctacatttc gggttacgac    1680
ccctacctag agaggaagtt cttcagagct ttcaaaactg cactagtgct tctggcatgg    1740
ataaatgaag tccctgaggg agaaatagtt gaaaagtact cggtggaacc tggggacatc    1800
tataggatag ttgagacggc tgagtggctg gtgtactctc taaaggaaat tgcaaaagtt    1860
cttggagctt atgagatcgt tgattatctt gaaacattga gggttagggt caagtatggg    1920
attagggagg aattgattcc cctaatgcaa ctcccgttgg ttggaagaag gagagctaga    1980
gctctttaca atagcggatt tagaagtata gaggatatat ctcaagcgag gccagaagag    2040
cttttgaaaa tcgaggggat aggggtcaag accgttgagg ctatcttcaa gtttcttggt    2100
aagaatgtga aaatttcgga gaaacctaga aaaagtaccc ttgattactt tctcaaatct    2160
tga                                                                  2163
```

<210> SEQ ID NO 82
<211> LENGTH: 720
<212> TYPE: PRT
<213> ORGANISM: Artificial Sequence
<220> FEATURE:
<223> OTHER INFORMATION: Description of Artificial Sequence: Recombinant helicase 8

<400> SEQUENCE: 82

```
Met Arg Val Asp Glu Leu Arg Val Asp Glu Arg Ile Lys Ser Thr Leu
  1               5                  10                  15

Lys Glu Arg Gly Ile Glu Ser Phe Tyr Pro Pro Gln Ala Glu Ala Leu
             20                  25                  30

Lys Ser Gly Ile Leu Glu Gly Lys Asn Ala Leu Ile Ser Ile Pro Thr
         35                  40                  45

Ala Ser Gly Lys Thr Leu Ile Ala Glu Ile Ala Met Val His Arg Ile
     50                  55                  60

Leu Thr Gln Gly Gly Lys Ala Val Tyr Ile Val Pro Leu Lys Ala Leu
 65                  70                  75                  80

Ala Glu Glu Lys Phe Gln Glu Phe Gln Asp Trp Glu Lys Ile Gly Leu
                 85                  90                  95

Arg Val Ala Met Ala Thr Gly Asp Tyr Asp Ser Lys Asp Glu Trp Leu
            100                 105                 110

Gly Lys Tyr Asp Ile Ile Ala Thr Ala Glu Lys Phe Asp Ser Leu
            115                 120                 125

Leu Arg His Gly Ser Ser Trp Ile Lys Asp Val Lys Ile Leu Val Ala
        130                 135                 140

Asp Glu Ile His Leu Ile Gly Ser Arg Asp Arg Gly Ala Thr Leu Glu
145                 150                 155                 160

Val Ile Leu Ala His Met Leu Gly Lys Ala Gln Ile Ile Gly Leu Ser
                165                 170                 175
```

-continued

```
Ala Thr Ile Gly Asn Pro Glu Glu Leu Ala Glu Trp Leu Asn Ala Glu
            180                 185                 190

Leu Ile Val Ser Asp Trp Arg Pro Val Lys Leu Arg Arg Gly Val Phe
        195                 200                 205

Tyr Gln Gly Phe Val Thr Trp Glu Asp Gly Ser Ile Asp Arg Phe Ser
    210                 215                 220

Ser Trp Glu Glu Leu Val Tyr Asp Ala Ile Arg Lys Lys Lys Gly Ala
225                 230                 235                 240

Leu Ile Phe Val Asn Met Arg Arg Lys Ala Glu Arg Val Ala Leu Glu
                245                 250                 255

Leu Ser Lys Lys Val Lys Ser Leu Leu Thr Lys Pro Glu Ile Arg Ala
            260                 265                 270

Leu Asn Glu Leu Ala Asp Ser Leu Glu Glu Asn Pro Thr Asn Glu Lys
        275                 280                 285

Leu Ala Lys Ala Ile Arg Gly Gly Val Ala Phe His His Ala Gly Leu
    290                 295                 300

Gly Arg Asp Glu Arg Val Leu Val Glu Glu Asn Phe Arg Lys Gly Ile
305                 310                 315                 320

Ile Lys Ala Val Val Ala Thr Pro Thr Leu Ser Ala Gly Ile Asn Thr
                325                 330                 335

Pro Ala Phe Arg Val Ile Ile Arg Asp Ile Trp Arg Tyr Ser Asp Phe
            340                 345                 350

Gly Met Glu Arg Ile Pro Ile Ile Glu Val His Gln Met Leu Gly Arg
        355                 360                 365

Ala Gly Arg Pro Lys Tyr Asp Glu Val Gly Glu Gly Ile Ile Val Ser
    370                 375                 380

Thr Ser Asp Asp Pro Arg Glu Val Met Asn His Tyr Ile Phe Gly Lys
385                 390                 395                 400

Pro Glu Lys Leu Phe Ser Gln Leu Ser Asn Glu Ser Asn Leu Arg Ser
                405                 410                 415

Gln Val Leu Ala Leu Ile Ala Thr Phe Gly Tyr Ser Thr Val Glu Glu
            420                 425                 430

Ile Leu Lys Phe Ile Ser Asn Thr Phe Tyr Ala Tyr Gln Arg Lys Asp
        435                 440                 445

Thr Tyr Ser Leu Glu Glu Lys Ile Arg Asn Ile Leu Tyr Phe Leu Leu
    450                 455                 460

Glu Asn Glu Phe Ile Glu Ile Ser Leu Glu Asp Lys Ile Arg Pro Leu
465                 470                 475                 480

Ser Leu Gly Ile Arg Thr Ala Lys Leu Tyr Ile Asp Pro Tyr Thr Ala
                485                 490                 495

Lys Met Phe Lys Asp Lys Met Glu Glu Val Val Lys Asp Pro Asn Pro
            500                 505                 510

Ile Gly Ile Phe His Leu Ile Ser Leu Thr Pro Asp Ile Thr Pro Phe
        515                 520                 525

Asn Tyr Ser Lys Arg Glu Phe Glu Arg Leu Glu Glu Tyr Tyr Glu
    530                 535                 540

Phe Lys Asp Arg Leu Tyr Phe Asp Pro Tyr Ile Ser Gly Tyr Asp
545                 550                 555                 560

Pro Tyr Leu Glu Arg Lys Phe Phe Arg Ala Phe Lys Thr Ala Leu Val
                565                 570                 575

Leu Leu Ala Trp Ile Asn Glu Val Pro Glu Gly Glu Ile Val Glu Lys
            580                 585                 590
```

```
Tyr Ser Val Glu Pro Gly Asp Ile Tyr Arg Ile Val Glu Thr Ala Glu
        595                 600                 605

Trp Leu Val Tyr Ser Leu Lys Glu Ile Ala Lys Val Leu Gly Ala Tyr
    610                 615                 620

Glu Ile Val Asp Tyr Leu Glu Thr Leu Arg Val Arg Val Lys Tyr Gly
625                 630                 635                 640

Ile Arg Glu Glu Leu Ile Pro Leu Met Gln Leu Pro Leu Val Gly Arg
                645                 650                 655

Arg Arg Ala Arg Ala Leu Tyr Asn Ser Gly Phe Arg Ser Ile Glu Asp
                660                 665                 670

Ile Ser Gln Ala Arg Pro Glu Leu Leu Lys Ile Glu Gly Ile Gly
        675                 680                 685

Val Lys Thr Val Glu Ala Ile Phe Lys Phe Leu Gly Lys Asn Val Lys
    690                 695                 700

Ile Ser Glu Lys Pro Arg Lys Ser Thr Leu Asp Tyr Phe Leu Lys Ser
705                 710                 715                 720

<210> SEQ ID NO 83
<211> LENGTH: 2163
<212> TYPE: DNA
<213> ORGANISM: Pyrococcus furiosus

<400> SEQUENCE: 83
atgagggttg atgagctgag agttgatgag aggataaaga gtactttgaa ggagagaggt      60
atcgaatcct tttaccctcc ccaagccgag gccttaaaga gcgggatatt ggaaggtaag    120
aatgcattaa tttcaattcc aacggccagc ggaaaaacac taattgctga gattgccatg    180
gttcatagga ttttgaccca gggaggaaag gctgtataca tagtcccgct gaaggccttg    240
gctgaagaaa agtttcagga gttccaggat tgggagaaga ttgggttaag agtagcgatg    300
gccactgggg attacgactc aaaggatgag tggttgggga atacgacat aatcattgcg     360 acggctgaga agtttgattc cctttttaagg catggctcaa gttggattaa ggatgtgaag   420
attttagttg ctgacgagat tcatttgatt ggttcaagag acagaggagc tacgcttgaa    480
gttatcctag ctcatatgct cggaaaggcc caaataattg gactctctgc aacgatagga    540
aatccgagag agcttgcgga gtggttaaat gccgagctaa tagtcagtga ctggaggccc    600
gttaagctta aagggggagt tttttaccaa ggctttgtta cctgggaaga tggaagtata    660
gacaggtttt cctcctggga agagttagtt tacgatgcaa ttaggaagaa gaaaggagcg    720
ctaatttttg taaacatgag aaggaaggct gagagagtag ctttggagct ttctaaaaaa    780
gttaagtctc tcctcacgaa acctgagatt agagctttaa atgaattggc tgattccctc    840
gaggaaaatc ccacaaatga aaagctagct aaggccatta ggggtggagt tgcgttccac    900
cacgctggtc ttgggagaga tgagagggtt ctcgtggagg agaactttag aaagggtata    960
ataaaggccg tagttgccac cccaacactt tcggcgggaa ttaacactcc agcgtttagg   1020
gtgattataa gggatatttg gaggtactct gactttggaa tggagagaat tccgataatc   1080
gaggttcacc aaatgcttgg gagagctgga aggccgaagt atgatgaggt tgggaggga   1140 ataatagttt ctacaagcga tgatccgaga gaggtaatga atcactacat atttggaaag   1200
cctgaaaaac tgttctccca gctctccaac gagagtaatt tgagaagtca agttttggcc   1260
ctaatagcga cctttggcta ttcaactgtg gaggagattt tgaagttcat ctcaaacaca   1320
ttctatgctt atcaaaggaa ggacacatac tcttttagagg agaagataag gaacatactc   1380
tacttcctcc tagagaatga gttcatagag atatccttag aggataaaat aaggccgctt   1440
```

-continued

```
tccctgggaa ttaggactgc aaagctttat atcgatccct atacggccaa gatgttcaag    1500
gataaaatgg aggaagttgt taaagatcca atcctatag  gaatatttca cttaatctcc    1560
ctaactccgg atataacccc cttcaactac tcaaagagag aatttgaaag gctcgaagag    1620
gaatactacg aattcaagga taggttatac tttgacgatc cctacatttc gggttacgac    1680
ccctacctag agaggaagtt cttcagagct ttcaaaactg cactagtgct tctggcatgg    1740
ataaatgaag tccctgaggg agaaatagtt gaaaagtact cggtggaacc tggggacatc    1800
tataggatag ttgagacggc tgagtggctg gtgtactctc taaaggaaat tgcaaaagtt    1860
cttggagctt atgagatcgt tgattatctt gaaacattga gggttagggt caagtatggg    1920
attagggagg aattgattcc cctaatgcaa ctcccgttgg ttggaagaag gagagctaga    1980
gctctttaca atagcggatt tagaagtata gaggatatat ctcaagcgag gccagaagag    2040
cttttgaaaa tcgaggggat aggggtcaag accgttgagg ctatcttcaa gtttcttggt    2100
aagaatgtga aaatttcgga gaaacctaga aaaagtaccc ttgattactt tctcaaatct    2160
tga                                                                   2163
```

<210> SEQ ID NO 84
<211> LENGTH: 720
<212> TYPE: PRT
<213> ORGANISM: Pyrococcus furiosus

<400> SEQUENCE: 84

```
Met Arg Val Asp Glu Leu Arg Val Asp Glu Arg Ile Lys Ser Thr Leu
 1               5                  10                  15

Lys Glu Arg Gly Ile Glu Ser Phe Tyr Pro Pro Gln Ala Glu Ala Leu
            20                  25                  30

Lys Ser Gly Ile Leu Glu Gly Lys Asn Ala Leu Ile Ser Ile Pro Thr
        35                  40                  45

Ala Ser Gly Lys Thr Leu Ile Ala Glu Ile Ala Met Val His Arg Ile
    50                  55                  60

Leu Thr Gln Gly Gly Lys Ala Val Tyr Ile Val Pro Leu Lys Ala Leu
65                  70                  75                  80

Ala Glu Glu Lys Phe Gln Glu Phe Gln Asp Trp Glu Lys Ile Gly Leu
                85                  90                  95

Arg Val Ala Met Ala Thr Gly Asp Tyr Asp Ser Lys Asp Glu Trp Leu
            100                 105                 110

Gly Lys Tyr Asp Ile Ile Ile Ala Thr Ala Glu Lys Phe Asp Ser Leu
        115                 120                 125

Leu Arg His Gly Ser Ser Trp Ile Lys Asp Val Lys Ile Leu Val Ala
    130                 135                 140

Asp Glu Ile His Leu Ile Gly Ser Arg Asp Arg Gly Ala Thr Leu Glu
145                 150                 155                 160

Val Ile Leu Ala His Met Leu Gly Lys Ala Gln Ile Ile Gly Leu Ser
                165                 170                 175

Ala Thr Ile Gly Asn Pro Glu Glu Leu Ala Glu Trp Leu Asn Ala Glu
            180                 185                 190

Leu Ile Val Ser Asp Trp Arg Pro Val Lys Leu Arg Arg Gly Val Phe
        195                 200                 205

Tyr Gln Gly Phe Val Thr Trp Glu Asp Gly Ser Ile Asp Arg Phe Ser
    210                 215                 220

Ser Trp Glu Glu Leu Val Tyr Asp Ala Ile Arg Lys Lys Lys Gly Ala
225                 230                 235                 240
```

```
-continued

Leu Ile Phe Val Asn Met Arg Arg Lys Ala Glu Arg Val Ala Leu Glu
                245                 250                 255

Leu Ser Lys Lys Val Lys Ser Leu Leu Thr Lys Pro Glu Ile Arg Ala
            260                 265                 270

Leu Asn Glu Leu Ala Asp Ser Leu Glu Glu Asn Pro Thr Asn Glu Lys
        275                 280                 285

Leu Ala Lys Ala Ile Arg Gly Val Ala Phe His His Ala Gly Leu
    290                 295                 300

Gly Arg Asp Glu Arg Val Leu Val Glu Glu Asn Phe Arg Lys Gly Ile
305                 310                 315                 320

Ile Lys Ala Val Val Ala Thr Pro Thr Leu Ser Ala Gly Ile Asn Thr
                325                 330                 335

Pro Ala Phe Arg Val Ile Arg Asp Ile Trp Arg Tyr Ser Asp Phe
                340                 345                 350

Gly Met Glu Arg Ile Pro Ile Ile Glu Val His Gln Met Leu Gly Arg
                355                 360                 365

Ala Gly Arg Pro Lys Tyr Asp Glu Val Gly Glu Gly Ile Ile Val Ser
    370                 375                 380

Thr Ser Asp Asp Pro Arg Glu Val Met Asn His Tyr Ile Phe Gly Lys
385                 390                 395                 400

Pro Glu Lys Leu Phe Ser Gln Leu Ser Asn Glu Ser Asn Leu Arg Ser
                405                 410                 415

Gln Val Leu Ala Leu Ile Ala Thr Phe Gly Tyr Ser Thr Val Glu Glu
                420                 425                 430

Ile Leu Lys Phe Ile Ser Asn Thr Phe Tyr Ala Tyr Gln Arg Lys Asp
            435                 440                 445

Thr Tyr Ser Leu Glu Glu Lys Ile Arg Asn Ile Leu Tyr Phe Leu Leu
    450                 455                 460

Glu Asn Glu Phe Ile Glu Ile Ser Leu Glu Asp Lys Ile Arg Pro Leu
465                 470                 475                 480

Ser Leu Gly Ile Arg Thr Ala Lys Leu Tyr Ile Asp Pro Tyr Thr Ala
                485                 490                 495

Lys Met Phe Lys Asp Lys Met Glu Glu Val Val Lys Asp Pro Asn Pro
                500                 505                 510

Ile Gly Ile Phe His Leu Ile Ser Leu Thr Pro Asp Ile Thr Pro Phe
            515                 520                 525

Asn Tyr Ser Lys Arg Glu Phe Glu Arg Leu Glu Glu Tyr Tyr Glu
    530                 535                 540

Phe Lys Asp Arg Leu Tyr Phe Asp Asp Pro Tyr Ile Ser Gly Tyr Asp
545                 550                 555                 560

Pro Tyr Leu Glu Arg Lys Phe Phe Arg Ala Phe Lys Thr Ala Leu Val
                565                 570                 575

Leu Leu Ala Trp Ile Asn Glu Val Pro Glu Gly Glu Ile Val Glu Lys
            580                 585                 590

Tyr Ser Val Glu Pro Gly Asp Ile Tyr Arg Ile Val Glu Thr Ala Glu
    595                 600                 605

Trp Leu Val Tyr Ser Leu Lys Glu Ile Ala Lys Val Leu Gly Ala Tyr
    610                 615                 620

Glu Ile Val Asp Tyr Leu Glu Thr Leu Arg Val Arg Val Lys Tyr Gly
625                 630                 635                 640

Ile Arg Glu Glu Leu Ile Pro Leu Met Gln Leu Pro Leu Val Gly Arg
                645                 650                 655
```

```
                Arg Arg Ala Arg Ala Leu Tyr Asn Ser Gly Phe Arg Ser Ile Glu Asp
                            660                 665                 670

Ile Ser Gln Ala Arg Pro Glu Glu Leu Leu Lys Ile Glu Gly Ile Gly
                        675                 680                 685

Val Lys Thr Val Glu Ala Ile Phe Lys Phe Leu Gly Lys Asn Val Lys
                    690                 695                 700

Ile Ser Glu Lys Pro Arg Lys Ser Thr Leu Asp Tyr Phe Leu Lys Ser
                705                 710                 715                 720
```